US007632655B2

(12) United States Patent
Williams et al.

(10) Patent No.: US 7,632,655 B2
(45) Date of Patent: *Dec. 15, 2009

(54) FLUORESCENCE POLARIZATION ASSAYS FOR DETERMINING CLOSTRIDIAL TOXIN ACTIVITY

(75) Inventors: Dudley J. Williams, Laguna Niguel, CA (US); Marcella Gilmore, Santa Ana, CA (US); Lance Steward, Irvine, CA (US); Marc Verhagen, Irvine, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/125,723

(22) Filed: May 22, 2008

(65) Prior Publication Data

US 2008/0305510 A1 Dec. 11, 2008

Related U.S. Application Data

(63) Continuation of application No. 10/948,097, filed on Sep. 22, 2004, now Pat. No. 7,399,607.

(51) Int. Cl.
*C12Q 1/37* (2006.01)
*C12N 11/16* (2006.01)

(52) U.S. Cl. ......................................... 435/23; 435/174

(58) Field of Classification Search ........................ None
See application file for complete search history.

(56) References Cited

U.S. PATENT DOCUMENTS 5,693,476 A 12/1997 Scheller 5,804,395 A 9/1998 Schade et al.
5,804,604 A 9/1998 Frankel et al.

(Continued)

FOREIGN PATENT DOCUMENTS

WO WO 95/33850 A1 12/1995

(Continued)

OTHER PUBLICATIONS

Cai, S et al, Biochemistry, 2001, vol. 40, pp. 4093-4702, A correlation between differntial structural features and the degree of endopeptidase activity of Type A botulinum neurotoxin in aqueous solution.*

(Continued)

*Primary Examiner*—Robert B Mondesi
*Assistant Examiner*—Ginny Portner
(74) *Attorney, Agent, or Firm*—Dean G. Stathakis; Joel B. German; Debra Condino

(57) ABSTRACT

The present invention provides a method of determining the presence or activity of a clostridial toxin by (a) treating with a sample, under conditions suitable for clostridial toxin protease activity, a clostridial toxin substrate which includes a fluorophore; a bulking group; and a clostridial toxin recognition sequence containing a cleavage site that intervenes between the fluorophore and the bulking group; (b) exciting the fluorophore with plane polarized light; and (c) determining fluorescence polarization of the treated substrate relative to a control substrate, where a change in fluorescence polarization of the treated substrate as compared to fluorescence polarization of the control substrate is indicative of the presence or activity of the clostridial toxin.

28 Claims, 18 Drawing Sheets

U.S. PATENT DOCUMENTS

| | | | |
|---|---|---|---|
| 5,962,637 A | 10/1999 | Shone et al. | |
| 5,965,699 A | 10/1999 | Schmidt et al. | |
| 5,981,200 A | 11/1999 | Tsien et al. | |
| 5,989,545 A | 11/1999 | Foster et al. | |
| 6,043,042 A | 3/2000 | Shone et al. | |
| 6,169,074 B1 | 1/2001 | Montal et al. | |
| 6,197,534 B1 | 3/2001 | Lakowicz et al. | |
| 6,197,928 B1 | 3/2001 | Tsien et al. | |
| 6,221,355 B1 | 4/2001 | Dowdy | |
| 6,280,981 B1* | 8/2001 | Dykens et al. | 435/110 |
| 6,337,386 B1 | 1/2002 | Shone | |
| 6,469,154 B1 | 10/2002 | Tsien et al. | |
| 6,504,006 B1 | 1/2003 | Shine et al. | |
| 6,511,815 B1 | 1/2003 | Burke et al. | |
| 6,762,280 B2* | 7/2004 | Schmidt et al. | 530/300 |
| 7,183,066 B2 | 2/2007 | Fernandez-Salas et al. | |
| 7,198,928 B2 | 4/2007 | Liang et al. | |
| 7,208,285 B2 | 4/2007 | Steward et al. | |
| 7,495,069 B2* | 2/2009 | Steward et al. | 530/300 |
| 2001/0046668 A1 | 11/2001 | Levine et al. | |
| 2002/0127623 A1 | 9/2002 | Minshull et al. | |
| 2003/0027752 A1 | 2/2003 | Steward et al. | |
| 2003/0077685 A1 | 4/2003 | Schmidt et al. | |
| 2003/0143650 A1* | 7/2003 | Steward et al. | 435/7.32 |
| 2003/0143651 A1 | 7/2003 | Steward et al. | |
| 2003/0170770 A1 | 9/2003 | Khanna et al. | |
| 2003/0219462 A1 | 11/2003 | Steward et al. | |
| 2004/0038307 A1* | 2/2004 | Lee et al. | 435/7.1 |
| 2004/0072270 A1* | 4/2004 | Fernandez-Salas et al. | 435/7.32 |
| 2004/0115727 A1 | 6/2004 | Steward et al. | |
| 2004/0146956 A1 | 7/2004 | Khanna et al. | |
| 2004/0146963 A1 | 7/2004 | Schmidt et al. | |
| 2004/0241782 A1 | 12/2004 | Lopez-Calle et al. | |
| 2005/0095601 A1 | 5/2005 | Cullum et al. | |
| 2005/0100973 A1 | 5/2005 | Steward et al. | |
| 2005/0106655 A1 | 5/2005 | Savage et al. | |
| 2005/0227306 A1 | 10/2005 | Fox et al. | |
| 2005/0233429 A1 | 10/2005 | Liang et al. | |
| 2006/0024794 A1 | 2/2006 | Li et al. | |
| 2006/0063221 A1 | 3/2006 | Williams et al. | |
| 2006/0063222 A1 | 3/2006 | Williams et al. | |
| 2006/0110778 A1 | 5/2006 | Adorante et al. | |
| 2006/0154314 A9 | 7/2006 | Steward et al. | |
| 2007/0122858 A1 | 5/2007 | Fernandez-Salas et al. | |

FOREIGN PATENT DOCUMENTS

| | | |
|---|---|---|
| WO | WO 97/34620 A1 | 9/1997 |
| WO | WO 99/29721 A1 | 6/1999 |
| WO | WO 99/55899 A1 | 11/1999 |
| WO | WO 00/34308 A2 | 6/2000 |
| WO | WO 01/18038 A2 | 3/2001 |
| WO | WO 02/25284 A2 | 3/2002 |
| WO | WO 03/020948 A2 | 3/2003 |
| WO | WO 2004/031355 A2 | 4/2004 |
| WO | WO2005/076785 A2 | 8/2005 |

OTHER PUBLICATIONS

Anne et al., "High-Throughput Fluorogenic Assay for Determination of Botulinum Type B Neurotoxin Protease Activity," *Analytical Biochemistry* 291:253-261 (2001).

Autofluorescent Proteins, *AFP's Applications Manual*, pp. 1-25 (Nov. 1998).

Bark, "Structure of the chicken gene for SNAP-25 reveals duplicated exon encoding distinct isoforms of the protein ," *J. Mol. Biol.* 233(1):67-76 (1993).

BD Biosciences Clontech Product List, BD Living Colors™ Fluorescent Proteins, pp. 1-9 (Apr. 2004).

Burnett et al., "Novel small molecule inhibitors of botulinum neurotoxin A metalloprotease activity," *Biochem. Biophys. Res. Commun.* 310(1):84-93 (2003).

Calbiochem, "SNAPtide® Botulinum Toxin A Substrate, Fluorogenic," www.calbiochem.com, printed on Dec. 17, 2002.

Catsicas et al., "Expression of a conserved cell-type-specific protein in nerve terminals coincides with synaptogenesis ," *Proc. Natl. Acad. Sci. U.S.A.* 88(3):785-789 (1991).

Chen and Selvin, "Thiol-reactive Luminescent Chelates of Terbium and Europium," *Bioconjugate Chem.* 10(2):311-315 (1999).

Christopoulos and Diamandis, "Enzymatically amplified time-resolved fluorescence immunoassay with terbium chelates," *Anal. Chem.* 64(4):342-346 (1992).

CIS Bio International, "Homogeneous Time Resolved Fluorescence—Methodological aspects," Application Note 1, pp. 1-4, CIS bio international: France (2003).

Clark et al., "A novel peptide designed for sensitization of terbium (III) luminescence," *FEBS Lett.* 333(1-2):96-98 (1993).

Clark et al., "A study of sensitized lanthanide luminescence in an engineered calcium-binding protein," *Anal. Biochem.* 210(1):1-6 (1993).

Clegg, "Fluorescence resonance energy transfer," *Curr. Opin. Biotechnol.* 6(1):103-110 (1995).

Collins, "Generation and initial analysis of more than 15,000 full-length human and mouse cDNA sequences," *Proc. Natl. Acad. Sci. U.S.A.* 99(26):16899-16903 (2002).

Cooper and Sammes, "Synthesis and spectral properties of a new luminescent europium(III) terpyridyl chelate," *J. Chem. Soc., Perkin Trans. 2* 8:1695-1700 (2000).

Cornille et al., "Solid-Phase Synthesis, Conformational Analysis and In Vitro Cleavage of Synthetic Human Synaptobrevin II I-93 by Tetanus Toxin L Chain," *Eur. J. Biochem.* 222:173-181 (1994)

Criado et al. "A single amino acid near the C terminus of the synaptosomeassociated protein of 25 kDa (SNAP-25) is essential for exocytosis in chromaffin cells," *Proc. Natl. Acad. Sci. U.S.A.* 96(13):7256-7261 (1999).

Deloukas et al., "The DNA sequence and comparative analysis of human chromosome 20," *Nature* 414(6866):865-871 (2001).

Diamandis and Christopoulos, "Europium chelate labels in time-resolved fluorescence immunoassays and DNA hybridization assays," *Anal. Chem.* 62(22):1149A-1157A (1990).

Diamandis, "Immunoassays with time-resolved fluorescence spectroscopy: Principles and applications," *Clin. Biochem.* 21(3):139-150 (1988).

Ekong et al., "Recombinant SNAP-25 is an Effective Substrate for *Clostridium botulinum* Type A Toxin Endopeptidase Activity in vitro," *Microbiology* 143:3337-3347 (1997).

Florentin et al., "A Highly Sensitive Fluorometric Assay for 'Enkephalinase,' a Neutral Metalloendopeptidase That Releases Tyrosine-Glycine-Glycine from Enkephalins," *Analytical Biochemistry* 141:62-69 (1984).

Foran et al., "Differences in the Protease Activities of Tetanus and Botulinum B Toxins Revealed by the Cleavage of Vesicle-Associated Membrane Protein and Various Sized Fragments," *Biochemistry* 33:15365-15374 (1994).

Geoghegan et al., "Fluorescence-based Continuous Assay for the Aspartyl Protease of Human Immunodeficiency Virus-1," *FEBS* 262:119-122 (1990).

Gil et al., "Modifications in the C terminus of the synaptosome-associated protein of 25 kDa (SNAP-25) and in the complementary region of synaptobrevin affect the final steps of exocytosis," *J. Biol. Chem.* 277(12):9904-9910 (2002).

Goudreau et al., "Dns-Gly-(p-$NO_2$)Phe-βAla, a Specific Fluorogenic Substrate for Neutral Endopeptidase 24.11," *Analytical Biochemistry* 219:87-95 (1994).

Graham et al., "A method to measure the interaction of Rac/Cdc42 with their binding partners using fluorescence resonance energy transfer between mutants of green fluorescent protein," *Analytical Biochem.* 296:208-217 (2001).

Hallis et al., "Development of Novel Assays for Botulinum Type A and B Neurotoxins Based on Their Endopeptidase Activities," *J. Clin. Microbiol.* 34:1934-1938 (1996).

Hanson and Stevens, "Cocrystal Structure of Synaptobrevin-II Bound to Botulinum Neurotoxin Type B at 2.0 Å Resolution," *Nature Structural Biology* 7:687-692 (2000).

Hess et al., "The 25 kDa synaptosomal-associated protein SNAP-25 is the major methionine-rich polypeptide in rapid axonal transport and a major substrate for palmitoylation in adult CNS," *J. Neurosci.* 12(12):4634-4641 (1992).

Heyduk, "Measuring protein conformational changes by FRET/LRET," *Curr. Opin. Biotechnol.* 13:292-296 (2002).

Hodel, "Molecules in Focus: SNAP-25," *Int. J. Biochem. & Cell Biol.* 30:1069-1073 (1998).

Holskin et al., "A Continuous Fluorescence-Based Assay of Human Cytomegalovirus Protease Using a Peptide Substrate," *Analytical Biochemistry* 226:148-155 (1995).

Huang et al., "$Ca^{2+}$ influx and cAMP elevation overcame botulinum toxin A but not tetanus toxin inhibition of insulin exocytosis," *Am. J. Physiol. Cell Physiol.* 281:C740-C750 (2001).

Humeau et al., "How Botulinum and Tetanus Neurotoxins Block Neurotransmitter Release," *Biochimie* 82:427-446 (2000).

Jacobsson et al., "Differential subcellular localization of SNAP-25a and SNAP-25b RNA transcripts in spinal motoneurons and plasticity in expression after nerve injury," *Brain Res. Mol. Brain Res.* 37(1-2):49-62 (1996).

Jagadish et al., "Insulin-responsive tissues contain the core complex protein SNAP-25 (synaptosomal-associated protein 25) A and B isoforms in addition to syntaxin 4 and synaptobrevins 1 and 2," *Biochem. J.* 317(Pt 3):945-954 (1996).

Kakiuchi et al., "A High Throughput Assay of the Hepatitis C Virus Nonstructural Protein 3 Serine Proteinase," *Journal of Virological Methods* 80:77-84 (1999).

Kalandakanond and Coffield, "Cleavage of SNAP-25 by botulinum toxin type A requires receptor-mediated endocytosis, pH-dependent translocation, and zinc," *J. Pharmacol. Exp. Ther.* 296(3):980-986 (2001).

Kam et al., "Probing molecular processes in live cells by quantitative multidimensional microscopy," *Trends in Cell Biology* 11:329-334 (2001).

Kawasaki and Kretsinger, "Calcium Binding Proteins 1: EF-hands," *Protein Profile* 1(4):343-517, Sheterline et al. (eds.), Academic Press: London (1994).

Knapp et al., "The Crystal Structure of Botulinum Toxin A zinc Protease Domain" abstract of presentation, *37th Annual Meeting of the Interagency Botulism Research Coordinating Committee* Asilomar, CA (2000).

Kolb et al., "Use of a novel homogenous fluorescent technology in high throughput screening," *J. Biomol. Screening* 1.203-210 (1996).

Kolb et al., in Devlin (ed.), *High Throughput Screening: The Discovery of Bioactive Substances*, pp. 345-360, New York: Marcel Dekker (1997).

Lacy et al., "Crystal Structure of Botulinum Neurotoxin Type A and Implications for Toxicity," *Nature Structural Biology* 5:898-902 (1998).

Le Bonniec et al., "Characterization of the $P_2'$ and $P_3'$ Specificities of Thrombin Using Fluorescence-Quenched Substrates and Mapping of the Subsites by Mutagenesis," *Biochemistry* 35:7114-7122 (1996).

Lewit-Bentley, "EF-hand calcium-binding proteins," *Curr. Opin. Struct. Biol*, 10(6):637-643 (2000).

Li and Selvin, "Luminescent Lanthanide Polyaminocarboxylate Chelates: The Effect of Chelate Structure," *J. Am. Chem. Soc.* 117:8132-8138 (1995).

Li and Selvin, "Amine-Reactive Forms of a Luminescent Diethylenetriaminepentaacetic Acid Chelate of Terbium and Europium: Attachment to DNA and Energy Transfer Measurements," *Bioconjugate Chem.* 8:127-132 (1997).

Lippincott-Schwartz and Patterson, "Development and use of fluorescent protein markers in living cells,"*Science* 300:87-91 (2003).

List Biological Laboratories, "SNAPtide For Fluorometric Measurement of Botulinum Toxin Type A Activity," www.listiabs.com, printed on Dec. 23, 2002.

List Biological Laboratories, Inc., "Botulinum Neurotoxins," web page: http://www.listlabs.com/Literature/130.htm (Printed: Dec. 10, 2004).

List Biological Laboratories, Inc., "What's new?," web page: http://www.listlabs.com/listopener.htm (Printed: Dec. 9, 2004).

MacManus et al., "A new member of the troponin C superfamily: Comparison of the primary structures of rat oncomodulin and rat parvalbumin," *Biosci. Rep.* 3(11):1071-1075 (1983).

Mahajan et al., "Novel Mutant Green Fluorescent Protein Protease Substrates Reveal the Activation of Specific Caspases During Apoptosis," *Chemistry & Biology* 6:401-409 (1999).

Mathis, "Homogeneous immunoassay and other applications of a novel fluorescence energy transfer technology using rare earth cryptates," *J. Clin. Ligand Assay* 20:141-147 (1997).

Mathis, "Probing molecular interactions with homogeneous techniques based on rare earth cryptates and fluorescence energy transfer," *Clin. Chem.* 41(9):1391-137 (1995).

Matsumoto et al., "A High-Throughput Screening Utilizing Intramolecular Fluorescence Resonance Energy Transfer for the Discovery of the Molecules that Bind HIV-1 TAR RNA Specifically," *Bioorganic & Medicinal Chemistry Letters* 10:1857-1861 (2000).

Molecular Probes, "Section 10.4—Detecting Peptidases and Proteases," *Molecular Probes Handbook*, web page http://www.probes.com/handbook/sections/1004.html Updated Aug. 3, 2003.

Montecucco and Schiavo, "Structure and Function of Tetanus and Botulinum Neurotoxins," *Quarterly Reviews of Biophysics* 28:423-472 (1995).

Moore et al., "Reactivation of 3-Dehydroquinate Synthase by Lanthanide Cations," *J. Am. Chem. Soc*. 120:7105-7106 (1998).

Nakayama and Kretsinger, "Evolution of the EF-hand family of proteins," *Annu. Rev. Biophys. Biomol. Struct*. 23:473-507 (1994).

Neale et al., "Botulinum neurotoxin A blocks synaptic vesicle exocytosis but not endocytosis at the nerve terminal," *J. Cell Biology* 147:1249-1260 (1999).

Niemann et al., "Clostridial Neurotoxins: New Tools for Dissecting Exocytosis," *Trends in Cell Biology* 4:179-185 (1994).

Nitz et al., "A powerful combinatorial screen to identify high-affinity terbium(III)-binding peptides," *Chembiochem* 4(4):272-276 (2003).

Nitz et al., "Structural origin of the high affinity of a chemically evolved lanthanide-binding peptide," *Angew Chem. Int. Ed. Engl.* 43(28):3682-3685 (2004).

Olsen et al., "High-throughput Screening of Enzyme Libraries," *Curr. Opin. Biotechnol.* 11:331-337 (2000).

Oyler et al., "The identification of a novel synaptosomal-associated protein, SNAP-25, differentially expressed by neuronal subpopulations ," *J. Cell Biol.* 109 (6, Pt. 1):3039-3052 (1989).

Pellizzari et al., "Tetanus and Botulinum Neurotoxins: Mechanism of Action and Therapeutic Uses," *Phil. Trans. R. Soc. Lond.* 354:259-268 (1999).

PerkinElmer Life Sciences, "Applications of time-resolved fluorometry with the DELFIA® method," pp. 1-23 (2002).

Perpetuo et al., "Development of an operational synaptobrevin-based fluorescent substrate for tetanus neurotoxin quantification," *Biotechnol. Appl. Biochem.* 36:155-161 (2002).

Petoud et al., "Stable lanthanide luminescence agents highly emissive in aqueous solution: Multidentate 2-hydroxyisophthalamide complexes of Sm(3+), Eu(3+), Tb(3+), Dy(3+)," *J. Am. Chem. Soc.* 125(44):13324-13325 (2003).

Pidcock and Moore, "Structural characteristics of protein binding sites for calcium and lanthanide ions," *J. Biol. Inorg. Chem.* 6(5-6):479-489 (2001).

Plafker and Macara, "Fluorescence resonance energy transfer biosensors that detect Ran conformational changes and a Ran•GDP-importin-β-RanBP1 complex in vitro and in intact cells," *J. Biol. Chem.* 277(33):30121-30127 (2002).

Reifenberger et al., "Emission Polarization of Europium and Terbium Chelates," *J. Phys. Chem. B* 107:12862-12873 (2003).

Risinger and Larhammar, "Multiple loci for synapse protein SNAP-25 in the tetraploid goldfish," *Proc. Natl. Acad. Sci. U.S.A.* 90(22):10598-10602 (1993).

Risinger et al., "Cloning of two loci for synapse protein Snap25 in zebrafish: Comparison of paralogous linkage groups suggests loss of one locus in the mammalian lineage ," *J. Neurosci. Res.* 54:563-573 (1998).

Rossetto et al., "Tetanus and Botulinum Neurotoxins: Turning Bad Guys Into Good by Research," *Toxicon* 39:27-41 (2001).

Schmidt and Bostian, "Proteolysis of Synthetic Peptides by Type A Botulinum Neurotoxin," *J. Protein Chem.* 14(8):703-708 (1995).

Schmidt and Bostian, "Endoproteinase Activity of Type A Botulinum Neurotoxin: Substrate Requirements and Activation by Serum Albumin," *J. Protein Chem.* 16(1):19-26 (1997).

Schmidt and Stafford, "A high-affinity competitive inhibitor of type A botulinum neurotoxin protease activity," *FEBS Lett.* 532(3):423-426 (2002).

Schmidt and Stafford, "Fluorigenic substrates for the protease activities neurotoxins, serotypes A, B, and F," *Appl. Environ. Microbiol.* 69(1):297-303 (2003); *Erratum in: Appl. Environ Microbiol.* 69(5):3025. (May 2003).

Schmidt et al., "Type A Botulinum Neurotoxin Proteolytic Activity: Development of Competitive Inhibitors and Implications for Substrate Specificity at the $S_1'$ Binding Subsite," *FEBS Lett.* 435:61-64 (1998).

Schmidt et al., "High-throughput assays for botulinum neurotoxin proteolytic activity: Serotypes A, B, D, and F," *Analytical Biochem.* 296:130-137 (2001).

Selvin et al. "Luminescence resonance energy transfer," *J. Am. Chem. Soc.* 116:6029-6030 (1994).

Selvin, "Fluorescence resonance energy transfer," *Methods Enzymol*, 246:300-334 (1995).

Selvin, "The Renaissance of Fluorescence Resonance Energy Transfer," *Nature Structural Biology* 7(9):730-734 (2000).

Selvin, "Principles and biophysical applications of lanthanide-based probes," *Annu. Rev. Biophys. Biomol. Struct.* 31:275-302 (2002).

Shavaleev et al., "Sensitized near-infrared emission from complexes of YbIII, NdIII and ErIII by energy-transfer from covalently attached PtII-based antenna units," *Chem. Eur. J.* 9(21):5283-5291 (2003).

Shine et al., "Sensitive method for detection of botulinum toxin type A," abstract, The 38th Interagency Botulism Research Coordinating Committee Meeting, Oct. 17-19, 2001.

Shine et al., "A continuous fluorimetric assay for high-throughput screening for botulinum toxin type A inhibitors," *Naunyn Schmiedebergs Arch. Pharmacol*, 365(Supp. 2):R40 (Jun. 2002).

Shone et al., "Proteolytic Cleavage of Synthetic Fragments of Vesicle-Associated Membrane Protein, Isoform-2 by Botulinum Type B Neurotoxin," *Eur. J. Biochem.* 217:965-971 (1993).

Siegel R. et al, "Measurement of molecular interactions in living cells by fluorescence resonance energy transfer between variants of green fluorescent protein", STKE, Jun. 27, 2000, pp. 1-6.

Sittampalam et al., "High-Throughput Screening: Advances in Assay Technologies," *Current Opinion in Chemical Biology* 1:384-391 (1997).

Strynadka and James, "Crystal structures of the helix-loop-helix calcium-binding proteins," *Annu. Rev. Biochem.* 58:951-998 (1989).

Swaminathan and Eswaramoorthy, "Structural Analysis of the Catalytic and Binding Sites of *Clostridium botulinum* Neurotoxin B," *Nature Structural Biology* 7:693-699 (2000).

Tawa et al., "Quantitative Analysis of Fluorescent Caspase Substrate Cleavage in Intact Cells and Identification of Novel Inhibitors of Apoptosis," *Cell Death and Differentiation* 8:30-37 (2001).

Tomchick et al., "Adaptation of an enzyme to regulatory function: Structure of Bacillus subtilis PyrR, a pyr RNA-binding attenuation protein and uracil phosphoribosyltransferase," *Structure* 6(3):337-350 (1998).

Trinquet et al., "New europium cryptates to probe molecular interactions using HTRF®," Application Note 7, pp. 1-3, CIS bio international: France (2003).

Vaidyanathan et al., "Proteolysis of SNAP-25 Isoforms by Botulinum Neurotoxin Types A, C and E: Domains and Amino Acid Residues Controlling the Formation of Enzyme-Substrate Complexes and Cleavage," *J. Neurochem.* 72:327-337 (1999).

Vadakkanchery V. et al, "Proteolysis of SNAP-25 isoforms by botulinum neurotoxin types A, C, and E: Domains and amino acid residues controlling the formation of enzyme-substrate complexes and cleavage", J. Neurochem, vol. 72, 1999, pp. 327-337.

Vazquez-Ibar, et al., "Engineering a terbium-binding site into an integral membrane protein for luminescence energy transfer," *Proc. Natl. Acad. Sci. U.S.A.* 99(6):3487-3492 (2002).

Wang et al., "A Continuous Fluorescence Assay of Reinin Activity," *Analytical Biochemistry* 210:351-359 (1993).

Ward et al., "Spectral perturbations of the Aequorea green fluorescent protein," *Photochem. Photobiol.* 35:803-808 (1982).

Wedin, "One-step fluorescence HTS assays are getting faster, cheaper, smaller, and more sensitive," *Modern Drug Discovery* 2(3):61, 63-64, 66, 68, 71 (1999).

Welch et al., "Lanthanide-binding helix-turn-helix peptides: Solution structure of a designed metallonuclease," *Proc. Natl. Acad. Sci. U.S. A.* 100(7):3725-3730 (2003).

Wilcome et al, FEMS Immunology and Medical Microbiology, vol. 24, pp. 319-323, 1999.

Wu and Brand, "Resonance Energy Transfer: Methods and Applications," *Analytical Biochemistry* 218:1-13 (1994).

Wu et al, "A High-Throughput STAT Binding Assay using Fluorescence polarization, especially see p. 30, col. 2, paragraph 3 "FPM2", and entire document pp. 29-36", Analytical Biochemistry, vol. 249, pp. 29-36, 1997.

Xia and Liu, "Reliable and global measurement of fluorescence resonance energy transfer using fluorescence microscopes," *Biophys. J.* 81(4):2395-2402 (2001).

Xia et al., "Stable SNARE complex prior to evoked synaptic vesicle fusion revealed by fluorescence resonance energy transfer," *J. Biol. Chem.* 276(3):1766-1771 (2001).

Yamasaki et al., "Cleavage of Members of the Synaptobrevin/VAMP Family by Types D and F Botulinal Neurotoxins and Tetanus Toxin," *J. Biol. Chem.* 269:12764-12772 (1994).

Yuan et al., "Synthesis of a terbium fluorescent chelate and its application to time-resolved fluoroimmunoassay," *Anal. Chem.* 73(8):1869-1876 (2001).

Zhang et al., "Creating new fluorescent probes for cell biology," *Nat. Rev. Mol. Cell Biol.* 3(12):906-918 (2002).

Zhao et al., "Cloning and sequence analysis of the human SNAP25 cDNA," *Gene* 145(2):313-314 (1994).

Zimmer, "Green fluorescent protein (GFP): Applications, structure, and related photophysical behavior," *Chem. Rev.* 102(3):759-781 (2002).

Zlokarnik et al., "Quantitation of Transcription and Clonal Selection of Single Living Cells with β-Lactamase as Reporter," *Science* 279(5347):84-88 (1998).

Office Action Date Mailed Jun. 20, 2008 in U.S. Appl. No. 10/598,073.

Keller, James E. et al, FEBS Letters, vol. 456, 1999, pp. 137-142, Persistence of botulinum neurotoxin action in cultured spinal cord cells.

* cited by examiner

|  |  | 1 | 75 |
|---|---|---|---|
| SNAP-25 | Human | (1) | ------MAEDADMRNELEEMQRRADQLADESLESTRRMLQLVEESKDAGIRTTVMLDEQGEQLERIEEGMDQIN |
| SNAP-25 | Mouse | (1) | ------MAEDADMRNELEEMQRRADQLADESLESTRRMLQLVEESKDAGIRTLVMLDEQGEQLERIEEGMDQIN |
| SNAP-25 | Drosophila | (1) | MPADPSEEVAPQVPKTELEELQLNAGVADESSLESTRRMLALDEESKEAGIRTLVLALDEQGEQLDRIEEGMDQIN |
| SNAP-25 | Goldfish | (1) | ------MADEADMRNELADTMQARALQLGDESSLESTRRMLQLVEESKDAGIKTLVMLDEQGEQLERIEEGMDQIN |
| SNAP-25 | Sea Urchin | (1) | ------MEDQNIEMRSELEEIMQSNMQTPESLESTRRMSQMAEESQLNGIERTLVMLDEQGEQILRIEEGMDQIN |
| SNAP-25 | Chicken | (1) | ------MAEDADMRNELRDLEEMQRRADQLADESLESTRRMLQLVEESKDAGIRTLVMLDEQGEQLERIEGMNHIN |

|  |  | 76 | 150 |
|---|---|---|---|
| SNAP-25 | Human | (69) | KDMKEAEKNITDLGRFCGLCVCPCN---KLKSSDAYKKAWGNNQDGVVAS-QPARVVDEREQMAISGGFIRRVTN |
| SNAP-25 | Mouse | (69) | KDMKEAEKNITDLGKFCGLCVCPCN---KLKSSDAYKKAWGNNQDGVVAS-QPARVVDEREQMAISGGFIRRVTN |
| SNAP-25 | Drosophila | (76) | ADMREAEKNITDLGNLCGLCVCPCQ-VLPCNKSQSEKLDS---TWKGNDDGKVNNQDGVVSN-QPFRMAQAYTRKITN |
| SNAP-25 | Goldfish | (69) | KDMKEAEKNITDLGNLCGLCGLCFPCN---KLKGG--GQSWGNNQDGVVSHQPMEDERERQMAISGGFIRRVTN |
| SNAP-25 | Sea Urchin | (71) | TDMPEAEKNITGLERCGICVCEWKKLGNFEKGDDYKRIFVKGNDDGKVNSHQPMEDEDERRGGNASMIGRIN |
| SNAP-25 | Chicken | (69) | QDMKEAEKNIRDLGKFCGIFTCPCN---KLKSSDAYKKAWGNNQDGVVAS-QPARVVDEREQMAISGGFIRRVTN |

|  |  | 151 | 225 |
|---|---|---|---|
| SNAP-25 | Human | (140) | DARENEMDENLEQVSGIIGNLRHMALDMGNEIDTQNRQIDRIMEKADSNKTRIDEAN---QRATKMLGSG------ |
| SNAP-25 | Mouse | (140) | DARENEMDENLEQVSGIIGNLRHMALDMGNEIDTQNRQIDRIMEKADSNKTRIDEAN---QRATKMLGSG------ |
| SNAP-25 | Drosophila | (148) | DAREIEMEMDENLEQVNTMGNLRWMALDMGELERQNRQIDRINRKGESNEARIAVAN---QRAHQLIK------- |
| SNAP-25 | Goldfish | (137) | DAREMEMDENLEQVGSSIGNLRHMALDMGNEIDTQNRQIDRIMEDSNKTRIDEAN---QRATKMLGSG------ |
| SNAP-25 | Sea Urchin | (146) | DAREEMDEMIDVSSTVGNLRHMADMESIEAQNEQRIFSAEENEGRINSAD---KRAKNILRNK------- |
| SNAP-25 | Chicken | (140) | DARENEMDENLEQVSGIIGNLRHMALDMGNEIDTQNRQIDRIMEKLIPIKPGLMKPTSVQRCSAVVKCCSKVHFL |

|  |  | 226 | 260 |
|---|---|---|---|
| SNAP-25 | Human | (207) | ------- |
| SNAP-25 | Mouse | (207) | ------- |
| SNAP-25 | Drosophila | (213) | ------- |
| SNAP-25 | Goldfish | (204) | ------- |
| SNAP-25 | Sea Urchin | (213) | ------- |
| SNAP-25 | Chicken | (215) | LMLSQRAVPSCFYHGIYLLGLHTCTYQPHCKCCPV |

FIG. 4

```
                      1                                                                      75
VAMP-1 HUMAN    (1)   MSAPAQPPAEGTEGTAPGGGPPGPPPNMTSNRRLQQTQAQVEEVVDIIRVNVDKVLERDQKLSELDDRADALQA
VAMP-2 HUMAN    (1)   ----MSATAATAPPAAPAGEGGPPAPPPNLTSNRRLQQTQAQVDEVVDIMRVNVDKVLERDQKLSELDDRADALQA
VAMP-2 MOUSE    (1)   ----MSATAATVPPAAPAGEGGPPAPPPNLTSNRRLQQTQAQVDEVVDIMRVNVDKVLERDQKLSELDDRADALQA
VAMP Bovine     (1)   ----MSATAATAPPAAPAGEGGPPAPPPNLTSNRRLQQTQAQVDEVVDIMRVNVDKVLERDQKLSELDDRADALQA
VAMP-2 Frog     (1)   ----MSAPAAGPPAAAPGPIALQGPPHNLTSNRRLQQTQAQVDEVVDIMRVNVDKVLERDIIKLSELDDRADALQA
VAMP Sea Urchin (1)   ------------MAADPPEPQPAPSNRRLQQTQAQVDEVVDIMRVNVDKVLERDQALSMLDDRADALQQ 76                                                   123
VAMP-1 HUMAN    (75)  GASQFESSAAKLKRKYWWKNCKMMIMLGAICAIIVVIIVIYFET-------
VAMP-2 HUMAN    (73)  GASQFETSAAKLKRKYWWKNLKMMIILGVICAIILIIIVYFSS-------
VAMP-2 MOUSE    (73)  GASQFETSAAKLKRKYWWKNLKMMIILGVICAIILIIIVYFSS-------
VAMP Bovine     (73)  GASQFETSAAKLKRKYWWKNLKMMIILGVICAIILIIIVYFSS-------
VAMP-2 Frog     (71)  GASQFETSAAKLKRKYWWKJMMMIIMGVICAIILIIIVYFST-------
VAMP Sea Urchin (57)  GASQFEINAKLKRKYWWKQCKMMIILAIITVLLIIIVAIVQSQKK
```

FIG. 5

```
                                1
Syntaxin 1A human      (1)    -MKDRTQELRTAK-LSDDDDDVAVIVD-RCRFMDEFFEQVEEIRGFIDKIAENVEEVKRKHSAIIASPNPDEKTK      75
Syntaxin 1B2 human     (1)    -MKDRTQELRSAK-LSDDEEMVMVD-RDRFMDEFFEQVEEIRGCIEKLSEDVEQVKKQHSAILAAPNPDEKTK
Syntaxin 1A mouse      (1)    -MKDRTQELRTAK-LSDDDDDVLVIVD-RCRFMDEFFEQVEEIRGFLDKIAENVEEVKRKHSAILASPNPDEKTK
Syntaxin 1a drosophila (1)    MTKDRLAALHAAQSLDEEETEVAVNMDGHLSYMDFFAQVEEIRGMLDKVQTNVEEVKKKHSAILSEFQTDEKTK
Syntaxin A C. elegans  (1)    MTKDRLSAILKAASEDEQDDMHMDTG-NAQYMEFFEQVEEIRGSVDIANNVEEVKKKHSAILSNEVNDQKTK
Syntaxin Sea urchin    (1)    -MRDRLGSLKRNE-EDDVGPEVAVNMVE-SEKEMBEFFEQVEEMVNMIDKISRVDEVKKKHSDLLSAEQADEKNK 76
Syntaxin 1A human      (73)   EELEELMSDIKKTANKVRSKLRSIEQSIEQEEGLNRSSADLRIRKTQHSTLSRKFVEVMSEYNATQSDYRERCKG    150
Syntaxin 1B2 human     (72)   QELEEIMADIKKTANKVRSKLKAIEQSIEQSIEQEEGLNRSSADLRIRKTQHSTLSRKFVEVMTEYNATQSDYRERCKD
Syntaxin 1A mouse      (73)   EELEELMSDIKKTANKVRSKLRSIEQSIEQEEGLNRSSADLRIRKTQHSTLSRKFVEVMTEYNATQSDYRERCKG
Syntaxin 1a drosophila (76)   QELEDLMADIKKSNANFVRDKLKTLEQEECNRSSADLRIRKTQAKQTLADIEARHDQIMKLETSIEELHDMFMDAML
Syntaxin A C. elegans  (75)   EELEELMAVIKRAANKVRLKIENAIDHDQG-AGNADLRIRKTQAKQTLADIEARHNDIMKLESSIREELHDMFMDAML
Syntaxin Sea urchin    (73)   DELEEELMSDIKKTANKVRAKLKMMEQSIEQEESAKMNSADLRIRKTQHSTLSRKFVEVMDYNSTQDYRERCKG 151
Syntaxin 1A human      (148)  RIQRQLEITGRTTTSEELEDMLESGNPAIFASGIIMDSSISKQALSEIETRHSEIIKLENSIRELHDMFMDMAML    225
Syntaxin 1B2 human     (147)  RIQRQLEITGRTTTNEELEDMLESGKIAIFTDIKMISQWIKQALNEIETRHNEIIKLETSIRELHDMFEDMAML
Syntaxin 1A mouse      (148)  RIQRQLEITGRTTTSEELEDMLESGNPAIFSNSSVFTQGIIMETQAKQTLADIEARHDIMKLETSIEELHDMFMDMAML
Syntaxin 1a drosophila (151)  RIQRQLEITGREINDELEKMLEEGNSSVFTQGIIMETQAKQTLADIEARHDIMKLETSIEELHDMFMDMAML
Syntaxin A C. elegans  (149)  RIQRQLEIGREKQVQDELEMLESGNIYGIFTQAKQTLADIEARHDIMKLESSIRELHDMFMDMAML
Syntaxin Sea urchin    (148)  RIQRQLEITGKSITLAELEDMLESGNPAIFTSGIIMDTSGIIMDIQQAKQILRQIEARHDLIKLESSIRELHDMFMDMAML 226
Syntaxin 1A human      (223)  VESQGEMIDRIEYNVEHAVDYVERAVSDTKKAVKYQSKARRKKIMIIICCVILGIVIASTVGGIFA--           293
Syntaxin 1B2 human     (222)  VESQGEMIDRIEYNVEHSVDYVERAVSDTKKAVKYQSKARRKKIMIIICCVMLGIVLASSIGGTLGL--
Syntaxin 1A mouse      (223)  VESQGEMIDRIEYNVEHAVDYVERAVSDTKKAVKYQSKARRKKIMIIICCVILGIVIASTIGGIFG--
Syntaxin 1a drosophila (226)  VESQGEMIDRIEYNVEHAVDYVQIAEQTKKALKYQSKARRKKIMLIGLTVMGLLAASYVSSYEM--
Syntaxin A C. elegans  (224)  VESQGEMVDRIEYNVEHAKEFMIEAVAETKKAVIKYQSKARRKKFQLVTGLITIGFFLFYAKVL
Syntaxin Sea urchin    (223)  VESQGEMIDRIEYNVEQSVDYVEFLAMDTKKAVKYQSKARRKKFYIACCSVALGILVLVLIIVLA--
```

FIG. 6B

```
                                        GFP
         M   A   S   K   G   E   E   L   F   T   G   V   V   P   I   L   V   E   L   D   G
         ATGGCTAGC AAAGGAGAA GAACTCTTC ACTGGAGTT GTCCCAATT CTTGTTGAA TTAGATGGT
                                        GFP
         D   V   N   G   H   K   F   S   V   S   G   E   G   E   G   D   A   T   Y   G   K
         GATGTTAAC GGCCACAAG TTCTCTGTC AGTGGAGAG GGTGAAGGT GATGCAACA TACGGAAAA
                                        GFP
         L   T   L   K   F   I   C   T   T   G   K   L   P   V   P   W   P   T   L   V   T
         CTTACCCTG AAGTTCATC TGCACTACT GGCAAACTG CCTGTTCCA TGGCCAACA CTAGTCACT
                                        GFP
         T   L   C   Y   G   V   Q   C   F   S   R   Y   P   D   H   M   K   R   H   D   F
         ACTCTGTGC TATGGTGTT CAATGCTTT TCAAGATAC CCGGATCAT ATGAAACGG CATGACTTT
                                        GFP
         F   K   S   A   M   P   E   G   Y   V   Q   E   R   T   I   F   F   K   D   D   G
         TTCAAGAGT GCCATGCCC GAAGGTTAT GTACAGGAA AGGACCATC TTCTTCAAA GATGACGGC
                                        GFP
         N   Y   K   T   R   A   E   V   K   F   E   G   D   T   L   V   N   R   I   E   L
         AACTACAAG ACACGTGCT GAAGTCAAG TTTGAAGGT GATACCCTT GTAAATAGA ATCGAGTTA
                                        GFP
         K   G   I   D   F   K   E   D   G   N   I   L   G   H   K   L   E   Y   N   Y   N
         AAAGGTATT GACTTCAAG GAAGATGGC AACATTCTG GGACACAAA TTGGAATAC AACTATAAC
                                        GFP
         S   H   N   V   Y   I   M   A   D   K   Q   K   N   G   I   K   V   N   F   K   T
         TCACACAAT GTATACATC ATGGCAGAC AAACAAAAG AATGGAATC AAAGTGAAC TTCAAGACC
                                        GFP
         R   H   N   I   E   D   G   S   V   Q   L   A   D   H   Y   Q   Q   N   T   P   I
         CGCCACAAC ATTGAAGAT GGAAGCGTT CAACTAGCA GACCATTAT CAACAAAAT ACTCCAATT
                                        GFP
         G   D   G   P   V   L   L   P   D   N   H   Y   L   S   T   Q   S   A   L   S   K
         GGCGATGGC CCTGTCCTT TTACCAGAC AACCATTAC CTGTCCACA CAATCTGCC CTTTCGAAA
                                        GFP
         D   P   N   E   K   R   D   H   M   V   L   L   E   F   V   T   A   A   G   I   T
         GATCCCAAC GAAAAGAGA GACCACATG GTCCTTCTT GAGTTTGTA ACAGCTGCT GGGATTACA
                                                                    Linker
                    GFP
         H   G   M   D   E   L   Y   N   G   A   G   S   G   A   G   G   G   G   I   R
         CATGGCATG GATGAACTG TACAACGGC GGTGCAGGA TCCGGTGCG GGTGGCGGT GGCATCCGG
                                        SNAP25(134-206)
         R   V   T   N   D   A   R   E   N   E   M   D   E   N   L   E   Q   V   S   G   I
         AGGGTAACA AACGATGCC CGGGAAAAT GAGATGGAT GAGAACCTG GAGCAGGTG AGCGGCATC
                                        SNAP25(134-206)
         I   G   N   L   R   H   M   A   L   D   M   G   N   E   I   D   T   Q   N   R   Q
         ATCGGAAAC CTCCGCCAT ATGGCTCTA GACATGGGC AATGAGATT GACACCCAG AATCGCCAG
                                        SNAP25(134-206)
         I   D   R   I   M   E   K   A   D   S   N   K   T   R   I   D   E   A   N   Q   R
         ATCGACAGG ATCATGGAG AAGGCTGAT TCCAACAAA ACCAGAATT GATGAAGCC AACCAACGT
                                            Linker                              Cys
              SNAP25(134-206)                                6xHis Tag
         A   T   K   M   L   G   S   G   G   G   G   G   H   H   H   H   H   H   C   *
         GCAACAAAG ATGCTGGGA AGTGGTGGC GGTGGCGGC CATCACCAT CACCATCAC TGCTAA
```

FIG. 9A

**Regression Cubic Hill Plot 4 Parameters:
20ul of BCK2034 Reduced BoNT-A, 37 °C
1750 ng/ml**

Regression Cubic Hill Plot 4 Parameters:
100ul of 100:1 dilution of BCK2034, 37 °C
87.5 ng/ml

SEQUENCE LISTING

<160> NUMBER OF SEQ ID NOS: 96

<210> SEQ ID NO 1
<211> LENGTH: 206
<212> TYPE: PRT
<213> ORGANISM: Homo sapiens

<400> SEQUENCE: 1

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160
```

```
Arg His Met Ala Leu Asp Met Gly Asn Glu Ile Asp Thr Gln Asn Arg
            165                 170                 175

Gln Ile Asp Arg Ile Met Glu Lys Ala Asp Ser Asn Lys Thr Arg Ile
        180                 185                 190

Asp Glu Ala Asn Gln Arg Ala Thr Lys Met Leu Gly Ser Gly
        195                 200                 205

<210> SEQ ID NO 2
<211> LENGTH: 206
<212> TYPE: PRT
<213> ORGANISM: Mus musculus

<400> SEQUENCE: 2

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
            165                 170                 175

Gln Ile Asp Arg Ile Met Glu Lys Ala Asp Ser Asn Lys Thr Arg Ile
        180                 185                 190

Asp Glu Ala Asn Gln Arg Ala Thr Lys Met Leu Gly Ser Gly
        195                 200                 205

<210> SEQ ID NO 3
<211> LENGTH: 212
<212> TYPE: PRT
<213> ORGANISM: Drosophila sp.

<400> SEQUENCE: 3

Met Pro Ala Asp Pro Ser Glu Glu Val Ala Pro Gln Val Pro Lys Thr
1               5                   10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80
```

```
Ala Glu Lys Asn Leu Ser Gly Met Glu Lys Cys Cys Gly Ile Cys Val
            85                  90                  95

Leu Pro Cys Asn Lys Ser Gln Ser Phe Lys Glu Asp Asp Gly Thr Trp
        100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210

<210> SEQ ID NO 4
<211> LENGTH: 203
<212> TYPE: PRT
<213> ORGANISM: Carassius auratus

<400> SEQUENCE: 4

Met Ala Asp Glu Ala Asp Met Arg Asn Glu Leu Thr Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
            85                  90                  95

Gly Gly Gly Gln Ser Trp Gly Asn Asn Gln Asp Gly Val Val Ser Ser
        100                 105                 110

Gln Pro Ala Arg Val Val Asp Glu Arg Glu Gln Met Ala Ile Ser Gly
    115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200

<210> SEQ ID NO 5
<211> LENGTH: 212
<212> TYPE: PRT
```

<213> ORGANISM: Strongylcentrotas purpuratus

<400> SEQUENCE: 5

```
Met Glu Asp Gln Asn Asp Met Asn Met Arg Ser Glu Leu Glu Glu Ile
1               5                   10                  15

Gln Met Gln Ser Asn Met Gln Thr Asp Glu Ser Leu Glu Ser Thr Arg
            20                  25                  30

Arg Met Leu Gln Met Ala Glu Glu Ser Gln Asp Met Gly Ile Lys Thr
        35                  40                  45

Leu Val Met Leu Asp Glu Gln Gly Glu Gln Leu Asp Arg Ile Glu Glu
    50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
                85                  90                  95

Leu Gly Asn Phe Glu Lys Gly Asp Asp Tyr Lys Lys Thr Trp Lys Gly
            100                 105                 110

Asn Asp Asp Gly Lys Val Asn Ser His Gln Pro Met Arg Met Glu Asp
        115                 120                 125

Asp Arg Asp Gly Cys Gly Gly Asn Ala Ser Met Ile Thr Arg Ile Thr
    130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210
```

<210> SEQ ID NO 6
<211> LENGTH: 249
<212> TYPE: PRT
<213> ORGANISM: Gallus gallus

<400> SEQUENCE: 6

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
```

```
            130                 135                 140
Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Leu Ile Pro Ile Lys Pro Gly Leu
            180                 185                 190

Met Lys Pro Thr Ser Val Gln Gln Arg Cys Ser Ala Val Val Lys Cys
        195                 200                 205

Ser Lys Val His Phe Leu Leu Met Leu Ser Gln Arg Ala Val Pro Ser
    210                 215                 220

Cys Phe Tyr His Gly Ile Tyr Leu Leu Gly Leu His Thr Cys Thr Tyr
225                 230                 235                 240

Gln Pro His Cys Lys Cys Cys Pro Val
                245

<210> SEQ ID NO 7
<211> LENGTH: 118
<212> TYPE: PRT
<213> ORGANISM: Homo sapiens

<400> SEQUENCE: 7

Met Ser Ala Pro Ala Gln Pro Pro Ala Glu Gly Thr Glu Gly Thr Ala
1               5                   10                  15

Pro Gly Gly Gly Pro Pro Gly Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Phe Phe Thr
        115

<210> SEQ ID NO 8
<211> LENGTH: 116
<212> TYPE: PRT
<213> ORGANISM: Homo sapiens

<400> SEQUENCE: 8

Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
```

```
                85                  90                  95
Ile Ile Leu Gly Val Ile Cys Ala Ile Ile Leu Ile Ile Ile Ile Val
            100                 105                 110
Tyr Phe Ser Ser
        115

<210> SEQ ID NO 9
<211> LENGTH: 116
<212> TYPE: PRT
<213> ORGANISM: Mus musculus

<400> SEQUENCE: 9

Met Ser Ala Thr Ala Ala Thr Val Pro Pro Ala Ala Pro Ala Gly Glu
1               5                   10                  15
Gly Gly Pro Pro Ala Pro Pro Pro Asn Leu Thr Ser Asn Arg Arg Leu
            20                  25                  30
Gln Gln Thr Gln Ala Gln Val Asp Glu Val Val Asp Ile Met Arg Val
        35                  40                  45
Asn Val Asp Lys Val Leu Glu Arg Asp Gln Lys Leu Ser Glu Leu Asp
    50                  55                  60
Asp Arg Ala Asp Ala Leu Gln Ala Gly Ala Ser Gln Phe Glu Thr Ser
65                  70                  75                  80
Ala Ala Lys Leu Lys Arg Lys Tyr Trp Trp Lys Asn Leu Lys Met Met
                85                  90                  95
Ile Ile Leu Gly Val Ile Cys Ala Ile Ile Leu Ile Ile Ile Ile Val
            100                 105                 110
Tyr Phe Ser Thr
        115

<210> SEQ ID NO 10
<211> LENGTH: 116
<212> TYPE: PRT
<213> ORGANISM: Bos taurus

<400> SEQUENCE: 10

Met Ser Ala Thr Ala Ala Thr Ala Pro Pro Ala Ala Pro Ala Gly Glu
1               5                   10                  15
Gly Gly Pro Pro Ala Pro Pro Pro Asn Leu Thr Ser Asn Arg Arg Leu
            20                  25                  30
Gln Gln Thr Gln Ala Gln Val Asp Glu Val Val Asp Ile Met Arg Val
        35                  40                  45
Asn Val Asp Lys Val Leu Glu Arg Asp Gln Lys Leu Ser Glu Leu Asp
    50                  55                  60
Asp Arg Ala Asp Ala Leu Gln Ala Gly Ala Ser Gln Phe Glu Thr Ser
65                  70                  75                  80
Ala Ala Lys Leu Lys Arg Lys Tyr Trp Trp Lys Asn Leu Lys Met Met
                85                  90                  95
Ile Ile Leu Gly Val Ile Cys Ala Ile Ile Leu Ile Ile Ile Ile Val
            100                 105                 110
Tyr Phe Ser Ser
        115

<210> SEQ ID NO 11
<211> LENGTH: 114
<212> TYPE: PRT
<213> ORGANISM: Xenopus laevis

<400> SEQUENCE: 11
```

```
Met Ser Ala Pro Ala Ala Gly Pro Pro Ala Ala Pro Gly Asp Gly
1               5                   10                  15

Ala Pro Gln Gly Pro Pro Asn Leu Thr Ser Asn Arg Arg Leu Gln Gln
            20                  25                  30

Thr Gln Ala Gln Val Asp Glu Val Val Asp Ile Met Arg Val Asn Val
        35                  40                  45

Asp Lys Val Leu Glu Arg Asp Thr Lys Leu Ser Glu Leu Asp Asp Arg
    50                  55                  60

Ala Asp Ala Leu Gln Ala Gly Ala Ser Gln Phe Glu Thr Ser Ala Ala
65                  70                  75                  80

Lys Leu Lys Arg Lys Tyr Trp Trp Lys Asn Met Lys Met Met Ile Ile
                85                  90                  95

Met Gly Val Ile Cys Ala Ile Ile Leu Ile Ile Ile Val Tyr Phe
            100                 105                 110

Ser Thr

<210> SEQ ID NO 12
<211> LENGTH: 104
<212> TYPE: PRT
<213> ORGANISM: Strongylocentrotus purpuratus

<400> SEQUENCE: 12

Met Ala Ala Pro Pro Pro Gln Pro Ala Pro Ser Asn Lys Arg Leu
1               5                   10                  15

Gln Gln Thr Gln Ala Gln Val Asp Glu Val Val Asp Ile Met Arg Val
            20                  25                  30

Asn Val Asp Lys Val Leu Glu Arg Asp Gln Ala Leu Ser Val Leu Asp
        35                  40                  45

Asp Arg Ala Asp Ala Leu Gln Gln Gly Ala Ser Gln Phe Glu Thr Asn
    50                  55                  60

Ala Gly Lys Leu Lys Arg Lys Tyr Trp Trp Lys Asn Cys Lys Met Met
65                  70                  75                  80

Ile Ile Leu Ala Ile Ile Ile Val Ile Leu Ile Ile Ile Val
                85                  90                  95

Ala Ile Val Gln Ser Gln Lys Lys
            100

<210> SEQ ID NO 13
<211> LENGTH: 288
<212> TYPE: PRT
<213> ORGANISM: Homo sapiens

<400> SEQUENCE: 13

Met Lys Asp Arg Thr Gln Glu Leu Arg Thr Ala Lys Asp Ser Asp Asp
1               5                   10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95
```

```
Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Gly Ile Phe Ala
        275                 280                 285

<210> SEQ ID NO 14
<211> LENGTH: 288
<212> TYPE: PRT
<213> ORGANISM: Homo sapiens

<400> SEQUENCE: 14

Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190
```

```
Glu Ile Glu Thr Arg His Asn Glu Ile Ile Lys Leu Glu Thr Ser Ile
            195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
            275                 280                 285

<210> SEQ ID NO 15
<211> LENGTH: 288
<212> TYPE: PRT
<213> ORGANISM: Mus musculus

<400> SEQUENCE: 15

Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Thr Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Ile Ile Ala Ser Thr Ile Gly Gly Ile Phe Gly
```

```
                    275                 280                 285

<210> SEQ ID NO 16
<211> LENGTH: 291
<212> TYPE: PRT
<213> ORGANISM: Drosophila sp.

<400> SEQUENCE: 16

Met Thr Lys Asp Arg Leu Ala Ala Leu His Ala Ala Gln Ser Asp Asp
1               5                  10                  15

Glu Glu Glu Thr Glu Val Ala Val Asn Val Asp Gly His Asp Ser Tyr
            20                  25                  30

Met Asp Asp Phe Phe Ala Gln Val Glu Glu Ile Arg Gly Met Ile Asp
        35                  40                  45

Lys Val Gln Asp Asn Val Glu Glu Val Lys Lys His Ser Ala Ile
    50                  55                  60

Leu Ser Ala Pro Gln Thr Asp Glu Lys Thr Lys Gln Glu Leu Glu Asp
65                  70                  75                  80

Leu Met Ala Asp Ile Lys Lys Asn Ala Asn Arg Val Arg Gly Lys Leu
                85                  90                  95

Lys Gly Ile Glu Gln Asn Ile Glu Gln Glu Gln Gln Asn Lys Ser
            100                 105                 110

Ser Ala Asp Leu Arg Ile Arg Lys Thr Gln His Ser Thr Leu Ser Arg
        115                 120                 125

Lys Phe Val Glu Val Met Thr Glu Tyr Asn Arg Thr Gln Thr Asp Tyr
    130                 135                 140

Arg Glu Arg Cys Lys Gly Arg Ile Gln Arg Gln Leu Glu Ile Thr Gly
145                 150                 155                 160

Arg Pro Thr Asn Asp Asp Glu Leu Glu Lys Met Leu Glu Glu Gly Asn
                165                 170                 175

Ser Ser Val Phe Thr Gln Gly Ile Ile Met Glu Thr Gln Gln Ala Lys
            180                 185                 190

Gln Thr Leu Ala Asp Ile Glu Ala Arg His Gln Asp Ile Met Lys Leu
        195                 200                 205

Glu Thr Ser Ile Lys Glu Leu His Asp Met Phe Met Asp Met Ala Met
    210                 215                 220

Leu Val Glu Ser Gln Gly Glu Met Ile Asp Arg Ile Glu Tyr His Val
225                 230                 235                 240

Glu His Ala Met Asp Tyr Val Gln Thr Ala Thr Gln Asp Thr Lys Lys
                245                 250                 255

Ala Leu Lys Tyr Gln Ser Lys Ala Arg Arg Lys Lys Ile Met Ile Leu
            260                 265                 270

Ile Cys Leu Thr Val Leu Gly Ile Leu Ala Ala Ser Tyr Val Ser Ser
        275                 280                 285

Tyr Phe Met
    290

<210> SEQ ID NO 17
<211> LENGTH: 291
<212> TYPE: PRT
<213> ORGANISM: C. elegans

<400> SEQUENCE: 17

Met Thr Lys Asp Arg Leu Ser Ala Leu Lys Ala Ala Gln Ser Glu Asp
1               5                  10                  15

Glu Gln Asp Asp Asp Met His Met Asp Thr Gly Asn Ala Gln Tyr Met
```

```
                20                  25                  30
Glu Glu Phe Phe Glu Gln Val Glu Ile Arg Gly Ser Val Asp Ile
     35                  40                  45
Ile Ala Asn Asn Val Glu Glu Val Lys Lys Lys His Ser Ala Ile Leu
 50                  55                  60
Ser Asn Pro Val Asn Asp Gln Lys Thr Lys Glu Glu Leu Asp Glu Leu
65                  70                  75                  80
Met Ala Val Ile Lys Arg Ala Ala Asn Lys Val Arg Gly Lys Leu Lys
                 85                  90                  95
Leu Ile Glu Asn Ala Ile Asp His Asp Glu Gln Gly Ala Gly Asn Ala
                100                 105                 110
Asp Leu Arg Ile Arg Lys Thr Gln His Ser Thr Leu Ser Arg Arg Phe
            115                 120                 125
Val Glu Val Met Thr Asp Tyr Asn Lys Thr Gln Thr Asp Tyr Arg Glu
            130                 135                 140
Arg Cys Lys Gly Arg Ile Gln Arg Gln Leu Asp Ile Ala Gly Lys Gln
145                 150                 155                 160
Val Gly Asp Glu Asp Leu Glu Glu Met Ile Glu Ser Gly Asn Pro Gly
                165                 170                 175
Val Phe Thr Gln Gly Ile Ile Thr Asp Thr Gln Gln Ala Lys Gln Thr
            180                 185                 190
Leu Ala Asp Ile Glu Ala Arg His Asn Asp Ile Met Lys Leu Glu Ser
            195                 200                 205
Ser Ile Arg Glu Leu His Asp Met Phe Met Asp Met Ala Met Leu Val
 210                 215                 220
Glu Ser Gln Gly Glu Met Val Asp Arg Ile Glu Tyr Asn Val Glu His
225                 230                 235                 240
Ala Lys Glu Phe Val Asp Arg Ala Val Ala Asp Thr Lys Lys Ala Val
                245                 250                 255
Gln Tyr Gln Ser Lys Ala Arg Arg Lys Lys Ile Cys Ile Leu Val Thr
            260                 265                 270
Gly Val Ile Leu Ile Thr Gly Leu Ile Ile Phe Ile Leu Phe Tyr Ala
       275                 280                 285
Lys Val Leu
    290

<210> SEQ ID NO 18
<211> LENGTH: 288
<212> TYPE: PRT
<213> ORGANISM: Strongylocentrotus purpuratus

<400> SEQUENCE: 18

Met Arg Asp Arg Leu Gly Ser Leu Lys Arg Asn Glu Glu Asp Asp Val
1               5                   10                  15
Gly Pro Glu Val Ala Val Asn Val Glu Ser Glu Lys Phe Met Glu Glu
                 20                  25                  30
Phe Phe Glu Gln Val Glu Glu Val Arg Asn Asn Ile Asp Lys Ile Ser
     35                  40                  45
Lys Asn Val Asp Glu Val Lys Lys Lys His Ser Asp Ile Leu Ser Ala
 50                  55                  60
Pro Gln Ala Asp Glu Lys Val Lys Asp Glu Leu Glu Glu Leu Met Ser
65                  70                  75                  80
Asp Ile Lys Lys Thr Ala Asn Lys Val Arg Ala Lys Leu Lys Met Met
                 85                  90                  95
```

```
Glu Gln Ser Ile Glu Gln Glu Ser Ala Lys Met Asn Ser Ala Asp
        100                 105                 110

Val Arg Ile Arg Lys Thr Gln His Ser Thr Leu Ser Arg Lys Phe Val
        115                 120                 125

Glu Val Met Thr Asp Tyr Asn Ser Thr Gln Thr Asp Tyr Arg Glu Arg
        130                 135                 140

Cys Lys Gly Arg Ile Gln Arg Gln Leu Glu Ile Thr Gly Lys Ser Thr
145                 150                 155                 160

Thr Asp Ala Glu Leu Glu Asp Met Leu Glu Ser Gly Asn Pro Ala Ile
                165                 170                 175

Phe Thr Ser Gly Ile Ile Met Asp Thr Gln Gln Ala Lys Gln Thr Leu
                180                 185                 190

Arg Asp Ile Glu Ala Arg His Asn Asp Ile Ile Lys Leu Glu Ser Ser
            195                 200                 205

Ile Arg Glu Leu His Asp Met Phe Met Asp Met Ala Met Leu Val Glu
        210                 215                 220

Ser Gln Gly Glu Met Ile Asp Arg Ile Glu Tyr Asn Val Glu Gln Ser
225                 230                 235                 240

Val Asp Tyr Val Glu Thr Ala Lys Met Asp Thr Lys Lys Ala Val Lys
                245                 250                 255

Tyr Gln Ser Lys Ala Arg Arg Lys Lys Phe Tyr Ile Ala Ile Cys Cys
        260                 265                 270

Gly Val Ala Leu Gly Ile Leu Val Leu Val Leu Ile Ile Val Leu Ala
        275                 280                 285

<210> SEQ ID NO 19
<211> LENGTH: 1005
<212> TYPE: DNA
<213> ORGANISM: Artificial Sequence
<220> FEATURE:
<223> OTHER INFORMATION: Plasmid pQPIGFP-SNAP25
<220> FEATURE:
<221> NAME/KEY: CDS
<222> LOCATION: (1)...(1005)

<400> SEQUENCE: 19 atg gct agc aaa gga gaa gaa ctc ttc act gga gtt gtc cca att ctt      48
Met Ala Ser Lys Gly Glu Glu Leu Phe Thr Gly Val Val Pro Ile Leu
1               5                   10                  15 gtt gaa tta gat ggt gat gtt aac ggc cac aag ttc tct gtc agt gga      96
Val Glu Leu Asp Gly Asp Val Asn Gly His Lys Phe Ser Val Ser Gly
            20                  25                  30 gag ggt gaa ggt gat gca aca tac gga aaa ctt acc ctg aag ttc atc     144
Glu Gly Glu Gly Asp Ala Thr Tyr Gly Lys Leu Thr Leu Lys Phe Ile
        35                  40                  45 tgc act act ggc aaa ctg cct gtt cca tgg cca aca cta gtc act act     192
Cys Thr Thr Gly Lys Leu Pro Val Pro Trp Pro Thr Leu Val Thr Thr
50                  55                  60 ctg tgc tat ggt gtt caa tgc ttt tca aga tac ccg gat cat atg aaa     240
Leu Cys Tyr Gly Val Gln Cys Phe Ser Arg Tyr Pro Asp His Met Lys
65                  70                  75                  80 cgg cat gac ttt ttc aag agt gcc atg ccc gaa ggt tat gta cag gaa     288
Arg His Asp Phe Phe Lys Ser Ala Met Pro Glu Gly Tyr Val Gln Glu
                85                  90                  95 agg acc atc ttc ttc aaa gat gac ggc aac tac aag aca cgt gct gaa     336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt     384
Val Lys Phe Glu Gly Asp Thr Leu Val Asn Arg Ile Glu Leu Lys Gly
```

```
            115                 120                 125
att gac ttc aag gaa gat ggc aac att ctg gga cac aaa ttg gaa tac      432
Ile Asp Phe Lys Glu Asp Gly Asn Ile Leu Gly His Lys Leu Glu Tyr
    130                 135                 140 aac tat aac tca cac aat gta tac atc atg gca gac aaa caa aag aat      480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc      528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc      576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt      624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt      672
Ser Lys Asp Pro Asn Glu Lys Arg Asp His Met Val Leu Leu Glu Phe
    210                 215                 220 gta aca gct gct ggg att aca cat ggc atg gat gaa ctg tac aac ggc      720
Val Thr Ala Ala Gly Ile Thr His Gly Met Asp Glu Leu Tyr Asn Gly
225                 230                 235                 240 ggt gca gga tcc ggt gcg ggt ggc ggt ggc atc cgg agg gta aca aac      768
Gly Ala Gly Ser Gly Ala Gly Gly Gly Gly Ile Arg Arg Val Thr Asn
                245                 250                 255 gat gcc cgg gaa aat gag atg gat gag aac ctg gag cag gtg agc ggc      816
Asp Ala Arg Glu Asn Glu Met Asp Glu Asn Leu Glu Gln Val Ser Gly
            260                 265                 270 atc atc gga aac ctc cgc cat atg gct cta gac atg ggc aat gag att      864
Ile Ile Gly Asn Leu Arg His Met Ala Leu Asp Met Gly Asn Glu Ile
        275                 280                 285 gac acc cag aat cgc cag atc gac agg atc atg gag aag gct gat tcc      912
Asp Thr Gln Asn Arg Gln Ile Asp Arg Ile Met Glu Lys Ala Asp Ser
    290                 295                 300 aac aaa acc aga att gat gaa gcc aac caa cgt gca aca aag atg ctg      960
Asn Lys Thr Arg Ile Asp Glu Ala Asn Gln Arg Ala Thr Lys Met Leu
305                 310                 315                 320 gga agt ggt ggc ggt ggc ggc cat cac cat cac cat cac tgc taa          1005
Gly Ser Gly Gly Gly Gly Gly His His His His His His Cys *
                325                 330

<210> SEQ ID NO 20
<211> LENGTH: 334
<212> TYPE: PRT
<213> ORGANISM: Artificial Sequence
<220> FEATURE:
<223> OTHER INFORMATION: Plasmid pQBI GFP-SNAP25

<400> SEQUENCE: 20

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80
```

```
Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
           100                 105                 110

Val Lys Phe Glu Gly Asp Thr Leu Val Asn Arg Ile Glu Leu Lys Gly
       115                 120                 125

Ile Asp Phe Lys Glu Asp Gly Asn Ile Leu Gly His Lys Leu Glu Tyr
   130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
            260                 265                 270

Ile Ile Gly Asn Leu Arg His Met Ala Leu Asp Met Gly Asn Glu Ile
        275                 280                 285

Asp Thr Gln Asn Arg Gln Ile Asp Arg Ile Met Glu Lys Ala Asp Ser
    290                 295                 300

Asn Lys Thr Arg Ile Asp Glu Ala Asn Gln Arg Ala Thr Lys Met Leu
305                 310                 315                 320

Gly Ser Gly Gly Gly Gly Gly His His His His His Cys
                325                 330

<210> SEQ ID NO 21
<211> LENGTH: 5
<212> TYPE: PRT
<213> ORGANISM: Clostridium sp.

<400> SEQUENCE: 21

Gly Gly Gly Gly Ser
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic construct

<400> SEQUENCE: 22

Glu Ala Asn Gln Arg Ala Thr Lys
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic construct
```

```
<400> SEQUENCE: 23

Gly Ala Ser Gln Phe Glu Thr Ser
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic construct

<400> SEQUENCE: 24

Asp Thr Lys Lys Ala Val Lys Trp
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic construct

<400> SEQUENCE: 25

Arg Asp Gln Lys Leu Ser Glu Leu
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic construct

<400> SEQUENCE: 26

Gln Ile Asp Arg Ile Met Glu Lys
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic construct

<400> SEQUENCE: 27

Glu Arg Asp Gln Lys Leu Ser Glu
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic construct

<400> SEQUENCE: 28

Glu Thr Ser Ala Ala Lys Leu Lys
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic construct
```

```
<400> SEQUENCE: 29

Gly Ala Ser Gln Phe Glu Thr Ser
1               5

<210> SEQ ID NO 30
<211> LENGTH: 13
<212> TYPE: PRT
<213> ORGANISM: Homo sapiens

<400> SEQUENCE: 30

Thr Arg Ile Asp Glu Ala Asn Gln Arg Ala Thr Lys Met
1               5                   10

<210> SEQ ID NO 31
<211> LENGTH: 15
<212> TYPE: PRT
<213> ORGANISM: Homo sapiens

<400> SEQUENCE: 31

Ser Asn Lys Thr Arg Ile Asp Glu Ala Asn Gln Arg Ala Thr Lys
1               5                   10                  15

<210> SEQ ID NO 32
<211> LENGTH: 16
<212> TYPE: PRT
<213> ORGANISM: Homo sapiens

<400> SEQUENCE: 32

Ser Asn Lys Thr Arg Ile Asp Glu Ala Asn Gln Arg Ala Thr Lys Met
1               5                   10                  15

<210> SEQ ID NO 33
<211> LENGTH: 17
<212> TYPE: PRT
<213> ORGANISM: Homo sapiens

<400> SEQUENCE: 33

Ser Asn Lys Thr Arg Ile Asp Glu Ala Asn Gln Arg Ala Thr Lys Met
1               5                   10                  15

Leu

<210> SEQ ID NO 34
<211> LENGTH: 17
<212> TYPE: PRT
<213> ORGANISM: Homo sapiens

<400> SEQUENCE: 34

Asp Ser Asn Lys Thr Arg Ile Asp Glu Ala Asn Gln Arg Ala Thr Lys
1               5                   10                  15

Met

<210> SEQ ID NO 35
<211> LENGTH: 18
<212> TYPE: PRT
<213> ORGANISM: Homo sapiens

<400> SEQUENCE: 35

Asp Ser Asn Lys Thr Arg Ile Asp Glu Ala Asn Gln Arg Ala Thr Lys
1               5                   10                  15

Met Leu

<210> SEQ ID NO 36
```

-continued

```
<211> LENGTH: 33
<212> TYPE: PRT
<213> ORGANISM: Mus musculus

<400> SEQUENCE: 36

Gln Asn Arg Gln Ile Asp Arg Ile Met Glu Lys Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 37
<211> LENGTH: 32
<212> TYPE: PRT
<213> ORGANISM: Homo sapiens

<400> SEQUENCE: 37

Gln Asn Pro Gln Ile Lys Arg Ile Thr Asp Lys Ala Asp Thr Asn Arg
1               5                   10                  15

Asp Arg Ile Asp Ile Ala Asn Ala Arg Ala Lys Lys Leu Ile Asp Ser
            20                  25                  30

<210> SEQ ID NO 38
<211> LENGTH: 32
<212> TYPE: PRT
<213> ORGANISM: Mus musculus

<400> SEQUENCE: 38

Gln Asn Gln Gln Ile Gln Lys Ile Thr Glu Lys Ala Asp Thr Asn Lys
1               5                   10                  15

Asn Arg Ile Asp Ile Ala Asn Thr Arg Ala Lys Lys Leu Ile Asp Ser
            20                  25                  30

<210> SEQ ID NO 39
<211> LENGTH: 34
<212> TYPE: PRT
<213> ORGANISM: Gallus gallus

<400> SEQUENCE: 39

Gln Asn Arg Gln Ile Asp Arg Ile Met Glu Lys Leu Ile Pro Ile Lys
1               5                   10                  15

Pro Gly Leu Met Lys Pro Thr Ser Val Gln Gln Arg Cys Ser Ala Val
            20                  25                  30

Val Lys

<210> SEQ ID NO 40
<211> LENGTH: 33
<212> TYPE: PRT
<213> ORGANISM: Carassius auratus

<400> SEQUENCE: 40

Gln Asn Arg Gln Ile Asp Arg Ile Met Asp Met Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 41
<211> LENGTH: 33
<212> TYPE: PRT
<213> ORGANISM: Carassius auratus
```

```
<400> SEQUENCE: 41

Gln Asn Arg Gln Ile Asp Arg Ile Met Glu Lys Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 42
<211> LENGTH: 30
<212> TYPE: PRT
<213> ORGANISM: Torpedo sp.

<400> SEQUENCE: 42

Gln Asn Ala Gln Val Asp Arg Ile Val Val Lys Gly Asp Met Asn Lys
1               5                   10                  15

Ala Arg Ile Asp Glu Ala Asn Lys His Ala Thr Lys Met Leu
            20                  25                  30

<210> SEQ ID NO 43
<211> LENGTH: 33
<212> TYPE: PRT
<213> ORGANISM: Strongylocentrotus purpuratus

<400> SEQUENCE: 43

Gln Asn Ser Gln Val Gly Arg Ile Thr Ser Lys Ala Glu Ser Asn Glu
1               5                   10                  15

Gly Arg Ile Asn Ser Ala Asp Lys Arg Ala Lys Asn Ile Leu Arg Asn
            20                  25                  30

Lys

<210> SEQ ID NO 44
<211> LENGTH: 31
<212> TYPE: PRT
<213> ORGANISM: C. elegans

<400> SEQUENCE: 44

Gln Asn Arg Gln Leu Asp Arg Ile His Asp Lys Gln Ser Asn Glu Val
1               5                   10                  15

Arg Val Glu Ser Ala Asn Lys Arg Ala Lys Asn Leu Ile Thr Lys
            20                  25                  30

<210> SEQ ID NO 45
<211> LENGTH: 31
<212> TYPE: PRT
<213> ORGANISM: Drosophila sp.

<400> SEQUENCE: 45

Gln Asn Arg Gln Ile Asp Arg Ile Asn Arg Lys Gly Glu Ser Asn Glu
1               5                   10                  15

Ala Arg Ile Ala Val Ala Asn Gln Arg Ala His Gln Leu Leu Lys
            20                  25                  30

<210> SEQ ID NO 46
<211> LENGTH: 32
<212> TYPE: PRT
<213> ORGANISM: Hirudinida sp.

<400> SEQUENCE: 46

Gln Asn Arg Gln Val Asp Arg Ile Asn Asn Lys Met Thr Ser Asn Gln
1               5                   10                  15
```

```
Leu Arg Ile Ser Asp Ala Asn Lys Arg Ala Ser Lys Leu Leu Lys Glu
            20                  25                  30

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 17
<212> TYPE: PRT
<213> ORGANISM: Artificial Sequence
<220> FEATURE:
<223> OTHER INFORMATION: synthetic construct

<400> SEQUENCE: 50

Ser Asn Lys Thr Arg Ile Asp Glu Ala Asn Gln Arg Ala Thr Lys Ala
1               5                   10                  15

Leu

<210> SEQ ID NO 51
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 16
<223> OTHER INFORMATION: Xaa=Nle

<400> SEQUENCE: 51

Ser Asn Lys Thr Arg Ile Asp Glu Ala Asn Gln Arg Ala Thr Lys Xaa
1               5                   10                  15

Leu

<210> SEQ ID NO 52
<211> LENGTH: 17
<212> TYPE: PRT
<213> ORGANISM: Artificial Sequence
<220> FEATURE:
<223> OTHER INFORMATION: synthetic construct

<400> SEQUENCE: 52

Ser Asn Lys Thr Arg Ile Asp Glu Ala Asn Gln Arg Ala Thr Ala Met
1               5                   10                  15

Leu

<210> SEQ ID NO 53
<211> LENGTH: 17
<212> TYPE: PRT
<213> ORGANISM: Artificial Sequence
```

```
<220> FEATURE:
<223> OTHER INFORMATION: synthetic construct

<400> SEQUENCE: 53

Ser Asn Lys Thr Arg Ile Asp Glu Ala Asn Gln Arg Ala Ser Lys Met
1               5                   10                  15

Leu

<210> SEQ ID NO 54
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 14
<223> OTHER INFORMATION: Xaa=Abu

<400> SEQUENCE: 54

Ser Asn Lys Thr Arg Ile Asp Glu Ala Asn Gln Arg Ala Xaa Lys Met
1               5                   10                  15

Leu

<210> SEQ ID NO 55
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 13
<223> OTHER INFORMATION: Xaa=Abu

<400> SEQUENCE: 55

Ser Asn Lys Thr Arg Ile Asp Glu Ala Asn Gln Arg Xaa Thr Lys Met
1               5                   10                  15

Leu

<210> SEQ ID NO 56
<211> LENGTH: 17
<212> TYPE: PRT
<213> ORGANISM: Artificial Sequence
<220> FEATURE:
<223> OTHER INFORMATION: synthetic construct

<400> SEQUENCE: 56

Ser Asn Lys Thr Arg Ile Asp Glu Ala Asn Ala Arg Ala Thr Lys Met
1               5                   10                  15

Leu

<210> SEQ ID NO 57
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 11
<223> OTHER INFORMATION: Xaa=Abu

<400> SEQUENCE: 57

Ser Asn Lys Thr Arg Ile Asp Glu Ala Asn Xaa Arg Ala Thr Lys Met
1               5                   10                  15
```

Leu

<210> SEQ ID NO 58
<211> LENGTH: 17
<212> TYPE: PRT
<213> ORGANISM: Artificial Sequence
<220> FEATURE:
<223> OTHER INFORMATION: synthetic construct

<400> SEQUENCE: 58

Ser Asn Lys Thr Arg Ile Asp Glu Ala Asn Asn Arg Ala Thr Lys Met
1               5                   10                  15

Leu

<210> SEQ ID NO 59
<211> LENGTH: 17
<212> TYPE: PRT
<213> ORGANISM: Artificial Sequence
<220> FEATURE:
<223> OTHER INFORMATION: synthetic construct

<400> SEQUENCE: 59

Ser Asn Lys Thr Arg Ile Asp Glu Ala Ala Gln Arg Ala Thr Lys Met
1               5                   10                  15

Leu

<210> SEQ ID NO 60
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 9
<223> OTHER INFORMATION: Xaa=Abu

<400> SEQUENCE: 60

Ser Asn Lys Thr Arg Ile Asp Glu Xaa Asn Gln Arg Ala Thr Lys Met
1               5                   10                  15

Leu

<210> SEQ ID NO 61
<211> LENGTH: 17
<212> TYPE: PRT
<213> ORGANISM: Artificial Sequence
<220> FEATURE:
<223> OTHER INFORMATION: synthetic construct

<400> SEQUENCE: 61

Ser Asn Lys Thr Arg Ile Asp Gln Ala Asn Gln Arg Ala Thr Lys Met
1               5                   10                  15

Leu

<210> SEQ ID NO 62
<211> LENGTH: 17
<212> TYPE: PRT
<213> ORGANISM: Artificial Sequence
<220> FEATURE:
<223> OTHER INFORMATION: synthetic construct

<400> SEQUENCE: 62

Ser Asn Lys Thr Arg Ile Asn Glu Ala Asn Gln Arg Ala Thr Lys Met
1               5                   10                  15

Leu

<210> SEQ ID NO 63
<211> LENGTH: 40
<212> TYPE: PRT
<213> ORGANISM: Homo sapiens

<400> SEQUENCE: 63

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Ser Ser Ala Ala
            20                  25                  30

Lys Leu Lys Arg Lys Tyr Trp Trp
        35                  40

<210> SEQ ID NO 64
<211> LENGTH: 40
<212> TYPE: PRT
<213> ORGANISM: Bos taurus

<400> SEQUENCE: 64

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 65
<211> LENGTH: 40
<212> TYPE: PRT
<213> ORGANISM: Rattus sp.

<400> SEQUENCE: 65

Asp Lys Val Leu Glu Arg Asp Gln Lys Leu Ser Glu Leu Asp Asp Arg
1               5                   10                  15

Ala Asp Ala Leu Gln Ala Gly Ala Ser Val Phe Glu Ser Ser Ala Ala
            20                  25                  30

Lys Leu Lys Arg Lys Tyr Trp Trp
        35                  40

<210> SEQ ID NO 66
<211> LENGTH: 40
<212> TYPE: PRT
<213> ORGANISM: Rattus sp.

<400> SEQUENCE: 66

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 67
<211> LENGTH: 40
<212> TYPE: PRT
<213> ORGANISM: Rattus sp.

<400> SEQUENCE: 67

```
Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
                20                  25                  30

Lys Leu Lys Arg Lys Tyr Trp Trp
            35                  40

<210> SEQ ID NO 68
<211> LENGTH: 40
<212> TYPE: PRT
<213> ORGANISM: Rattus sp.

<400> SEQUENCE: 68

Asp Leu Val Ala Gln Arg Gly Glu Arg Leu Glu Leu Leu Ile Asp Lys
1               5                   10                  15

Thr Glu Asn Leu Val Asp Ser Ser Val Thr Phe Lys Thr Thr Ser Arg
                20                  25                  30

Asn Leu Ala Arg Ala Met Cys Met
            35                  40

<210> SEQ ID NO 69
<211> LENGTH: 32
<212> TYPE: PRT
<213> ORGANISM: Gallus gallus

<400> SEQUENCE: 69

Glu Arg Asp Gln Lys Leu Ser Glu Leu Asp Asp Arg Ala Asp Ala Leu
1               5                   10                  15

Gln Ala Gly Ala Ser Val Phe Glu Ser Ser Ala Ala Lys Leu Lys Arg
                20                  25                  30

<210> SEQ ID NO 70
<211> LENGTH: 32
<212> TYPE: PRT
<213> ORGANISM: Gallus gallus

<400> SEQUENCE: 70

Glu Arg Asp Gln Lys Leu Ser Glu Leu Asp Asp Arg Ala Asp Ala Leu
1               5                   10                  15

Gln Ala Gly Ala Ser Gln Phe Glu Thr Ser Ala Ala Lys Leu Lys Arg
                20                  25                  30

<210> SEQ ID NO 71
<211> LENGTH: 40
<212> TYPE: PRT
<213> ORGANISM: Torpedo sp.

<400> SEQUENCE: 71

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Ser Ser Ala Ala
                20                  25                  30

Lys Leu Lys Arg Lys Tyr Trp Trp
            35                  40

<210> SEQ ID NO 72
<211> LENGTH: 40
<212> TYPE: PRT
<213> ORGANISM: Strongylocentrotus purpuratus

<400> SEQUENCE: 72
```

-continued

```
Asp Lys Val Leu Asp Arg Asp Gly Ala Leu Ser Val Leu Asp Asp Arg
1               5                   10                  15

Ala Asp Ala Leu Gln Gln Gly Ala Ser Gln Phe Glu Thr Asn Ala Gly
            20                  25                  30

Lys Leu Lys Arg Lys Tyr Trp Trp
        35                  40

<210> SEQ ID NO 73
<211> LENGTH: 40
<212> TYPE: PRT
<213> ORGANISM: Aplysia sp.

<400> SEQUENCE: 73

Glu Lys Val Leu Asp Arg Asp Gln Lys Ile Ser Gln Leu Asp Asp Arg
1               5                   10                  15

Ala Glu Ala Leu Gln Ala Gly Ala Ser Gln Phe Glu Ala Ser Ala Gly
            20                  25                  30

Lys Leu Lys Arg Lys Tyr Trp Trp
        35                  40

<210> SEQ ID NO 74
<211> LENGTH: 40
<212> TYPE: PRT
<213> ORGANISM: Teuthoida sp.

<400> SEQUENCE: 74

Asp Lys Val Leu Glu Arg Asp Ser Lys Ile Ser Glu Leu Asp Asp Arg
1               5                   10                  15

Ala Asp Ala Leu Gln Ala Gly Ala Ser Gln Phe Glu Ala Ser Ala Gly
            20                  25                  30

Lys Leu Lys Arg Lys Phe Trp Trp
        35                  40

<210> SEQ ID NO 75
<211> LENGTH: 40
<212> TYPE: PRT
<213> ORGANISM: C. elegans

<400> SEQUENCE: 75

Asn Lys Val Met Glu Arg Asp Val Gln Leu Asn Ser Leu Asp His Arg
1               5                   10                  15

Ala Glu Val Leu Gln Asn Gly Ala Ser Gln Phe Gln Gln Ser Ser Arg
            20                  25                  30

Glu Leu Lys Arg Gln Tyr Trp Trp
        35                  40

<210> SEQ ID NO 76
<211> LENGTH: 40
<212> TYPE: PRT
<213> ORGANISM: Drosophila melanogaster

<400> SEQUENCE: 76

Glu Lys Val Leu Glu Arg Asp Gln Lys Leu Ser Glu Leu Gly Glu Arg
1               5                   10                  15

Ala Asp Gln Leu Glu Gly Gly Ala Ser Gln Ser Glu Gln Gln Ala Gly
            20                  25                  30

Lys Leu Lys Arg Lys Gln Trp Trp
        35                  40

<210> SEQ ID NO 77
```

```
<211> LENGTH: 40
<212> TYPE: PRT
<213> ORGANISM: Drosophila melanogaster

<400> SEQUENCE: 77

Glu Lys Val Leu Glu Arg Asp Ser Lys Leu Ser Glu Leu Asp Asp Arg
1               5                   10                  15

Ala Asp Ala Leu Gln Gln Gly Ala Ser Gln Phe Glu Gln Gln Ala Gly
            20                  25                  30

Lys Leu Lys Arg Lys Phe Trp Leu
        35                  40

<210> SEQ ID NO 78
<211> LENGTH: 39
<212> TYPE: PRT
<213> ORGANISM: Hirudinida sp.

<400> SEQUENCE: 78

Asp Lys Val Leu Glu Lys Asp Gln Lys Leu Ala Glu Leu Asp Arg Ala
1               5                   10                  15

Asp Ala Leu Gln Ala Gly Ala Ser Gln Phe Glu Ala Ser Ala Gly Lys
            20                  25                  30

Leu Lys Arg Lys Phe Trp Trp
        35

<210> SEQ ID NO 79
<211> LENGTH: 18
<212> TYPE: PRT
<213> ORGANISM: Homo sapiens

<400> SEQUENCE: 79

Glu Arg Ala Val Ser Asp Thr Lys Lys Ala Val Lys Tyr Gln Ser Lys
1               5                   10                  15

Ala Arg

<210> SEQ ID NO 80
<211> LENGTH: 18
<212> TYPE: PRT
<213> ORGANISM: Bos taurus

<400> SEQUENCE: 80

Glu Arg Ala Val Ser Asp Thr Lys Lys Ala Val Lys Tyr Gln Ser Lys
1               5                   10                  15

Ala Arg

<210> SEQ ID NO 81
<211> LENGTH: 18
<212> TYPE: PRT
<213> ORGANISM: Rattus rattus

<400> SEQUENCE: 81

Glu His Ala Lys Glu Glu Thr Lys Lys Ala Ile Lys Tyr Gln Ser Lys
1               5                   10                  15

Ala Arg

<210> SEQ ID NO 82
<211> LENGTH: 18
<212> TYPE: PRT
<213> ORGANISM: Rattus rattus

<400> SEQUENCE: 82
```

```
Glu Lys Ala Arg Asp Glu Thr Arg Lys Ala Met Lys Tyr Gln Gly Gly
1               5                   10                  15

Ala Arg
```

<210> SEQ ID NO 83
<211> LENGTH: 18
<212> TYPE: PRT
<213> ORGANISM: Rattus rattus

<400> SEQUENCE: 83

```
Glu Arg Gly Gln Glu His Val Lys Ile Ala Leu Glu Asn Gln Lys Lys
1               5                   10                  15

Ala Arg
```

<210> SEQ ID NO 84
<211> LENGTH: 18
<212> TYPE: PRT
<213> ORGANISM: Gallus gallus

<400> SEQUENCE: 84

```
Val Pro Glu Val Phe Val Thr Lys Ser Ala Val Met Tyr Gln Cys Lys
1               5                   10                  15

Ser Arg
```

<210> SEQ ID NO 85
<211> LENGTH: 18
<212> TYPE: PRT
<213> ORGANISM: Strongylocentrotus purpuratus

<400> SEQUENCE: 85

```
Val Arg Arg Gln Asn Asp Thr Lys Lys Ala Val Lys Tyr Gln Ser Lys
1               5                   10                  15

Ala Arg
```

<210> SEQ ID NO 86
<211> LENGTH: 18
<212> TYPE: PRT
<213> ORGANISM: Aplysia sp.

<400> SEQUENCE: 86

```
Glu Thr Ala Lys Met Asp Thr Lys Lys Ala Val Lys Tyr Gln Ser Lys
1               5                   10                  15

Ala Arg
```

<210> SEQ ID NO 87
<211> LENGTH: 18
<212> TYPE: PRT
<213> ORGANISM: Teuthoida sp.

<400> SEQUENCE: 87

```
Glu Thr Ala Lys Val Asp Thr Lys Lys Ala Val Lys Tyr Gln Ser Lys
1               5                   10                  15

Ala Arg
```

<210> SEQ ID NO 88
<211> LENGTH: 18
<212> TYPE: PRT
<213> ORGANISM: Drosophila melanogaster

<400> SEQUENCE: 88

```
Gln Thr Ala Thr Gln Asp Thr Lys Lys Ala Leu Lys Tyr Gln Ser Lys
```

-continued

```
                1               5                  10                 15

Ala Arg

<210> SEQ ID NO 89
<211> LENGTH: 18
<212> TYPE: PRT
<213> ORGANISM: Hirudinida sp.

<400> SEQUENCE: 89

Glu Thr Ala Ala Ala Asp Thr Lys Lys Ala Met Lys Tyr Gln Ser Ala
1               5                   10                  15

Ala Arg

<210> SEQ ID NO 90
<211> LENGTH: 116
<212> TYPE: PRT
<213> ORGANISM: Rattus sp.

<400> SEQUENCE: 90

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
        115

<210> SEQ ID NO 91
<211> LENGTH: 36
<212> TYPE: DNA
<213> ORGANISM: Artificial Sequence
<220> FEATURE:
<223> OTHER INFORMATION: primer

<400> SEQUENCE: 91
gctagatctc gagttaacca cttcccagca tctttg                              36

<210> SEQ ID NO 92
<211> LENGTH: 24
<212> TYPE: DNA
<213> ORGANISM: Artificial Sequence
<220> FEATURE:
<223> OTHER INFORMATION: primer

<400> SEQUENCE: 92
atccggaggg taacaaacga tgcc                                           24

<210> SEQ ID NO 93
<211> LENGTH: 60
<212> TYPE: DNA
<213> ORGANISM: Artificial Sequence
<220> FEATURE:
```

-continued

```
<223> OTHER INFORMATION: primer

<400> SEQUENCE: 93
cgaattccgc gggccaccat gggaggagga ctgaacgaca tcttcgaggc tcaaaagatc      60

<210> SEQ ID NO 94
<211> LENGTH: 79
<212> TYPE: DNA
<213> ORGANISM: Artificial Sequence
<220> FEATURE:
<223> OTHER INFORMATION: primer

<400> SEQUENCE: 94
tcgtttgtta ccctccggat atgatgatga tgatgatgat gatgggatcc atgccactcg      60 atctttgag cctcgaaga                                                   79

<210> SEQ ID NO 95
<211> LENGTH: 30
<212> TYPE: DNA
<213> ORGANISM: Artificial Sequence
<220> FEATURE:
<223> OTHER INFORMATION: primer

<400> SEQUENCE: 95
cgaagatctg gaggactgaa cgacatcttc                                      30

<210> SEQ ID NO 96
<211> LENGTH: 34
<212> TYPE: DNA
<213> ORGANISM: Artificial Sequence
<220> FEATURE:
<223> OTHER INFORMATION: primer

<400> SEQUENCE: 96
gatggtgatg gtgatgacag ccgccaccgc cacc                                 34
```

FLUORESCENCE POLARIZATION ASSAYS FOR DETERMINING CLOSTRIDIAL TOXIN ACTIVITY

This application is a divisional and claims priority pursuant to 35 U.S.C. §120 to U.S. patent application Ser. No. 10/948,097, filed Sep. 22, 2004, now U.S. Pat. No. 7,399,607 which is hereby incorporated by reference in its entirety.

The present invention relates generally to protease assays, and more specifically, to methods for determining the presence or activity of clostridial toxins such as botulinum toxins and tetanus toxins using fluorescence polarization.

The neuroparalytic syndrome of tetanus and the rare but potentially fatal disease, botulism, are caused by neurotoxins produced by bacteria of the genus *Clostridium*. These clostridial neurotoxins are highly potent and specific poisons of neural cells, with the human lethal dose of the botulinum toxins on the order of nanograms. Thus, the presence of even minute levels of botulinum toxins in foodstuffs represents a public health hazard that must be avoided through rigorous testing.

However, in spite of their potentially deleterious effects, low controlled doses of botulinum neurotoxins have been successfully used as therapeutics and for some cosmetic applications. In particular, botulinum toxins have been used in the therapeutic management of a variety of focal and segmental dystonias, strabismus, and other conditions in which a reversible depression of cholinergic nerve terminal activity is desired. Established therapeutic uses of botulinum neurotoxins in humans include, without limitation, treatment of blepharospasm, hemifacial spasm, laryngeal dysphonia, focal hyperhidrosis, hypersalivation, oromandibular dystonia, cervical dystonia, torticollis, strabismus, limbs dystonia, occupational cramps and myokymia (Rossetto et al., *Toxicon* 39:27-41 (2001)). As an example, intramuscular injection of spastic tissue with small quantities of botulinum neurotoxin A has been used effectively to treat spasticity due to brain injury, spinal cord injury, stroke, multiple sclerosis and cerebral palsy. Additional possible clinical uses of clostridial neurotoxins are currently being investigated.

Given the potential danger associated with small quantities of botulinum toxins in foodstuffs and the need to prepare accurate pharmaceutical formulations, assays for botulinum neurotoxins presently are employed in the food and pharmaceutical industries. The food industry requires assays for the botulinum neurotoxins to validate new food packaging methods and to ensure food safety. The growing clinical use of the botulinum toxins necessitates accurate assays for botulinum neurotoxin activity for product formulation as well as quality control. In both industries, a mouse lethality test currently is the only acceptable assay for botulinum neurotoxin potency.

Unfortunately, the mouse lethality assay suffers from several drawbacks: cost due to the large numbers of laboratory animals required; lack of specificity; potential for inaccuracy unless large animal groups are used; and sacrifice of animal life. Thus, there is a need for new methods based on convenient synthetic substrates that can complement and reduce the need for the mouse lethality assay. The present invention satisfies this need by providing novel assays for determining the presence or activity of a clostridial toxin and provides related advantages as well.

The present invention provides a method of determining the presence or activity of a clostridial toxin by (a) treating with a sample, under conditions suitable for clostridial toxin protease activity, a clostridial toxin substrate which includes a fluorophore; a bulking group; and a clostridial toxin recognition sequence containing a cleavage site that intervenes between the fluorophore and the bulking group; (b) exciting the fluorophore with plane polarized light; and (c) determining fluorescence polarization of the treated substrate relative to a control substrate, where a change in fluorescence polarization of the treated substrate as compared to fluorescence polarization of the control substrate is indicative of the presence or activity of the clostridial toxin.

Further provided herein is a method of determining the presence or activity of a clostridial toxin by (a) treating with a sample, under conditions suitable for clostridial toxin protease activity, a clostridial toxin substrate containing (i) a donor fluorophore; (ii) an acceptor having an absorbance spectrum overlapping the emission spectrum of the donor fluorophore; and (iii) a clostridial toxin recognition sequence containing a cleavage site, where the cleavage site intervenes between the donor fluorophore and the acceptor and where, under the appropriate conditions, resonance energy transfer is exhibited between the donor fluorophore and the acceptor; (b) exciting the donor fluorophore with plane polarized light; and (c) determining fluorescence polarization of the treated substrate relative to a control substrate, where a change in fluorescence polarization of the treated substrate as compared to fluorescence polarization of the control substrate is indicative of the presence or activity of the clostridial toxin.

BRIEF DESCRIPTION OF THE DRAWINGS

FIG. 1 shows a schematic of the four steps required for tetanus and botulinum toxin activity in central and peripheral neurons.

FIG. 3 shows an alignment of various SNAP-25 proteins. Human SNAP-25 (SEQ ID NO: 1; GenBank accession g4507099; see, also, related human SNAP-25 sequence g2135800); mouse SNAP-25 (SEQ ID NO: 2; GenBank accession G6755588); *Drosophila* SNAP-25 (SEQ ID NO: 3; GenBank accession g548941); goldfish SNAP-25 (SEQ ID NO: 4; GenBank accession g2133923); sea urchin SNAP-25 (SEQ ID NO: 5; GenBank accession g2707818) and chicken SNAP-25 (SEQ ID NO: 6; GenBank accession g481202) are depicted.

FIG. 4 shows an alignment of various VAMP proteins. Human VAMP-1 (SEQ ID NO: 7; GenBank accession g135093); human VAMP-2 (SEQ ID NO: 8; GenBank accession g135094); mouse VAMP-2 (SEQ ID NO: 9; GenBank accession g2501081); bovine VAMP (SEQ ID NO: 10; GenBank accession g89782); frog VAMP (SEQ ID NO: 11; GenBank accession g6094391); and sea urchin VAMP (SEQ ID NO: 12; GenBank accession g5031415) are depicted.

FIG. 5 shows an alignment of various syntaxin proteins. Human syntaxin 1A (SEQ ID NO: 13; GenBank accession g15079184), human syntaxin 1B2 (SEQ ID NO: 14; GenBank accession g15072437), mouse syntaxin 1A (SEQ ID NO: 15; GenBank accession g15011853), *Drosophila* syntaxin 1A (SEQ ID NO: 16; GenBank accession g2501095); *C. elegans* syntaxin A (SEQ ID NO: 17; GenBank accession g7511662) and sea urchin syntaxin (SEQ ID NO: 18; GenBank accession g13310402) are depicted.

DETAILED DESCRIPTION

Figure 2:
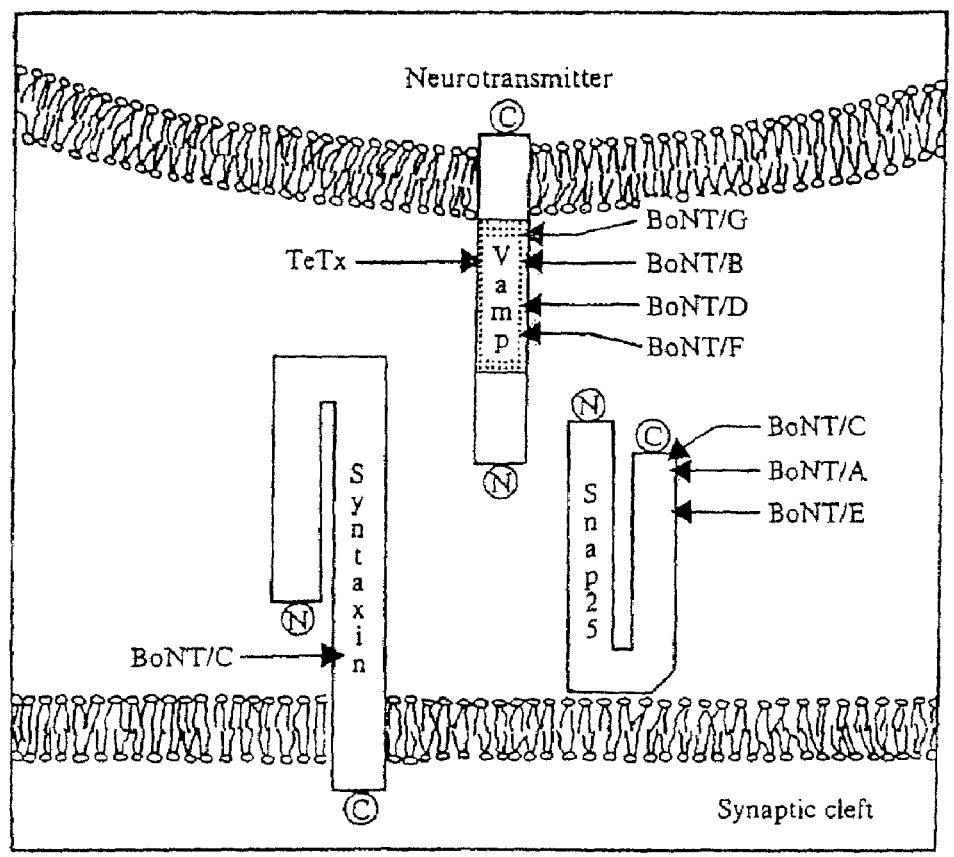
FIG. 2 shows the subcellular localization and sites of cleavage of SNAP-25, VAMP and syntaxin. VAMP is bound to synaptic vesicle membrane, whereas SNAP-25 and syntaxin are bound to the target plasma membrane. BoNT/A and /E cleave SNAP-25 close to the carboxy-terminus, releasing nine or 26 residues, respectively. BoNT/B, /D, /F, /G and TeNT act on the conserved central portion of VAMP (dotted) and release the amino-terminal portion of VAMP into the cytosol. BoNT/C1 cleaves SNAP-25 close to the carboxy-terminus as well as cleaving syntaxin at a single site near the cytosolic membrane surface. The action of BoNT/B, /C1, /D, /F, /G and TeNT results in release of a large portion of the cytosolic domain of VAMP or syntaxin, while only a small portion of SNAP-25 is released by selective proteolysis of BoNT/A, /C1 or /E.
Figure 6A:
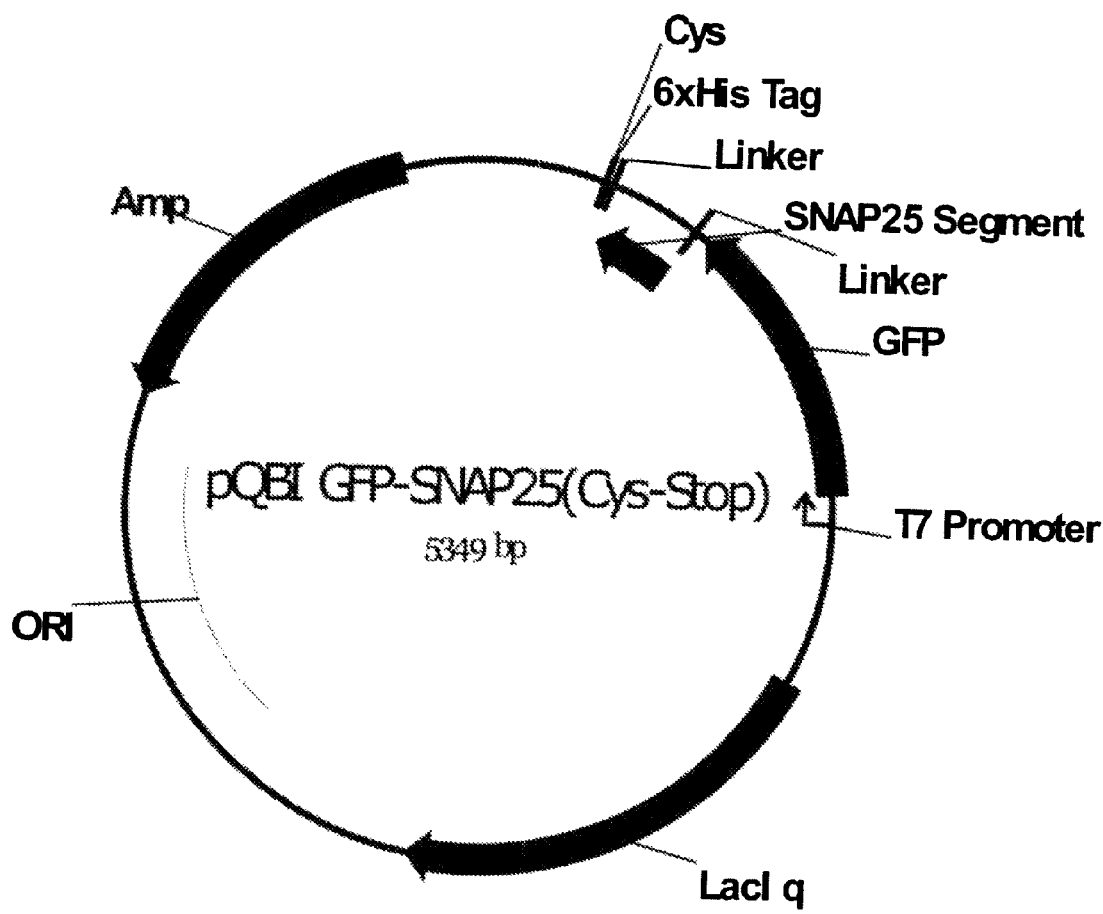
FIG. 6 shows (A) a schematic of plasmid pQBI GFP-SNAP25$_{(134-206)}$-6×HIS-C and (B) the nucleic acid and amino acid sequences (SEQ ID NOS: 19 and 20) of pQBI GFP-SNAP25$_{(134-206)}$-6×HIS-C.

The invention provides novel methods for determining the presence or activity of clostridial toxins including botulinum toxins of all serotypes as well as tetanus toxins. The novel methods of the invention, which rely on a clostridial toxin substrate useful for fluorescence polarization analysis, reduce the need for animal toxicity studies and can be used to analyze crude and bulk samples as well as highly purified dichain or single chain toxins or formulated toxin products. The fluorescence polarization-based methods of the invention are advantageous in that they are sensitive assays which are robust in terms of interference from background fluorescence present in samples. Furthermore, the novel methods of the invention can be performed as homogeneous solution-phase assays and are amenable to automated high-throughput formats.

As disclosed herein in Example I, a clostridial toxin substrate was prepared with Alexa Fluor® 594 as a fluorophore, green fluorescent protein (GFP) as a bulking group, and a portion of SNAP-25 (residues 134-206) as a clostridial toxin recognition sequence for BoNT/A. The absorption spectrum of the GFP-SNAP25$_{(134-206)}$-His6-Cys protein labeled with Alexa Fluor® 594 is shown herein in FIG. 8A, and the excitation and emission spectra of GFP-SNAP25$_{(134-206)}$-His6-C-Alexa Fluor® 594 are shown herein in FIG. 8B. As further disclosed herein in Example II, the GFP-SNAP25$_{(134-206)}$-His6-C-Alexa Fluor® 594 substrate was tested for its utility as a suitable substrate by assaying for the activity of BoNT/A reduced bulk toxin by recording the change in fluorescence polarization over time. As shown in FIG. 9, there was a reduction in fluorescence polarization at or shortly after the time the diluted bulk BoNT/A toxin was added, and toxin activity was detected at a concentration of as little as about 50 ng/ml (see panel 9D). These results demonstrate that the presence or activity of clostridial toxins can be determined using synthetic substrates assayed by fluorescence polarization.

As further disclosed herein, fluorescence polarization can be combined with fluorescence resonance energy transfer to sensitively assay for the presence or activity of a clostridial toxin. As disclosed in Example I, a GFP-SNAP25$_{(134-206)}$-His6-C protein was site-specifically labeled at the carboxy-terminal cysteine residue with Alexa Fluor® 546; the photoselection properties of GFP and Alexa Fluor® 546 provide for fluorescence resonance energy transfer (FRET) between the donor fluorophore GFP and the acceptor Alexa Fluor® 546. As disclosed in Example III and shown in FIG. 10, fluorescence polarization increased upon addition of recombinant BoNT/A light chain. Without wishing to be bound by the following, FRET in the intact substrate leads to an apparent depolarization of Alexa Fluor® 546 emission due to the significant angle between the initially selected dipole (GFP) and the dipole which would be selected by direct excitation of Alexa Fluor® 546. Upon proteolysis, the FRET effect is abolished, and polarization consequently increases even though rotation of the Alexa Fluor® dye is increased. The combination of fluorescence resonance energy transfer with fluorescence polarization enhanced the polarization change upon turnover, increasing the sensitivity of the assay (see FIG. 10). These results indicate that fluorescence polarization can be combined with fluorescence resonance energy transfer for enhanced sensitivity in assaying for the presence or activity of a clostridial toxin.

Based on these findings, the present invention provides a method of determining the presence or activity of a clostridial toxin by (a) treating with a sample, under conditions suitable for clostridial toxin protease activity, a clostridial toxin substrate which includes a fluorophore; a bulking group; and a clostridial toxin recognition sequence containing a cleavage site that intervenes between the fluorophore and the bulking group; (b) exciting the fluorophore with plane polarized light; and (c) determining fluorescence polarization of the treated substrate relative to a control substrate, where a change in fluorescence polarization of the treated substrate as compared to fluorescence polarization of the control substrate is indicative of the presence or activity of the clostridial toxin. In one embodiment, the change in fluorescence polarization is a decrease in fluorescence polarization. In another embodiment, step (c) includes determining the change in fluorescence polarization of the treated substrate over time.

In a method of the invention, a fluorophore can have, without limitation, a fluorescence lifetime of at least 0.5 nanoseconds, or at least 5 nanoseconds, or at least 10 nanoseconds. Any of a variety of fluorophores can be useful in the methods of the invention including, but not limited to, Alexa Fluor® dyes; fluorescein and fluorescein derivatives such as diaminotriazinylamino-fluorescein (DTAF); biarsenic derivatives of fluorescein such as fluorescein arsenical hairpin binding dye (FlAsH™) and red biarsenical dye (ReAsH™); carboxyfluorescein (FAM); Texas Red™; tetramethylcarboxyrhodamine (TMR); carboxy-x-rhodamine (ROX); rhodamine green; Oregon Green 488; BODIPY®-TR; BODIPY®-TMR; BODIPY®-FL; Cy3; Cy™3B and Dansyl. In one embodiment, the fluorophore is an Alexa Fluor® dye such as, without limitation, Alexa Fluor® 594. In other embodiments, the fluorophore is FlAsH™ or ReAsH™.

A variety of bulking groups are useful in the methods of the invention, including, without limitation, fluorescent proteins such as green fluorescent protein. In one embodiment, a method of the invention is practiced such that the change in molecular mass upon cleavage of the clostridial toxin substrate is at least 1000 Da. In a further embodiment, a method of the invention is practiced such that the decrease in fluorescence polarization is at least 5 millipolarization units (mP). In still a further embodiment, a method of the invention is practiced such that the decrease in fluorescence polarization is at least 15 mP.

A variety of recognition sequences can be included in a clostridial toxin substrate useful in a method of the invention.

In one embodiment, the recognition sequence is a BoNT/A recognition sequence such as, without limitation, a BoNT/A recognition sequence containing at least six consecutive residues of SNAP-25, where the six consecutive residues include Gln-Arg, or a peptidomimetic thereof. Such a BoNT/A recognition sequence can include, for example, residues 134 to 206 of SEQ ID NO: 2. A recognition sequence included in a clostridial toxin substrate useful in a method of the invention also can be, without limitation, a BoNT/B recognition sequence. Such a BoNT/B recognition sequence can contain, for example, at least six consecutive residues of VAMP, where the six consecutive residues include Gln-Phe, or a peptidomimetic thereof. In a further embodiment, a recognition sequence included in a clostridial toxin substrate useful in a method of the invention is a BoNT/C1 recognition sequence. Such a BoNT/C1 recognition sequence can contain, without limitation, at least six consecutive residues of syntaxin, where the six consecutive residues include Lys-Ala, or a peptidomimetic thereof. A BoNT/C1 recognition sequence useful in the invention also can contain at least six consecutive residues of SNAP-25, where the six consecutive residues include Arg-Ala, or a peptidomimetic thereof.

In a further embodiment, a recognition sequence included in a clostridial toxin substrate useful in a method of the invention is a BoNT/D recognition sequence. Such a BoNT/D recognition sequence can contain, for example, at least six consecutive residues of VAMP, where the six consecutive residues include Lys-Leu, or a peptidomimetic thereof. A recognition sequence useful in the invention also can be, for example, a BoNT/E recognition sequence. Such a BoNT/E recognition sequence can include, without limitation, residues 134 to 206 of SEQ ID NO: 2, or can contain at least six consecutive residues of SNAP-25, where the six consecutive residues include Arg-Ile, or a peptidomimetic thereof. In yet another embodiment, a recognition sequence included in a clostridial toxin substrate useful in a method of the invention is a BoNT/F recognition sequence. BoNT/F recognition sequences useful in the invention encompass, without limitation, those having at least six consecutive residues of VAMP, where the six consecutive residues include Gln-Lys, or a peptidomimetic thereof. A recognition sequence included in a clostridial toxin substrate useful in a method of the invention also can be a BoNT/G recognition sequence. Such BoNT/G recognition sequences encompass, without limitation, those having at least six consecutive residues of VAMP, where the six consecutive residues include Ala-Ala, or a peptidomimetic thereof. In still a further embodiment, a recognition sequence included in a clostridial toxin substrate useful in a method of the invention is a TeNT recognition sequence. Such a TeNT recognition sequence can be, without limitation, a sequence containing at least six consecutive residues of VAMP, where the six consecutive residues include Gln-Phe, or a peptidomimetic thereof.

Any of a variety of clostridial toxin substrates are useful for determining the presence or activity of a clostridial toxin according to a method of the invention. In one embodiment, a clostridial toxin substrate is a peptide or peptidomimetic having at least 100 residues. In another embodiment, a clostridial toxin substrate is a peptide or peptidomimetic having at least 200 residues. Furthermore, any of a variety of samples can be assayed according to a method of the invention including, but not limited to, crude cell lysates, isolated clostridial toxins including isolated clostridial toxin light chains; and formulated clostridial toxin products such as, without limitation, formulated BoNT/A, BoNT/B or BoNT/E toxin products.

The tetanus and botulinum neurotoxins which can be assayed according to a method of the invention are produced by Clostridia. These toxins cause the neuroparalytic syndromes of tetanus and botulism, with tetanus toxin acting mainly within the central nervous system and botulinum toxin acting on the peripheral nervous system. Clostridial neurotoxins share a similar mechanism of cell intoxication in which the release of neurotransmitters is blocked. In these toxins, which are composed of two disulfide-linked polypeptide chains, the larger subunit is responsible for neurospecific binding and translocation of the smaller subunit into the cytoplasm. Upon translocation and reduction in neurons, the smaller chain displays peptidase activity specific for protein components involved in neuroexocytosis. The "SNARE" protein targets of clostridial toxins are common to exocytosis in a variety of non-neuronal types; in these cells, as in neurons, light chain peptidase activity inhibits exocytosis.

Tetanus neurotoxin and botulinum neurotoxins B, D, F, and G specifically recognize VAMP (also known as synaptobrevin), an integral protein of the synaptic vesicle membrane. VAMP is cleaved at distinct bonds depending on the neurotoxin. Botulinum A and E neurotoxins recognize and cleave specifically SNAP-25, a protein of the presynaptic membrane, at two different sites in the carboxy-terminal portion of the protein. Botulinum neurotoxin C cleaves syntaxin, a protein of the nerve plasmalemma, in addition to SNAP-25. The three protein targets of the Clostridial neurotoxins are conserved from yeast to humans although cleavage sites and toxin susceptibility are not necessarily conserved (see below; see, also, Humeau et al., *Biochimie* 82:427-446 (2000); Niemann et al., *Trends in Cell Biol.* 4:179-185 (1994); and Pellizzari et al., *Phil. Trans. R. Soc. London* 354:259-268 (1999)).

Naturally occurring tetanus and botulinum neurotoxins are produced as polypeptide chains of 150 kDa without a leader sequence. These toxins may be cleaved by bacterial or tissue proteinases at an exposed protease-sensitive loop, generating active dichain toxin. Selective proteolytic cleavage activates the toxins by generating two disulfide-linked chains: an L chain of 50 kDa and an H chain of 100 kDa, which is composed of two domains denoted $H_N$ and $H_C$. This dichain toxin is more active than unnicked toxin. Naturally occurring clostridial toxins contain a single interchain disulfide bond bridging the heavy chain and light chain; such a bridge is important for neurotoxicity of toxin added extracellularly (Montecucco and Schiavo, *Quarterly Rev. Biophysics* 28:423-472 (1995)).

Figure 1:
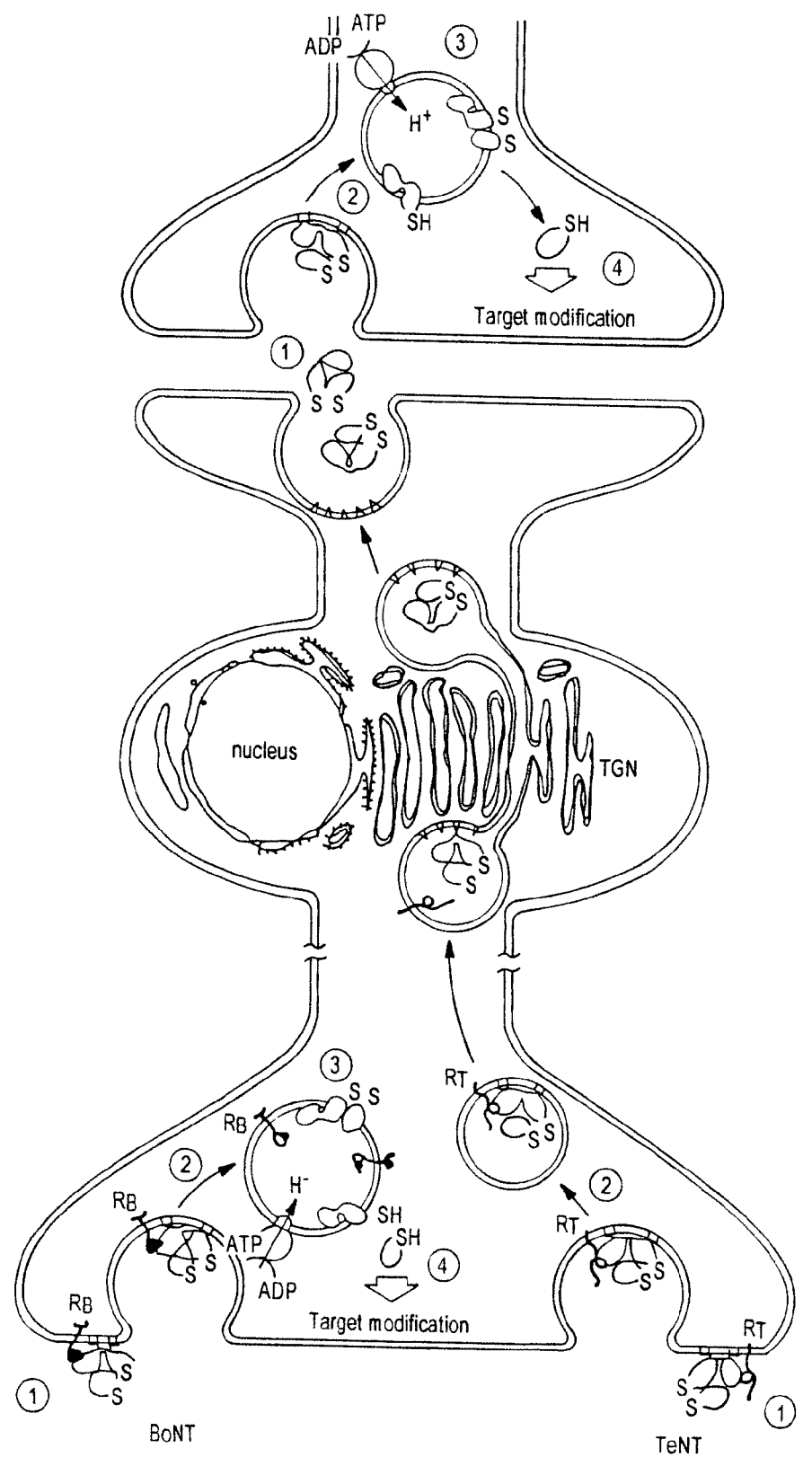

The clostridial toxins appear to be folded into three distinct domains of about 50 kDa which are connected by loops, with each domain having a distinct functional role. As illustrated in FIG. 1, the cell intoxication mechanism of the clostridial toxins consists of four distinct steps: (1) binding; (2) internalization; (3) membrane translocation; and (4) enzymatic target modification. The carboxy-terminal domain of the heavy chain ($H_C$) functions in neurospecific binding, while the amino-terminal domain of the H chain ($H_N$) functions in membrane translocation from endosome to cell cytoplasm. Following reduction of the disulfide linkage inside the cell, the zinc-endopeptidase activity of the L chain is liberated (Montecucco and Schiavo, supra, 1995).

The amino acid sequences of eight human clostridial neurotoxin serotypes have been derived from the corresponding genes (Niemann, "Molecular Biology of Clostridial Neurotoxins" in *Sourcebook of Bacterial Protein Toxins* Alouf and Freer (Eds.) pp. 303-348 London: Academic Press 1991). The L chain and H chain are composed of roughly 439 and 843 residues, respectively. Homologous segments are separated by regions of little or no similarity. The most well conserved regions of the L chain are the amino-terminal portion (100 residues) and central region (corresponding to residues 216 to 244 of TeNT), as well as the two cysteines forming the interchain disulfide bond. The 216 to 244 region contains a His-Glu-X-X-His binding motif characteristic of zinc-endopeptidases.

The clostridial toxin heavy chains are less well conserved than the light chains, with the carboxy-terminal portion of $H_C$ corresponding to residues 1140 to 1315 of TeNT the most variable. This is consistent with the involvement of the $H_C$ domain in binding to nerve terminals and the fact that different neurotoxins appear to bind different receptors.

Comparison of the nucleotide and amino acid sequences of the clostridial toxins indicates that they derive from a common ancestral gene. Spreading of these genes may have been facilitated by the fact that the clostridial neurotoxin genes are located on mobile genetic elements. As discussed further below, sequence variants of the seven botulinum toxins are known in the art. See, for example, Humeau et al., supra, 2000.

As discussed above, natural targets of the clostridial neurotoxins include VAMP, SNAP-25, and syntaxin. VAMP is associated with the synaptic vesicle membrane, whereas SNAP-25 and syntaxin are associated with the target membrane (see FIG. 2). BoNT/A and BoNT/E cleave SNAP-25 in the carboxy-terminal region, releasing nine or twenty-six amino acid residues, respectively, and BoNT/C1 also cleaves SNAP-25 near the carboxy-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. Thus, BoNT/B, BoNT/C1, BoNT/D, BoNT/F, BoNT/G or TeNT proteolysis results in release of a large portion of the cytosolic domain of VAMP or syntaxin, while only a small portion of SNAP-25 is released by BoNT/A, BoNT/C1 or BoNT/E cleavage (Montecucco and Schiavo, supra, 1995).

Naturally occurring SNAP-25, a protein of about 206 residues lacking a transmembrane segment, is associated with the cytosolic surface of the nerve plasmalemma (FIG. 2; see, also, Hodel et al., *Int. J. Biochemistry and Cell Biology* 30:1069-1073 (1998)). In addition to homologs highly conserved from *Drosophila* to mammals, SNAP-25-related proteins also have been cloned from yeast. SNAP-25 is required for axonal growth during development and may be required for nerve terminal plasticity in the mature nervous system. In humans, two isoforms are differentially expressed during development; isoform a is constitutively expressed during fetal development, while isoform b appears at birth and predominates in adult life. SNAP-25 analogues such as SNAP-23 also are expressed outside the nervous system, for example, in pancreatic cells.

Naturally occurring VAMP is a protein of about 120 residues, with the exact length depending on the species and isotype. As shown in FIG. 2, VAMP contains a short carboxy-terminal segment inside the vesicle lumen while most of the molecule is exposed to the cytosol. The proline-rich amino-terminal thirty residues are divergent among species and isoforms while the central portion of VAMP (residues 30 to 96), which is rich in charged and hydrophilic residues and includes known cleavage sites, is highly conserved. VAMP colocalizes with synaptophysin on synaptic vesicle membranes.

A variety of species homologs of VAMP are known in the art including human, rat, bovine, *Torpedo*, *Drosophila*, yeast, squid and *Aplysia* homologs. In addition, multiple isoforms of VAMP have been identified including VAMP-1, VAMP-2 and cellubrevin, and forms insensitive to toxin cleavage have been identified in non-neuronal cells. VAMP appears to be present in all vertebrate tissues although the distribution of VAMP-1 and VAMP-2 varies in different cell types. Chicken and rat VAMP-1 are not cleaved by TeNT or BoNT/B. These VAMP-1 homologs have a valine in place of the glutamine present in human and mouse VAMP-1 at the TeNT or BoNT/B cleavage site. The substitution does not affect BoNT/D, /F or /G, which cleave both VAMP-1 and VAMP-2 with similar rates.

Syntaxin is located on the cytosolic surface of the nerve plasmalemma and is membrane-anchored via a carboxy-terminal segment, with most of the protein exposed to the cytosol. Syntaxin colocalizes with calcium channels at the active zones of the presynaptic membrane, where neurotransmitter release takes place. In addition, syntaxin interacts with synaptotagmin, a protein of the SSV membrane, that forms a functional bridge between the plasmalemma and the vesicles. A variety of syntaxin isoforms have been identified. Two isoforms of slightly different length (285 and 288 residues) have been identified in nerve cells (isoforms 1A and 1B), with isoforms 2, 3, 4 and 5 expressed in other tissues. The different isoforms have varying sensitivities to BoNT/C1, with the 1A, 1B, 2 and 3 syntaxin isoforms cleaved by this toxin.

The methods of the invention rely, in part, on the use of fluorescence polarization. According to the theory of fluorescence polarization, when a fluorescently labeled molecule is excited with plane polarized light, it emits lights that has a degree of polarization which is inversely proportional to its molecular rotation. As a consequence, for large fluorescently labeled molecules, which remain relatively stationary during their excited state (about 4 ns for fluorescein), polarization remains relatively constant between excitation and emission. In contrast, small fluorescently labeled molecules rotate rapidly during the excited state, such that polarization of the light changes significantly between excitation and emission. Therefore, as a generalization, small molecules have low polarization values, and large molecules have high polarization values. See, for example, Weber, "Polarization of the Fluorescence of Solutions" in *Fluorescence & Phosphorescence Analysis pages* 217-241 Wiley Interscience (1996), and Jameson and Seifried, *Methods Enzym.* 19:222-233 (1999).

Fluorescence polarization assays are homogeneous in that they do not require a separation step and do not require attachment of substrate to an immobilized phase. Furthermore, polarization values can be measured repeatedly. In addition, fluorescence polarization is a sensitive technique which can be used to measure polarization values of fluorophores from low picomolar and micromolar levels. Polarization is also independent of fluorescence intensity.

Fluorescence anisotropy (commonly denoted as "r" or sometimes "A") is an alternative definition of how a plane of polarized light changes between excitation and emission with a rotating fluorophore. Fluorescence polarization and anisotropy are well known in the art as described in Lundblad et al., *Mol. Endocrin.* 10:607-612 (1996); Nasir et al., *Comb. Chem. High Throughput Screen.* 2:177-190 (1999); Sittampalam et al., *Curr. Opin. Chem. Biol.* 1:384-391 (1997); Thompson et al., *Biotechniques* 32:34-40 (1997); Lakowicz et al., *J. Biomol. Screen.* 5:123-132 (2000); and Fernandes, *Curr. Opin. Chem. Biol.* 2:597-603 (1998).

In particular, fluorescence polarization (P) and anisotropy (r) are defined as follows:

$$\text{Polarization} = P = \frac{I_{Vertical} - I_{Horizontal}}{I_{Vertical} + I_{Horizontal}}$$

and $$\text{Anistrophy} = r = \frac{I_{Vertical} - I_{Horizontal}}{I_{Vertical} + 2*I_{Horizontal}}$$

where $I_{Vertical}$ is the intensity of the emission light parallel to the excitation light plane and $I_{Horizontal}$ is the intensity of the emission light perpendicular to the excitation light plane. P and r, being ratios of light intensities, are dimensionless. Experimental data can be expressed in millipolarization units, where 1 polarization unit=1000 mP units, or in millianisotropy units, where 1 anisotropy unit=1000 mA units.

The formulae to interconvert polarization and anisotropy are as follows:

$$P = \frac{3r}{(2+r)} \text{ and } r = \frac{2P}{(3-P)}$$

Fundamentally, polarization is a relationship of fluorescence lifetime and how fast a fluorophore rotates in the time between excitation and emission. The principal factors controlling rotation are molar volume (V), absolute temperature (T), and viscosity ($\eta$). The rotational correlation time ($\Theta$) and the rotational relaxation time ($\rho_o$) are taken from the work of Perrin and Weber. In particular, the rotational correlation time ($\Theta$) is taken from the Perrin equation as follows:

$$\left(\frac{1}{P} - \frac{1}{3}\right) = \left(\frac{1}{P_o} - \frac{1}{3}\right)*(1 + T/\Theta)$$

and is defined as:
Rotational Correlation Time $$(\Theta) = \frac{\eta V}{RT}$$

Furthermore, the rotational relaxation time ($\rho_o$) is taken from the Perrin/Weber equation (Perrin, *J. Phys. Rad.* 7:390-401 (1926)), as follows:

$$\left(\frac{1}{P} - \frac{1}{3}\right) = \left(\frac{1}{P_o} - \frac{1}{3}\right)*(1 + 3T/P)$$

and is defined as:
Rotational Relaxation Time $$(\rho_o) = \frac{3\eta V}{RT}$$

where R is the gas constant, $\tau$ is the fluorescence lifetime, P is the polarization, and $P_0$ is the limiting polarization.

From the above, it can be seen that, where lifetime, viscosity, and temperature are held constant, the molecular volume (and thus the polarization or anisotropy) determines the rotation. The larger the molecular volume, the slower the molecule rotates and the higher the polarization and anisotropy values. Furthermore, as is evident from the equations above, the rotational relaxation time will be exactly three times longer than the rotational correlation time.

A method of the invention relies on a clostridial toxin substrate which includes, in part, a fluorophore. As used herein, the term "fluorophore" means a molecule that, when irradiated with light of a certain wavelength, emits light, also denoted fluorescence, of a different wavelength. The term fluorophore is synonymous in the art with the term "fluorochrome."

Fluorophores useful in the invention, as well as donor fluorophores which are discussed further below, include those having fluorescence lifetimes suitable for fluorescence polarization analysis. Useful fluorophores include, without limitation, Alexa Fluor® dyes; fluorescein and fluorescein derivatives such as diaminotriazinylamino-fluorescein (DTAF); biarsenic derivatives of fluorescein such as fluorescein arsenical hairpin binding dye (FlAsH™) and red biarsenical dye (ReAsH™); carboxyfluorescein (FAM); Texas Red™; tetramethylcarboxyrhodamine (TMR); carboxy-x-rhodamine (ROX); rhodamine green; Oregon Green 488; BODIPY®-TR; BODIPY®-TMR; BODIPY®-FL; Cy3, Cy™3B and Dansyl. Additional fluorophores suitable for fluorescence polarization are known in the art, including, but not limited to, long-wavelength fluorophores such as BODIPY®-TMR and BODIPY®-TR (Molecular Probes), which tend to minimize assay interference, and pH insensitive fluorophores such as BODIPY®-FL. See, for example, Owicki, *J. Biomol. Screening* 5:297-306 (2000); Burke et al., *Comb. Chem. & High Throughput Screen.* 6:183-194 (2003); and Jameson and Croney, *Comb. Chem. & High Throughput Screen.* 6:167-176 (2003). A variety of fluorophores and donor fluorophores useful for fluorescence polarization are commercially available from various sources such as Molecular Probes (Eugene, Oreg.) and Amersham Pharmacia Biotech (Piscataway, N.J.). One skilled in the art understands that these as well as other fluorophores suitable for fluorescence polarization are known in the art and can be useful in the methods of the invention.

As used herein, the term "bulking group" means a moiety having sufficient hydrodynamic volume such that, upon cleavage of a clostridial toxin substrate into which the bulking group is incorporated, there is a change in polarization of at least 3 millipolarization units (mP).

Any of a variety of moieties can be useful as a bulking group in a method of the invention including physical, chemical and biological moieties which can be covalently or non-covalently incorporated into a clostridial toxin substrate. In one embodiment, the bulking group is expressed as a fusion protein with another component of the clostridial toxin substrate. Bulking groups useful in the invention encompass natural and man-made moieties and further encompass, without limitation, inert moieties as well as those with biological or other activity. A bulking group useful in the invention can be, without limitation, a moiety having a size of greater than 1000 Da. A bulking group useful in the invention also can be, without limitation, a moiety having a size of greater than 2 kDa, 3 kDa, 4 kDa, 5 kDa, 10 kDa, 15 kDa, 20 kDa, 25 kDa, 30 kDa, 35 kDa or 40 kDa. See, also, Mattison et al., *Application Note for Protein Solutions Inc.* February 2001. One skilled in the art understands that a fluorophore with a suitable lifetime will be selected depending, in part, on the size of the bulking group.

A variety of bulking groups can be useful in the invention. As non-limiting examples, a bulking group useful in the invention can be an inert or active protein, peptide or peptidomimetic; an antibody; organic chemical; latex or other bead; or moiety such as streptavidin. Additional bulking groups useful in the invention encompass, without limitation, phage and other viruses; cells; liposomes; polymeric and non-polymeric matrices; gold and other particles; and microdevices and nanodevices. As non-limiting examples, a bulking group useful in the invention can be a fluorescent protein such as GFP or BFP, or a fragment thereof; a protein useful for affinity purification such as glutathione-S-transferase (GST) or maltose-binding protein (MBP); or an antibody such as, without limitation, an anti-FLAG, anti-hemagglutinin (HA) or anti-myc antibody. Streptavidin also can be a bulking group useful in the invention. As a non-limiting example, a biotinylation sequence can be covalently included in a clostridial toxin substrate, providing for association with streptavidin; enzymatic cleavage can be detected by following the fluorescence polarization change upon addition of streptavidin as described in Levine et al., "Measurement of specific protease activity utilizing fluorescence polarization," Anal. Biochem. 247:83-88 (1997).

A clostridial toxin substrate useful in the invention contains a cleavage site that "intervenes" between a fluorophore and a bulking group. Thus, the cleavage site is positioned in between the fluorophore and the bulking group such that proteolysis at the cleavage site results in a first cleavage product containing the fluorophore and a second cleavage product containing the bulking group. It is understood that all or only a portion of the clostridial toxin recognition sequence may intervene between the fluorophore and the bulking group.

A clostridial toxin substrate useful in the invention contains, in part, a clostridial toxin recognition sequence which includes a cleavage site. By definition, a clostridial toxin substrate is susceptible to cleavage by at least one clostridial toxin under conditions suitable for clostridial toxin protease activity.

As used herein, the term "clostridial toxin recognition sequence" means a scissile bond together with adjacent or non-adjacent recognition elements, or both, sufficient for detectable proteolysis at the scissile bond by a clostridial toxin under conditions suitable for clostridial toxin protease activity. A variety of clostridial toxin recognition sequences are discussed herein below.

In particular embodiments, a clostridial toxin substrate useful in the invention is a peptide or peptidomimetic having a defined length. A clostridial toxin substrate can be, for example, a peptide or peptidomimetic having at least 50, at least 100, at least 150, at least 200, at least 250, at least 300, at least 350, at least 500, at least 600, at least 700, at least 800 or at least 900 residues. In other embodiments, a clostridial toxin substrate has at most 20 residues, at most 30 residues, at most 40 residues, at most 50 residues, at most 60 residues, at most 70 residues, at most 80 residues, at most 90 residues, at most 100 residues, at most 150 residues, at most 200 residues, at most 250 residues, at most 300 residues, at most 350 residues or at most 400 residues.

It is understood that a clostridial toxin substrate useful in the invention optionally can include one or more additional components. As a non-limiting example, a flexible spacer sequence such as GGGGS (SEQ ID NO: 21) can be included in a clostridial toxin substrate useful in the invention. A useful clostridial toxin substrate further can include, without limitation, one or more of the following: an affinity tag such as HIS6; biotin or a biotinylation sequence; or an epitope such as FLAG, hemagglutinin (HA), c-myc, or AU1; an immunoglobulin hinge region; an N-hydroxysuccinimide linker; a peptide or peptidomimetic hairpin turn; or a hydrophilic sequence or another component or sequence that, for example, facilitates purification or promotes the solubility or stability of the clostridial toxin substrate.

As discussed further below, it is understood that the methods of the invention are applicable to crude samples as well as highly purified dichain and single chain toxins. As non-limiting examples, a method of the invention can be useful to determine the presence or activity of a clostridial toxin in a food or beverage sample; to assay a sample from a human or animal, for example, exposed to a clostridial toxin or having one or more symptoms of a clostridial toxin; to follow activity during production and purification of clostridial toxin; or to assay formulated clostridial toxin products such as pharmaceuticals or cosmetics.

A variety of samples are useful in the methods of the invention. As used herein, the term "sample" means any biological matter that contains or potentially contains an active clostridial toxin. Thus, the term sample encompasses, but is not limited to, purified or partially purified clostridial toxin; recombinant single chain or dichain toxin with a naturally or non-naturally occurring sequence; recombinant clostridial toxin with a modified protease specificity; recombinant clostridial toxin with an altered cell specificity; chimeric toxin containing structural elements from multiple clostridial toxin species or subtypes; bulk toxin; formulated toxin product; cells or crude, fractionated or partially purified cell lysates, for example, engineered to include a recombinant nucleic acid encoding a clostridial toxin; bacterial, baculoviral and yeast lysates; raw, cooked, partially cooked or processed foods; beverages; animal feed; soil samples; water samples; pond sediments; lotions; cosmetics; and clinical formulations. It further is understood that the term sample encompasses tissue samples, including, without limitation, mammalian tissue samples, livestock tissue samples such as sheep, cow and pig tissue samples; primate tissue samples; and human tissue samples. Such samples encompass, without limitation, intestinal samples such as infant intestinal samples, and tissue samples obtained from a wound.

As discussed further below, a variety of conditions suitable for clostridial toxin protease activity are useful in the methods of the invention. For example, conditions suitable for clostridial toxin protease activity can be provided such that at least 10% of the substrate is cleaved. Similarly, conditions suitable for clostridial toxin protease activity can be provided such that at least 20%, 30%, 40%, 50%, 60%, 70%, 80%, 90% or 95% of the clostridial toxin substrate is cleaved, or such that 100% of the clostridial toxin substrate is cleaved. In one embodiment, the conditions suitable for clostridial toxin protease activity are selected such that the assay is linear. In another embodiment, conditions suitable for clostridial toxin protease activity are provided such that at least 90% of the clostridial toxin substrate is cleaved. In a further embodiment, conditions suitable for clostridial toxin protease activity are provided such that at most 25% of the clostridial toxin substrate is cleaved. In yet further embodiments, conditions suitable for clostridial toxin protease activity are provided such that at most 5%, 10%, 15% or 20% of the clostridial toxin substrate is cleaved.

In the methods of the invention, the clostridial toxin substrate can be treated with a sample in solution phase. As used herein in reference to a clostridial toxin substrate, the term "in solution phase" means that the substrate is soluble and, during proteolysis, is not constrained or immobilized on a solid support such as a column or dish.

In the methods of the invention, a sample is treated with a clostridial toxin substrate under conditions suitable for clostridial toxin protease activity. Exemplary conditions suitable for clostridial toxin protease activity are well known in the art, and further can be determined by routine methods. See, for example, Hallis et al., *J. Clin. Microbiol.* 34:1934-1938 (1996); Ekong et al., *Microbiol.* 143:3337-3347 (1997); Shone et al., WO 95/33850; Schmidt and Bostian, supra, 1995; Schmidt and Bostian, supra, 1997; Schmidt et al., supra, 1998; and Schmidt and Bostian, U.S. Pat. No. 5,965,699. It is understood that conditions suitable for clostridial toxin protease activity can depend, in part, on the specific clostridial toxin type or subtype being assayed and the purity of the toxin preparation. Conditions suitable for clostridial toxin protease activity generally include a buffer, such as HEPES, Tris or sodium phosphate, typically in the range of pH 5.5 to 9.5, for example, in the range of pH 6.0 to 9.0, pH 6.5 to 8.5 or pH 7.0 to 8.0. Conditions suitable for clostridial toxin protease activity also can include, if desired, dithiothreitol, β-mercaptoethanol or another reducing agent, for example, where a dichain toxin is being assayed (Ekong et al., supra, 1997). In one embodiment, the conditions include DTT in the range of 0.01 mM to 50 mM; in other embodiments, the conditions include DTT in the range of 0.1 mM to 20 mM, 1 to 20 mM, or 5 to 10 mM. If desired, an isolated clostridial toxin or sample can be pre-incubated with a reducing agent, for example, with 10 mM dithiothreitol (DTT) for about 30 minutes prior to addition of clostridial toxin substrate.

Clostridial toxins are zinc metalloproteases, and a source of zinc, such as zinc chloride or zinc acetate, typically in the range of 1 to 500 μM, for example, 5 to 10 μM can be included, if desired, as part of the conditions suitable for clostridial toxin protease activity. One skilled in the art understands that zinc chelators such as EDTA generally are excluded from a buffer for determining the activity of a clostridial toxin.

Conditions suitable for clostridial toxin protease activity can optionally include a detergent such as TWEEN-20, which can be used, for example, in place of bovine serum albumin. TWEEN-20 can be provided, for example, in the range of 0.001% to 10% (v/v), or in the range of 0.01% to 1.0% (v/v). As a non-limiting example, TWEEN-20 can be included at a concentration of 0.1% (v/v).

Conditions suitable for clostridial toxin protease activity also can include, if desired, bovine serum albumin (BSA) or another agent which acts as a protein stabilizer, solubilizing agent or blocker of surface loss. As an example, when included, BSA typically is provided in the range of 0.1 mg/ml to 10 mg/ml. In one embodiment, BSA is included at a concentration of 1 mg/ml. See, for example, Schmidt and Bostian, supra, 1997. In another embodiment, BSA is included at a concentration of 0.1% (w/v).

The amount of clostridial toxin substrate can be varied in a method of the invention. A clostridial toxin substrate can be supplied, for example, at a concentration of 1 μM to 500 μM, 1 μM to 50 μM, 1 μM to 30 μM, 5 μM to 20 μM, 50 μM to 3.0 mM, 0.5 mM to 3.0 mM, 0.5 mM to 2.0 mM, or 0.5 mM to 1.0 mM. The skilled artisan understands that the concentration of clostridial toxin substrate or the amount of sample can be limited, if desired, such that the assay is linear. In one embodiment, a method of the invention relies on a clostridial toxin substrate concentration of less than 100 μM. In further embodiments, a method of the invention relies on a clostridial toxin substrate concentration of less than 50 μM or less than 25 μM. In a further embodiment, a method of the invention relies on a clostridial toxin substrate concentration of 10 μM to 20 μM. If desired, a linear assay also can be performed by mixing clostridial toxin substrate with corresponding, "unlabeled" substrate which lacks a fluorophore. The appropriate dilution can be determined, for example, by preparing serial dilutions of clostridial toxin substrate in the corresponding unlabeled substrate.

The concentration of purified or partially purified clostridial toxin to be assayed in a method of the invention generally is in the range of about 0.0001 ng/ml to 500 μg/ml toxin, for example, about 0.0001 ng/ml to 50 μg/ml toxin, 0.001 ng/ml to 500 μg/ml toxin, 0.001 ng/ml to 50 μg/ml toxin, 0.0001 to 5000 ng/ml toxin, for example, about 0.001 ng/ml to 5000 ng/ml, 0.01 ng/ml to 5000 ng/ml, 0.1 ng/ml to 5000 ng/ml, 1 ng/ml to 5000 ng/ml, 10 ng/ml to 5000 ng/ml, 50 ng/ml to 5000 ng/ml, 50 ng/ml to 500 ng/ml or 100 ng/ml to 5000 ng/ml toxin, which can be, for example, purified recombinant dichain toxin or formulated clostridial toxin product containing human serum albumin and excipients. Generally, the amount of purified toxin assayed in a method of the invention is in the range of 0.1 pg to 100 μg, for example, 0.1 pg to 50 μg or 0.1 pg to 10 μg.

The concentration of purified or partially purified clostridial toxin assayed in a method of the invention can be, for example, in the range of about 0.1 pM to 100 μM, 0.1 pM to 10 μM, 0.1 pM to 1 μM, 0.1 pM to 500 nM, 0.1 pM to 100 nM, for example, 1 pM to 2000 pM, 1 pM to 200 pM, 1 pM to 50 pM, 1 nM to 1 μM, 1 nM to 500 nM, 1 nM to 200 nM, 1 nM to 100 nM or 3 nM to 100 nM toxin, which can be, for example, purified native or recombinant light chain or dichain toxin or formulated clostridial toxin product containing human serum albumin and excipients. In particular embodiments, the concentration of purified or partially purified recombinant BoNT/A or BoNT/E light chain or dichain or formulated toxin product is in the range of 1 pM to 2000 pM, 10 pM to 2000 pM, 20 pM to 2000 pM, 40 pM to 2000 pM, or 1 pM to 200 pM. In further embodiments, the concentration of purified or partially purified recombinant BoNT/C light chain or dichain or formulated toxin product is in the range of 1 to 200 nM, 4 to 100 nM, 10 to 100 nM or 4 to 60 nM. One skilled in the art understands that the concentration of purified or partially purified clostridial toxin will depend on the serotype of the toxin assayed, as well as the purity or recombinant sequence of the toxin, the presence of inhibitory components, and the assay conditions. It is additionally understood that purified, partially purified or crude samples can be diluted to within a convenient range for assaying for clostridial toxin protease activity against a standard curve. Similarly, it is understood that a sample can be diluted, if desired, such that the assay is linear.

Conditions suitable for clostridial toxin protease activity also generally include, for example, temperatures in the range of about 20° C. to about 45° C., for example, in the range of 25° C. to 40° C., or the range of 35° C. to 39° C. Assay volumes often are in the range of about 5 to about 200 μl, for example, in the range of about 10 μl to 100 μl or about 0.5 μl to 100 μl, although nanoliter reaction volumes also can be used with the methods of the invention. Assay volumes also can be, for example, in the range of 100 μl to 2.0 ml or in the range of 0.5 ml to 1.0 ml.

One skilled in the art understands that fluorescence polarization reactions may or may not be terminated and that assay times can be varied as appropriate by the skilled artisan. Assay times generally depend, in part, on the concentration, purity and activity of the clostridial toxin and generally vary, without limitation, in the range of about 15 minutes to about 5 hours. As non-limiting examples, exemplary assay times include incubation, for example, at 37° C. for 30 minutes, 45 minutes, 60 minutes, 75 minutes or 90 minutes. In particular embodiments, at least 10%, 20%, 30%, 40%, 50%, 60%, 70%, 80%, 90%, 95% or 100% of the clostridial toxin substrate is cleaved. In further embodiments, the protease reaction is stopped before more than 5%, 10%, 15%, 20%, 25% or 50% of the clostridial toxin substrate is cleaved. It is understood that protease reactions can be terminated by the appropriate reagent, which generally depends on the fluorophore and other components of the substrate. As a non-limiting example, a protease reaction based on a substrate containing GFP as the donor fluorophore can be terminated by the addition of guanidinium chloride, for example, to a final concentration of 1 to 2 M. Protease reactions also can be terminated by addition of $H_2SO_4$; addition of about 0.5 to 1.0 sodium borate, pH 9.0 to 9.5; or addition of zinc chelators. One skilled in the art understands that protease reactions can be terminated, if desired, prior to exciting the fluorophore or donor fluorophore with plane polarized light.

As a non-limiting example, conditions suitable for clostridial toxin protease activity such as BoNT/A protease activity can be incubation at 37° C. for 90 minutes in a buffer containing 50 mM HEPES (pH 7.2), 10 µM $ZnCl_2$, 10 mM DTT, and 0.1% (v/v) TWEEN-20 with 10-16 µM substrate. If desired, samples containing BoNT/A, particularly dichain BoNT/A, can be preincubated with dithiothreitol, for example, for 20 or 30 minutes before addition of substrate. As a further non-limiting example, conditions suitable for BoNT/A protease activity can be incubation at 37° C. in a buffer such as 30 mM HEPES (pH 7.3) containing a reducing agent such as 5 mM dithiothreitol; and a source of zinc such as 25 µM zinc chloride (approximately 7 nM; Schmidt and Bostian, supra, 1997). BSA in the range of 0.1 mg/ml to 10 mg/ml, for example, 1 mg/ml BSA, also can be included when a sample is treated with a clostridial toxin substrate (Schmidt and Bostian, supra, 1997). As another non-limiting example, conditions suitable for clostridial toxin protease activity, for example BoNT/B activity, can be incubation in 50 mM HEPES, pH 7.4, with 10 µM zinc chloride, 1% fetal bovine serum and 10 mM dithiothreitol, with incubation for 90 minutes at 37° C. (Shone and Roberts, *Eur. J. Biochem.* 225:263-270 (1994); Hallis et al., supra, 1996); or can be, for example, incubation in 40 mM sodium phosphate, pH 7.4, with 10 mM dithiothreitol, optionally including 0.2% (v/v) Triton X-100, with incubation for 2 hours at 37° C. (Shone et al., supra, 1993). Conditions suitable for tetanus toxin protease activity or other clostridial toxin protease activity can be, for example, incubation in 20 mM HEPES, pH 7.2, and 100 mM NaCl for 2 hours at 37° C. with 25 µM peptide substrate (Cornille et al., supra, 1994).

In one embodiment, conditions suitable for clostridial toxin protease activity include cationic polyamino acids such as polyarginine in a buffer of suitable ionic strength. Where there is a charge difference in the clostridial toxin substrate as compared to the cleavage product, fluorescence polarization can be observed in the presence of polyarginine or another cationic polyamino acid (Simeonov et al., *Analytical Biochemistry* 304:193-199 (2002)). As a non-limiting example, if the net ionic charge of a fluorescently labeled cleavage product becomes negative following treatment of clostridial toxin substrate with a toxin sample, polyarginine will selectively bind to the fluorescently labeled cleavage product, thereby generating a measurable increase in polarization.

It is understood that any of a variety of control substrates are useful in the methods of the invention. A control substrate can be, for example, a clostridial toxin substrate which is not treated with active, toxin-containing sample; a polarization value determined before addition of the sample; or a similar, but different substrate which does not contain a toxin cleavage site or functional recognition sequence.

It is understood that the methods of the invention can be automated and can be configured in a high-throughput or ultra high-throughput format using, without limitation, 96-well, 384-well or 1536-well plates. Any of a variety of spectrofluorometers equipped with an appropriate polarizer can be used to assay the change in fluorescence polarization over time including, without limitation a Cary Eclipse spectrofluorometer; the Beckmann Affinity™ Multi-Mode plate reader; TECAN GeniusPro; and other systems from, for example, Perkin Elmer.

Further provided herein are methods of determining the presence or activity of a clostridial toxin by (a) treating with a sample, under conditions suitable for clostridial toxin protease activity, a clostridial toxin substrate containing (i) a donor fluorophore; (ii) an acceptor having an absorbance spectrum overlapping the emission spectrum of the donor fluorophore; and (iii) a clostridial toxin recognition sequence containing a cleavage site, where the cleavage site intervenes between the donor fluorophore and the acceptor and where, under the appropriate conditions, resonance energy transfer is exhibited between the donor fluorophore and the acceptor; (b) exciting the donor fluorophore with plane polarized light; and (c) determining fluorescence polarization of the treated substrate relative to a control substrate, where a change in fluorescence polarization of the treated substrate as compared to fluorescence polarization of the control substrate is indicative of the presence or activity of the clostridial toxin. In one embodiment, step (c) includes determining the change in fluorescence polarization of the treated substrate over time.

In the methods of the invention based on FRET-assisted fluorescence polarization, the change in fluorescence polarization can be an increase or decrease in fluorescence polarization. In one embodiment, the donor fluorophore has a fluorescence lifetime of at least 0.5 nanoseconds. In another embodiment, the donor fluorophore has a fluorescence lifetime of at least 5 nanoseconds. A donor fluorophore useful in the invention can be, without limitation, a green fluorescent protein (GFP); blue fluorescent protein (BFP); cyan fluorescent protein (CFP); yellow fluorescent protein (YFP); red fluorescent protein (RFP); Alexa Fluor® dye; fluorescein; a fluorescein derivative; diaminotriazinylamino-fluorescein (DTAF); a biarsenic derivative of fluorescein; fluorescein arsenical hairpin binding dye (FlAsH™); red biarsenical dye (ReAsH™); carboxyfluorescein (FAM); Texas Red™; tetramethylcarboxy-rhodamine (TMR); carboxy-x-rhodamine (ROX); rhodamine green; Oregon Green 488; BODIPY®-TR; BODIPY®-TMR; BODIPY®-FL; Cy3, Cy™3B or Dansyl. In particular embodiments, the donor fluorophore is a green fluorescent protein; blue fluorescent protein; cyan fluorescent protein; yellow fluorescent protein or red fluorescent protein. In one embodiment, the donor fluorophore is a green fluorescent protein (GFP). In another embodiment, the acceptor fluorophore is Alexa Fluor® 546.

Any of a variety of recognition sequences can be included in a clostridial toxin substrate useful in a method of the invention. In one embodiment, the recognition sequence is a BoNT/A recognition sequence such as, without limitation, a BoNT/A recognition sequence containing at least six consecutive residues of SNAP-25, where the six consecutive residues include Gln-Arg, or a peptidomimetic thereof. Such a BoNT/A recognition sequence can include, for example, residues 134 to 206 of SEQ ID NO: 2. A recognition sequence included in a clostridial toxin substrate useful in a method of the invention also can be, without limitation, a BoNT/B recognition sequence. Such a BoNT/B recognition sequence can contain, for example, at least six consecutive residues of VAMP, where the six consecutive residues include Gln-Phe, or a peptidomimetic thereof. In a further embodiment, a recognition sequence included in a clostridial toxin substrate useful in a method of the invention is a BoNT/C1 recognition sequence. Such a BoNT/C1 recognition sequence can contain, without limitation, at least six consecutive residues of syntaxin, where the six consecutive residues include Lys-Ala, or a peptidomimetic thereof. A BoNT/C1 recognition sequence useful in the invention also can contain at least six consecutive residues of SNAP-25, where the six consecutive residues include Arg-Ala, or a peptidomimetic thereof.

In a further embodiment, a recognition sequence included in a clostridial toxin substrate useful in a method of the invention is a BoNT/D recognition sequence. Such a BoNT/D recognition sequence can contain, for example, at least six consecutive residues of VAMP, where the six consecutive residues include Lys-Leu, or a peptidomimetic thereof. A recognition sequence useful in the invention also can be, for example, a BoNT/E recognition sequence. Such a BoNT/E recognition sequence can contain, without limitation, at least six consecutive residues of SNAP-25, where the six consecutive residues include Arg-Ile, or a peptidomimetic thereof. In yet another embodiment, a recognition sequence included in a clostridial toxin substrate useful in a method of the invention is a BoNT/F recognition sequence. BoNT/F recognition sequences useful in the invention encompass, without limitation, those having at least six consecutive residues of VAMP, where the six consecutive residues include Gln-Lys, or a peptidomimetic thereof. A recognition sequence included in a clostridial toxin substrate useful in a method of the invention also can be a BoNT/G recognition sequence. Such BoNT/G recognition sequences encompass, without limitation, those having at least six consecutive residues of VAMP, where the six consecutive residues include Ala-Ala, or a peptidomimetic thereof. In still a further embodiment, a recognition sequence included in a clostridial toxin substrate useful in a method of the invention is a TeNT recognition sequence. Such a TeNT recognition sequence can be, without limitation, a sequence containing at least six consecutive residues of VAMP, where the six consecutive residues include Gln-Phe, or a peptidomimetic thereof.

Any of a variety of clostridial toxin substrates can be useful in the methods of the invention, including peptides and peptidomimetics having at least 100 residues, or having at least 200 residues. Furthermore, any of a variety of samples can be assayed according to a method of the invention including, without limitation, crude cell lysates, isolated clostridial toxins including isolated clostridial toxin light chains; and formulated clostridial toxin products such as formulated BoNT/A, BoNT/B or BoNT/E toxin products.

Where a method of the invention involves fluorescence resonance energy transfer, the method relies on a clostridial toxin substrate which includes, in part, a donor fluorophore. Like a "fluorophore," a "donor fluorophore" is a molecule that, when irradiated with light of a certain wavelength, emits light, also denoted fluorescence, of a different wavelength. A donor fluorophore is a fluorophore which, when paired with a suitable acceptor, transfers energy to the acceptor.

As used herein, the term "acceptor" means a molecule that can absorb energy from, and upon excitation of, a donor fluorophore. An acceptor useful in a clostridial toxin substrate has an absorbance spectrum which overlaps the emission spectrum of a donor fluorophore included in the substrate. An acceptor useful in the invention generally has rather low absorption at a wavelength suitable for excitation of the donor fluorophore.

As set forth above, an acceptor has an absorbance spectrum that overlaps the emission spectrum of the donor fluorophore.

The term "overlapping," as used herein in reference to the absorbance spectrum of an acceptor and the emission spectrum of a donor fluorophore, means an absorbance spectrum and emission spectrum that are partly or entirely shared. Thus, in such overlapping spectra, the high end of the range of the donor fluorophore's emission spectrum is higher than the low end of the range of the acceptor's absorbance spectrum.

As set forth above, any of a variety of donor fluorophores can be useful in the invention, including, without limitation, green fluorescent protein; blue fluorescent protein; cyan fluorescent protein; yellow fluorescent protein; red fluorescent protein; an Alexa Fluor® dye; fluorescein; a fluorescein derivative; diaminotriazinylamino-fluorescein (DTAF); a biarsenic derivative of fluorescein; fluorescein arsenical hairpin binding dye (FlAsH™); red biarsenical dye (ReAsH™); carboxyfluorescein (FAM); Texas Red™; tetramethylcarboxy-rhodamine (TMR); carboxy-x-rhodamine (ROX); rhodamine green; Oregon Green 488; BODIPY®-TR; BODIPY®-TMR; BODIPY®-FL; Cy3, Cy™3B or Dansyl. A variety of acceptors also can be useful in the invention including, but not limited to, Alexa Fluor® dyes such as Alexa Fluor® 546, Alexa Fluor® 568, Alexa Fluor® 610, Alexa Fluor® 660 and Alexa Fluor® 750; QSY® 7; tetramethylrhodamine; octadecylrhodamine; flavodoxin, cytochrome c peroxidase; and rubredoxin.

Exemplary donor fluorophore-acceptor pairs which exhibit FRET and are useful in the methods of the invention encompass, without limitation, GFP and Alexa Fluor® 546; fluorescein and QSY® 7; fluorescein and tetramethylrhodamine; and dansyl and octadecylrhodamine. Further exemplary donor fluorophore-acceptor pairs which are useful in the methods of the invention encompass, without limitation, Alexa Fluor® 633 and Alexa Fluor® 660; Alexa Fluor® 594 and Alexa Fluor® 610; Alexa Fluor® 700 and Alexa Fluor® 750; and Alexa Fluor® 555 and Alexa Fluor® 568. Additional acceptors useful in the invention include those in which the acceptor is a protein with a visible chromophore such as, without limitation, flavodoxin, cytochrome c peroxidase or rubredoxin; such a protein can have, for example, a molecular weight in the range of 6 to 34 kDa and a chromophore which absorbs strongly in the region between 400-500 nm. Exemplary donor fluorophore-acceptor pairs based on such proteins include, but are not limited to, 5-(((2-iodoaacetyl)amino)ethyl)amino)naphthalene-1-sulfonic acid (1,5 IAEDANS) and flavodoxin; 4-acetamido-4' maleimidylstilbene 2,2' disulfonic acid and cytochrom c peroxidase; and Alexa Fluor®488 and rubredoxin. These and other donor fluorophores suitable for fluorescence polarization can be paired with any of a variety of acceptors having an absorbance spectrum which overlaps the emission spectrum of the donor fluorophore.

One skilled in the art understands that the methods of the invention based on FRET-assisted fluorescence polarization optionally utilize a substrate which includes a bulking group in addition to the donor fluorophore and acceptor. One skilled in the art understands that the optional inclusion of a bulking group depends on the molecular weight and bulking characteristics of the selected donor fluorophore and acceptor. A variety of bulking groups are optionally useful in the invention, including those described herein above.

Substrates useful in the invention can be prepared by recombinant methods or using synthetic chemical methods, or a combination thereof. As described herein in Example I, a fusion protein containing a bulking group fused to a BoNT/A clostridial toxin recognition sequence and a carboxy-terminal cysteine was prepared by recombinant methods. The carboxy-terminal cysteine was used for attachment of a fluorophore to produce the complete clostridial toxin substrate. Recombinant methods for preparation of clostridial toxin substrates which are fusion proteins are well known in the art as described, for example, in Ausubel, *Current Protocols in Molecular Biology* John Wiley & Sons, Inc., New York 2000.

Chemical methods for modifying a protein, peptide or peptidomimetic to contain a fluorophore and bulking group, or a donor fluorophore and acceptor, are well known in the art (Fairclough and Cantor, *Methods Enzymol.* 48:347-379 (1978); Glaser et al., *Chemical Modification of Proteins* Elsevier Biochemical Press, Amsterdam (1975); Haugland, *Excited States of Biopolymers* (Steiner Ed.) pp. 29-58, Plenum Press, New York (1983); Means and Feeney, *Bioconjugate Chem.* 1:2-12 (1990); Matthews et al., *Methods Enzymol.* 208:468-496 (1991); Lundblad, *Chemical Reagents for Protein Modification* 2nd Ed., CRC Press, Boca Ratan, Fla. (1991); Haugland, supra, 1996). A variety of groups can be used to couple a fluorophore, bulking group, donor fluorophore or acceptor, for example, to a peptide or peptidomimetic containing a clostridial toxin recognition sequence. A thiol group, for example, can be used to couple a fluorophore, bulking group, donor fluorophore or acceptor to the desired position in a peptide or peptidomimetic to produce a clostridial toxin substrate useful in the invention (see Example I). Haloacetyl and maleimide labeling reagents also can be used to couple a fluorophore, bulking group, donor fluorophore or acceptor in preparing a clostridial toxin substrate useful in the invention. See, for example, Wu and Brand, supra, 1994.

Cross-linker moieties also can be useful for preparing a clostridial toxin substrate. Cross-linkers are well known in the art and include homo- and hetero-bifunctional cross-linkers such as BMH and SPDP. Where a fluorophore, bulking group, donor fluorophore or acceptor is a protein, well known chemical methods for specifically linking molecules to the amino- or carboxy-terminus of a protein can be employed. See, for example, "Chemical Approaches to Protein Engineering" in *Protein Engineering: A Practical Approach* Rees et al. (Eds) Oxford University Press, 1992.

Where a clostridial toxin substrate contains a fluorophore and bulking group, the clostridial toxin cleavage site is positioned between the fluorophore and bulking group. In one embodiment, the fluorophore is positioned carboxy-terminal of the cleavage site while the bulking group is positioned amino-terminal of the cleavage site. In another embodiment, the fluorophore is positioned amino-terminal of the cleavage site while the bulking group is positioned carboxy-terminal of the cleavage site.

Where a clostridial toxin substrate contains a donor fluorophore and an acceptor, the clostridial toxin cleavage site is positioned between the donor fluorophore and the acceptor. In one embodiment, the donor fluorophore is positioned amino-terminal of the cleavage site while the acceptor is positioned carboxy-terminal of the cleavage site. In another embodiment, the donor fluorophore is positioned carboxy-terminal of the cleavage site while the acceptor is positioned amino-terminal of the cleavage site.

One skilled in the art understands that there are several considerations in selecting and positioning a fluorophore and a bulking group, or a donor fluorophore and an acceptor, in a clostridial toxin substrate useful in the invention. The fluorophore and bulking group, or donor fluorophore and acceptor, generally are positioned to minimize interference with substrate binding to, or proteolysis by, the clostridial toxin. Thus, a fluorophore and bulking group, or donor fluorophore and acceptor, can be selected and positioned, for example, so as to minimize the disruption of bonded and non-bonded interactions that are important for binding, and to minimize steric hindrance. In addition, as discussed further below, the spatial distance between an acceptor and donor fluorophore generally is limited to achieve efficient energy transfer from the donor fluorophore to the acceptor.

As discussed above, efficiency of energy transfer from a donor fluorophore to an acceptor is dependent, in part, on the spatial separation of the donor fluorophore and acceptor molecules. As the distance between the donor fluorophore and acceptor increases, there is less energy transfer to the acceptor, and the donor fluorescence signal therefore increases. The overall energy transfer between the donor fluorophore and acceptor is dependent upon many factors, including the separation distance between the donor fluorophore and acceptor in the substrate, the spectral overlap between donor fluorophore and acceptor, and the substrate concentration. One skilled in the art understands that, as the concentration of substrate increases, intermolecular quenching of the donor, even after proteolytic cleavage, can become a factor. This phenomenon is denoted the "inner filter effect." One skilled in the art further understands that the concentration of substrate can be controlled as described above.

The Förster distance, which is the separation between a donor fluorophore and an acceptor for 50% energy transfer, represents a spatial separation between donor fluorophore and acceptor that provides a good sensitivity. For peptide substrates, adjacent residues are separated by a distance of approximately 3.6 Å in the most extended conformation. For example, the calculated Förster distance for a fluorescein/tetramethylrhodamine pair is 55 Å, which would represent a spatial separation between fluorescein and tetramethylrhodamine of about 15 residues in the most extended conformation. Because peptides and peptidomimetics in solution rarely have a fully extended conformation, donor fluorophores and acceptors can be more widely separated than expected based on a calculation performed using 3.6 Å per residue and still remain within the Förster distance as shown, for example, by the occurrence of FRET between donor-acceptor pairs separated by about 50 amino acids (Graham et al., *Analyt. Biochem.* 296: 208-217 (2001)).

Förster theory is based on very weak interactions between a donor fluorophore and an acceptor; spectroscopic properties such as absorption of one fluorophore should not be altered in the presence of the other, defining the shortest distance range over which the theory is valid. It is understood that, for many donor fluorophore-acceptor pairs, Förster theory is valid when donor fluorophores and acceptors are separated by about 10 Å to 100 Å. However, for particular donor fluorophore-acceptor pairs, Förster theory is valid below 10 Å as determined by subpicosecond techniques (Kaschke and Ernsting, Ultrafast Phenomenon in Spectroscopy (Klose and Wilhelmi (Eds.)) Springer-Verlag, Berlin 1990).

In particular embodiments, the invention provides a method that relies on a clostridial toxin substrate in which the donor fluorophore is spatially separated from the acceptor by a distance of at most 100 Å. In other embodiments, the invention provides a method that relies on a clostridial toxin substrate in which the donor fluorophore is spatially separated from the acceptor by a distance of at most 90 Å, 80 Å, 70 Å, 60 Å, 50 Å, 40 Å, 30 Å or 20 Å. In further embodiments, the invention provides a method that relies on a clostridial toxin substrate in which the donor fluorophore is spatially separated from the acceptor by a distance of 10 Å to 100 Å, 10 Å to 80 Å, 10 Å to 60 Å, 1A to 40 Å, 10 Å to 20 Å, 20 Å to 100 Å, 20 Å to 80 Å, 20 Å to 60 Å, 20 Å to 40 Å, 40 Å to 100 Å, 40 Å to 80 Å or 40 Å to 60 Å. In still further embodiments, the invention provides a method that relies on a clostridial toxin substrate in which the donor fluorophore and the acceptor are separated in the primary amino acid sequence by at most six residues, at most eight residues, at most ten residues, at most twelve residues, at most fifteen residues, at most twenty residues, at most twenty-five residues, at most thirty residues, at most thirty-five residues, at most forty residues, at most forty-five residues, at most fifty residues, at most sixty residues, at most seventy residues, at most eighty residues, at most ninety residues, at most 100 residues, at most 150 residues, at most 200 residues or up to the full-length of a naturally occurring clostridial toxin target protein.

One skilled in the art understands that a clostridial toxin substrate useful in the invention can be designed, if desired, to optimize the efficiency of FRET. One skilled in the art understands that a donor fluorophore can be selected, if desired, with a high quantum yield, and acceptor can be selected, if desired, with a high extinction coefficient to maximize the Förster distance. One skilled in the art further understands that fluorescence arising from direct excitation of an acceptor can be difficult to distinguish from fluorescence resulting from resonance energy transfer. Thus, it is recognized that a donor fluorophore and acceptor can be selected which have relatively little overlap of their excitation spectra such that the donor can be excited at a wavelength that does not result in direct excitation of the acceptor. It further is recognized that a clostridial toxin substrate useful in the invention can be designed so that the emission spectra of the donor fluorophore and acceptor overlap relatively little such that the two emissions can be readily distinguished.

Specific and distinct cleavage sites for different clostridial toxins are well known in the art. BoNT/A cleaves a Gln-Arg bond; BoNT/B and TeNT cleave a Gln-Phe bond; BoNT/C1 cleaves a Lys-Ala or Arg-Ala bond; BoNT/D cleaves a Lys-Leu bond; BoNT/E cleaves an Arg-Ile bond; BoNT/F cleaves a Gln-Lys bond; and BoNT/G cleaves an Ala-Ala bond (see Table A). In standard nomenclature, the sequence surrounding a clostridial toxin cleavage site is denoted $P_5$-$P_4$-$P_3$-$P_2$-$P_1$-$P_1'$-$P_2'$-$P_3'$-$P_4'$-$P_5'$ with $P_1$-$P_1'$ representing the scissile bond. It is understood that a $P_1$ or $P_1'$ site, or both, can be substituted with another amino acid or amino acid mimetic in place of the naturally occurring residue. As an example, BoNT/A substrates have been prepared in which the $P_1$ position (Gln) is modified to be an alanine, 2-aminobutyric acid or asparagine residue; these substrates were hydrolyzed by BoNT/A at the $P_1$Arg bond (Schmidt and Bostian, *J. Protein Chem.* 16:19-26 (1997)). While it is recognized that substitutions can be introduced at the $P_1$ position of the scissile bond, for example, a BoNT/A scissile bond, it is further recognized that conservation of the $P_1'$ residue can be advantageous (Vaidyanathan et al., *J. Neurochem.* 72:327-337 (1999)). Thus, in particular embodiments, the invention provides a method which relies on a clostridial toxin substrate having a clostridial toxin recognition sequence in which the $P_1'$ residue is not modified or substituted relative to the naturally occurring residue in a target protein cleaved by the clostridial toxin. In other embodiments, the invention provides a method which relies on a clostridial toxin substrate having a recognition sequence in which the $P_1$ residue is modified or substituted relative to the naturally occurring residue in a target protein cleaved by the clostridial toxin; such a clostridial toxin substrate retains susceptibility to peptide bond cleavage between the $P_1$ and $P_1'$ residues.

TABLE A

BONDS CLEAVED IN HUMAN VAMP-2, SNAP-25 OR SYNTAXIN

| Toxin | Target | $P_4$-$P_3$-$P_2$-$P_1$—$P_1'$-$P_2'$-$P_3'$-$P_4'$ | SEQ ID NO: |
|---|---|---|---|
| BoNT/A | SNAP-25 | Glu-Ala-Asn-Gln—Arg*-Ala-Thr-Lys | 22 |
| BoNT/B | VAMP-2 | Gly-Ala-Ser-Gln—Phe*-Glu-Thr-Ser | 23 |
| BoNT/C1 | syntaxin | Asp-Thr-Lys-Lys—Ala*-Val-Lys-Tyr | 24 |
| BoNT/D | VAMP-2 | Arg-Asp-Gln-Lys—Leu*-Ser-Glu-Leu | 25 |
| BoNT/E | SNAP-25 | Gln-Ile-Asp-Arg—Ile*-Met-Glu-Lys | 26 |
| BoNT/F | VAMP-2 | Glu-Arg-Asp-Gln—Lys*-Leu-Ser-Glu | 27 |
| BoNT/G | VAMP-2 | Glu-Thr-Ser-Ala—Ala*-Lys-Leu-Lys | 28 |
| TeNT | VAMP-2 | Gly-Ala-Ser-Gln—Phe*-Glu-Thr-Ser | 29 |

*Scissile bond shown in bold

SNAP-25, VAMP and syntaxin share a short motif located within regions predicted to adopt an α-helical conformation. This motif is present in SNAP-25, VAMP and syntaxin isoforms expressed in animals sensitive to the neurotoxins. In contrast, *Drosophila* and yeast homologs that are resistant to these neurotoxins and syntaxin isoforms not involved in exocytosis contain sequence variations in the α-helical motif regions of these VAMP and syntaxin proteins.

Multiple repetitions of the α-helical motif are present in proteins sensitive to cleavage by clostridial toxins: Four copies are naturally present in SNAP-25; two copies are naturally present in VAMP; and two copies are naturally present in syntaxin. Furthermore, peptides corresponding to the specific sequence of the α-helical motifs can inhibit neurotoxin activity in vitro and in vivo, and such peptides can cross-inhibit different neurotoxins. In addition, antibodies raised against such peptides can cross-react among the three target proteins, indicating that this α-helical motif is exposed on the protein surface and adopts a similar configuration in each of the three target proteins. Consistent with these findings, SNAP-25-specific, VAMP-specific and syntaxin-specific neurotoxins cross-inhibit each other by competing for the same binding site, although they do not cleave targets non-specifically. These results indicate that a clostridial toxin recognition sequence can include, if desired, at least one α-helical motif. It is recognized that an α-helical motif is not required for cleavage by a clostridial toxin, as evidenced by 16-mer and 17-mer substrates for BoNT/A known in the art.

Although multiple α-helical motifs are found in the naturally occurring SNAP-25, VAMP and syntaxin target proteins, a clostridial toxin recognition sequence useful in a clostridial toxin substrate can have a single α-helical motif. In particular embodiments, a method of the invention relies on a clostridial toxin recognition sequence including two or more α-helical motifs. A BoNT/A or BoNT/E recognition sequence can include, for example, the S4 α-helical motif, alone or combined with one or more additional α-helical motifs; a BoNT/B, BoNT/G or TeNT recognition sequence can include, for example, the V2 α-helical motif, alone or combined with one or more additional α-helical motifs; a BoNT/C1 recognition sequence can include, for example, the S4 α-helical motif, alone or combined with one or more additional α-helical motifs, or the X2 α-helical motif, alone or combined with one or more additional α-helical motifs; and a BoNT/D or BoNT/F recognition sequence can include, for example, the V1 α-helical motif, alone or combined with one or more additional α-helical motifs.

As used herein, the term "botulinum toxin serotype A recognition sequence" is synonymous with "BoNT/A recognition sequence" and means a scissile bond together with adjacent or non-adjacent recognition elements, or both, sufficient for detectable proteolysis at the scissile bond by a BoNT/A under conditions suitable for clostridial toxin protease activity. A scissile bond cleaved by BoNT/A can be, for example, Gln-Arg.

A variety of BoNT/A recognition sequences are well known in the art and are useful in the invention. A BoNT/A recognition sequence can have, for example, residues 134 to 206 or residues 137 to 206 of human SNAP-25 (Ekong et al., supra, 1997; U.S. Pat. No. 5,962,637). A BoNT/A recognition sequence also can include, without limitation, the sequence Thr-Arg-Ile-Asp-Glu-Ala-Asn-Gln-Arg-Ala-Thr-Lys-Met (SEQ ID NO: 30) or a peptidomimetic thereof, which corresponds to residues 190 to 202 of human SNAP-25; Ser-Asn-Lys-Thr-Arg-Ile-Asp-Glu-Ala-Asn-Gln-Arg-Ala-Thr-Lys (SEQ ID NO: 31) or a peptidomimetic thereof, which corresponds to residues 187 to 201 of human SNAP-25; Ser-Asn-Lys-Thr-Arg-Ile-Asp-Glu-Ala-Asn-Gln-Arg-Ala-Thr-Lys-Met (SEQ ID NO: 32) or a peptidomimetic thereof, which corresponds to residues 187 to 202 of human SNAP-25; Ser-Asn-Lys-Thr-Arg-Ile-Asp-Glu-Ala-Asn-Gln-Arg-Ala-Thr-Lys-Met-Leu (SEQ ID NO: 33) or a peptidomimetic thereof, which corresponds to residues 187 to 203 of human SNAP-25; Asp-Ser-Asn-Lys-Thr-Arg-Ile-Asp-Glu-Ala-Asn-Gln-Arg-Ala-Thr-Lys-Met (SEQ ID NO: 34) or a peptidomimetic thereof, which corresponds to residues 186 to 202 of human SNAP-25; or Asp-Ser-Asn-Lys-Thr-Arg-Ile-Asp-Glu-Ala-Asn-Gln-Arg-Ala-Thr-Lys-Met-Leu (SEQ ID NO: 35) or a peptidomimetic thereof, which corresponds to residues 186 to 203 of human SNAP-25. See, for example, Schmidt and Bostian, J. Protein Chem. 14:703-708 (1995); Schmidt and Bostian, supra, 1997; Schmidt et al., FEBS Letters 435:61-64 (1998); and Schmidt and Bostian, U.S. Pat. No. 5,965,699). If desired, a similar BoNT/A recognition sequence can be prepared from a corresponding (homologous) segment of another BoNT/A-sensitive SNAP-25 isoform or homolog such as, for example, murine, rat, goldfish or zebrafish SNAP-25 or can be any of the peptides described herein or known in the art, for example, in U.S. Pat. No. 5,965,699.

A BoNT/A recognition sequence useful in the invention can correspond to a segment of a protein that is sensitive to cleavage by botulinum toxin serotype A, or can be substantially similar to a segment of a BoNT/A-sensitive protein. As illustrated in Table B, a variety of naturally occurring proteins sensitive to cleavage by BoNT/A are known in the art and include, for example, human, mouse and rat SNAP-25; and goldfish SNAP-25A and SNAP-25B. Thus, a BoNT/A recognition sequence useful in the invention can correspond, for example, to a segment of human SNAP-25, mouse SNAP-25, rat SNAP-25, goldfish SNAP-25A or 25B, or another naturally occurring protein sensitive to cleavage by BoNT/A. Furthermore, comparison of native SNAP-25 amino acid sequences cleaved by BoNT/A reveals that such sequences are not absolutely conserved (see Table B and FIG. 3), indicating that a variety of amino acid substitutions and modifications relative to a naturally occurring BoNT/A-sensitive SNAP-25 sequence can be tolerated in a BoNT/A recognition sequence useful in the invention.

TABLE B

Cleavage of SNAP-25 and related proteins[a,b,c,d]

| Species-Isoform | Cleavage Sites | SEQ ID NO: | Resistance to Cleavage by |
|---|---|---|---|
| | BoNT/E ⇓   BoNT/A ⇓⇓   BoNT/C | | |
| human mouse-SNAP-25 rat | 174                                            206<br>qnrqid ri mekadsnktridean qra tkmlgsg | | none[a] |
| human-SNAP-23 | 180                                         end<br>qnpqik ri tdkadtnrdridian ara kklids | | all[b] |
| mouse-SNAP-23 | 179                                         end<br>qnqqiq ki tekadtnknridian tra kklids | | BoNT/A & C |
| chicken-SNAP-25 | 174                                             end<br>qnrqid ri meklipikpglmkpt svq qrcsavvk | | BoNT/A & C |
| goldfish-SNAP-25A | 171                                           end<br>qnrqid ri mdmadsnktridean qra tkmlgsg | | none |
| goldfish-SNAP-25B | 172                                           end<br>qnrqid ri mekadsnktridean qra tkmlgsg | | none |
| Torpedo-SNAP-25 | 180                                        end<br>qnaqvd ri vvkgdmnkaridean kha tkml | | BoNT/E[c] & A |
| sea urchin-SNAP-25 | 180                                             end<br>qnsqvg ri tskaesnegrinsad kra knilrnk | | (?)[e] |
| | 203                                         end | | |

TABLE B-continued

Cleavage of SNAP-25 and related proteins[a,b,c,d]

| Species-Isoform | Cleavage Sites | SEQ ID NO: | Resistance to Cleavage by |
|---|---|---|---|
| C-elegans-SNAP-25 | qnrqld ri hdkqsnevrvesank rak nlitk | | BoNT/A & C |
| Drosophila-SNAP-25 | 182                      end<br>qnrqid ri nrkgesneariavan qra hqllk | | BoNT/E & A[e] |
| leech-SNAP-25 | 181                      end<br>qnrqvd ri nnkmtsnqlrisdan kra skllke | | BoNT/A[e] |

[a]= In vitro cleavage of SNAP-25 requires 1000-fold higher BoNT/C concentration than BoNT/A or /E.
[b]= Substitution of p182r, or k185dd (boxes) induces susceptibility toward BoNT/E.
[c]= Resistance to BoNT/A possibly due to d189 or e189 substitution by v189, see box.
[d]= Note that Torpedo is susceptible to BoNT/A.
[e]= Note the presence of several non-conservative mutations around putative cleavage sites.

A clostridial toxin substrate, such as a substrate containing a BoNT/A recognition sequence, can have one or multiple modifications as compared to a naturally occurring sequence that is cleaved by the corresponding clostridial toxin. As an example, as compared to a 17-mer corresponding to residues 187 to 203 of human SNAP-25, substitution of Asp193 with Asn in the BoNT/A substrate resulted in a relative rate of proteolysis of 0.23; substitution of Glu194 with Gln resulted in a relative rate of 2.08; substitution of Ala195 with 2-aminobutyric acid resulted in a relative rate of 0.38; and substitution of Gln197 with Asn, 2-aminobutyric acid or Ala resulted in a relative rate of 0.66, 0.25, or 0.19, respectively (see Table C). Furthermore, substitution of Ala199 with 2-aminobutyric acid resulted in a relative rate of 0.79; substitution of Thr200 with Ser or 2-aminobutyric acid resulted in a relative rate of 0.26 or 1.20, respectively; substitution of Lys201 with Ala resulted in a relative rate of 0.12; and substitution of Met202 with Ala or norleucine resulted in a relative rate of 0.38 or 1.20, respectively. See Schmidt and Bostian, supra, 1997. These results indicate that a variety of residues can be substituted in a clostridial toxin substrate as compared to a naturally occurring toxin-sensitive sequence. In the case of BoNT/A, these results indicate that residues including but not limited to Glu194, Ala195, Gln197, Ala199, Thr200 and Met202, Leu203, Gly204, Ser205, and Gly206, as well as residues more distal from the Gln-Arg scissile bond, can be substituted or conjugated to a fluorophore, bulking group, donor fluorophore or acceptor in a BoNT/A substrate useful in the invention. Such a BoNT/A substrate is detectably proteolyzed at the scissile bond by BoNT/A under conditions suitable for clostridial toxin protease activity. Thus, a BoNT/A substrate can include, if desired, one or several amino acid substitutions, additions or deletions relative to a naturally occurring SNAP-25 sequence.

TABLE C

KINETIC PARAMETERS OF BoNT/A SYNTHETIC PEPTIDE SUBSTRATES

| Peptide | Sequence[a] | SEQ ID NO: | Relative Rate[b] |
|---|---|---|---|
| [1-15] | SNKTRIDEANQRATK | 31 | 0.03 |
| [1-16] | SNKTRIDEANQRATKM | 32 | 1.17 |
| [1-17] | SNKTRIDEANQRATKML | 33 | 1.00 |
| M16A | SNKTRIDEANQRATKAL | 50 | 0.38 |
| M16X | SNKTRIDEANQRATKXL | 51 | 1.20 |
| K15A | SNKTRIDEANQRATAML | 52 | 0.12 |
| T14S | SNKTRIDEANQRASKML | 53 | 0.26 |
| T14B | SNKTRIDEANQRABKML | 54 | 1.20 |
| A13B | SNKTRIDEANQRBTKML | 55 | 0.79 |
| Q11A | SNKTRIDEANARATKML | 56 | 0.19 |
| Q11B | SNKTRIDEANBRATKML | 57 | 0.25 |
| Q11N | SNKTRIDEANNRATKML | 58 | 0.66 |
| N10A | SNKTRIDEAAQRATKML | 59 | 0.06 |
| A9B | SNKTRIDEBNQRATKML | 60 | 0.38 |
| E8Q | SNKTRIDQANQRATKML | 61 | 2.08 |
| D7N | SNKTRINEANQRATKML | 62 | 0.23 |

[a]Nonstandard amino acid abbreviations are: B, 2-aminobutyric acid; X, 2-aminohexanoic acid (norleucine)
[b]Initial hydrolysis rates relative to peptide [1-17]. Peptide concentrations were 1.0 mM.

As used herein, the term "botulinum toxin serotype B recognition sequence" is synonymous with "BoNT/B recognition sequence" and means a scissile bond together with adjacent or non-adjacent recognition elements, or both, sufficient for detectable proteolysis at the scissile bond by a BoNT/B under appropriate conditions. A scissile bond cleaved by BoNT/B can be, for example, Gln-Phe.

A variety of BoNT/B recognition sequences are well known in the art or can be defined by routine methods. Such BoNT/B recognition sequences can include, for example, a sequence corresponding to some or all of the hydrophilic core of a VAMP protein such as human VAMP-1 or human VAMP-2. A BoNT/B recognition sequence can include, without limitation, residues 33 to 94, residues 45 to 94, residues 55 to 94, residues 60 to 94, residues 65 to 94, residues 60 to 88 or residues 65 to 88 of human VAMP-2 (SEQ ID NO: 8), or residues 60 to 94 of human VAMP-1 (SEQ ID NO: 7). See, for example, Shone et al., *Eur. J. Biochem.* 217: 965-971 (1993). and U.S. Pat. No. 5,962,637. If desired, a similar BoNT/B recognition sequence can be prepared from a corresponding (homologous) segment of another BoNT/B-sensitive VAMP isoform or homolog such as human VAMP-1 or rat or chicken VAMP-2.

Thus, it is understood that a BoNT/B recognition sequence can correspond to a segment of a protein that is sensitive to cleavage by botulinum toxin serotype B, or can be substantially similar to such a segment of a BoNT/B-sensitive protein. As shown in Table D, a variety of naturally occurring proteins sensitive to cleavage by BoNT/B are known in the art and include, for example, human, mouse and bovine VAMP-1 and VAMP-2; rat VAMP-2; rat cellubrevin; chicken VAMP-2; *Torpedo* VAMP-1; sea urchin VAMP; *Aplysia* VAMP; squid VAMP; *C. elegans* VAMP; *Drosophila* n-syb; and leech VAMP. Thus, a BoNT/B recognition sequence included in a BoNT/B substrate can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, *Torpedo* VAMP-1, sea urchin VAMP, *Aplysia* VAMP, squid VAMP, *C. elegans* VAMP, *Drosophila* n-syb, leech VAMP, or another naturally occurring protein sensitive to cleavage by BoNT/B. Furthermore, as shown in Table D, comparison of native VAMP amino acid sequences cleaved by BoNT/B reveals that such sequences are not absolutely conserved (see, also, FIG. 4), indicating that a variety of amino acid substitutions and modifications relative to a naturally occurring VAMP sequence can be tolerated in a BoNT/B substrate of the invention.

TABLE D

Cleavage of VAMP[a],[b]

| Species-Isoform | Cleavage Sites | | | | SEQ ID NO: | Resistance to Cleavage by |
|---|---|---|---|---|---|---|
| | BoNT/F ⇓⇓ | BoNT/D | BoNT/B TeNT ⇓ | BoNT/G ⇓ | | |
| human mouse-VAMP-1 bovine | 53 dkvlerd | qkl | selddradalqagas qf | ess aa klkrkyww | 92 | none |
| human mouse-VAMP-2 bovine | 51 dkvlerd | qkl | selddradalqagas qf | ets aa klkrkyww | 90 | none |
| rat-VAMP-2 | 53 dkvlerd | qkl | selddradalqagas vf | ess aa klkrkyww | 92 | TeNT & BoNT/B |
| rat-VAMP-2 | 51 dkvlerd | qkl | selddradalqagas qf | ets aa klkrkyww | 90 | none |
| rat-Cellubrevin | 38 dkvlerd | qkl | selddradalqagas qf | ets aa klkrkyww | 77 | none |
| rat-TI-VAMP | 146 dlvaqrg | erl | ellidktenlvdssv tf | ktt sr nlaramcm | 175 | all |
| chicken-VAMP-1 | - ----erd | qkl | selddradalqagas vf | ess aa klkr---- | - | TeNT & BoNT/B |
| chicken-VAMP-2 | - ----erd | qkl | selddradalqagas qf | ets aa klkr---- | - | none |
| Torpedo-VAMP-1 | 55 dkvlerd | qkl | selddradalqagas qf | ess aa klkrkyww | 94 | none |
| sea urchin-VAMP | 35 dkvldrd | gal | svlddradalqqgas qf | etn ag klkrkyww | 74 | BoNT/F, D & G |
| *Aplysia*-VAMP | 41 ekvldrd | qki | sqlddraealqagas qf | eas ag klkrkyww | 80 | BoNT/G |
| squid-VAMP | 60 dkvlerd | ski | selddradalqagas qf | eas ag klkrkfww | 99 | BoNT/F & G |
| *C. elegans*-VAMP | 86 nkvmerd | vql | nsldhraevlqngas qf | qqs sr elkrqyww | 115 | BoNT/F, D & G |
| *Drosphila*-syb[a] | 67 ekvlerd | qkl | selgeradqleqgas qs | eqq ag klkrkqww | 106 | TeNT & BoNT/B & G |

TABLE D-continued

Cleavage of VAMP[a,b]

| Species-Isoform | Cleavage Sites | SEQ ID NO: | Resistance to Cleavage by |
|---|---|---|---|
| Drosphila-n-syb[b] | 61                                              100<br>ekvlerd skl selddradalqqgas qf eqq ag klkrkfwl | | BoNT/F & G |
| leech-VAMP | 49                                           88<br>dkvlekd qkl aeldgradalqagas qf eas ag klkrkfww | | BoNT/G |

[a] = Sequence corrected in position 93 (f>s).
[b] = Sequence corrected in position 68 (t>s).

As used herein, the term "botulinum toxin serotype C1 recognition sequence" is synonymous with "BoNT/C1 recognition sequence" and means a scissile bond together with adjacent or non-adjacent recognition elements, or both, sufficient for detectable proteolysis at the scissile bond by a BoNT/C1 under appropriate conditions. A scissile bond cleaved by BoNT/C1 can be, for example, Lys-Ala or Arg-Ala.

It is understood that a BoNT/C1 recognition sequence can correspond to a segment of a protein that is sensitive to cleavage by botulinum toxin serotype C1, or can be substantially similar to a segment of a BoNT/C1-sensitive protein. As shown in Table E, a variety of naturally occurring proteins sensitive to cleavage by BoNT/C1 are known in the art and include, for example, human, rat, mouse and bovine syntaxin 1A and 1B; rat syntaxins 2 and 3; sea urchin syntaxin; *Aplysia* syntaxin 1; squid syntaxin; *Drosophila* Dsynt1; and leech syntaxin 1. Thus, a BoNT/C1 recognition sequence useful in a BoNT/C1 substrate can correspond, for example, to a segment of human, rat, mouse or bovine syntaxin 1A or 1B, rat syntaxin 2, rat syntaxin 3, sea urchin syntaxin, *Aplysia* syntaxin 1, squid syntaxin, *Drosophila* Dsynt1, leech syntaxin 1, or another naturally occurring protein sensitive to cleavage by BoNT/C1. Furthermore, comparison of native syntaxin amino acid sequences cleaved by BoNT/C1 reveals that such sequences are not absolutely conserved (see Table E and FIG. 5), indicating that a variety of amino acid substitutions and modifications relative to a naturally occurring BoNT/C1-sensitive syntaxin sequence can be tolerated in a BoNT/C1 substrate useful in the invention.

TABLE E

Cleavage of syntaxin

| Species-Isoform | Cleavage Sites | SEQ ID NO: | Resistance to Cleavage by |
|---|---|---|---|
| | BoNT/C<br>⇓ | | |
| human<br>rat-syntaxin 1A<br>mouse<br>bovine | 245                          262<br>eravsdtk ka vkyqskar | | no |
| human<br>rat-syntaxin 1B<br>mouse<br>bovine | 244                          261<br>eravsdtk ka vkyqskar | | no |
| rat-syntaxin 2 | 245                          262<br>ehakeetk ka ikyqskar | | no |
| rat-syntaxin 3 | 244                          261<br>ekardetr ka mkyqgqar | | no |
| rat-syntaxin 4 | 244                          261<br>ergqehvk ia lenqkkar | | yes |
| chicken-syntaxin 1B | 239                          259<br>vpevfvtk sa vmyqcksr | | expected |
| sea urchin-syntaxin | 243                          260<br>vrrqndtk ka vkyqskar | | no |
| *Aplysia*-syntaxin 1 | 247                          264<br>etakmdtk ka vkyqskar | | no |
| squid-syntaxin | 248                          265<br>etakvdtk ka vkyqskar | | no |

TABLE E-continued

Cleavage of syntaxin

| Species-Isoform | Cleavage Sites | SEQ ID NO: | Resistance to Cleavage by |
|---|---|---|---|
| Drosophila-Dsynt 1 | 248                   265<br>qtatqdtk ka lkyqskar | | no |
| leech-syntaxin 1 | 251                   268<br>etaaadtk ka mkyqsaar | | no |

A variety of naturally occurring SNAP-25 proteins also are sensitive to cleavage by BoNT/C1, including human, mouse and rat SNAP-25; goldfish SNAP-25A and 25B; and *Drosophila* and leech SNAP-25. Thus, a BoNT/C1 recognition sequence useful in a BoNT/C1 substrate can correspond, for example, to a segment of human, mouse or rat SNAP-25, goldfish SNAP-25A or 25B, *Torpedo* SNAP-25, zebrafish SNAP-25, *Drosophila* SNAP-25, leech SNAP-25, or another naturally occurring protein sensitive to cleavage by BoNT/C1. As discussed above in regard to variants of naturally occurring syntaxin sequences, comparison of native SNAP-25 amino acid sequences cleaved by BoNT/C1 reveals significant sequence variability (see FIG. 3 and Table B above), indicating that a variety of amino acid substitutions and modifications relative to a naturally occurring BoNT/C1-sensitive SNAP-25 sequence can be tolerated in a BoNT/C1 substrate useful in the invention.

The term "botulinum toxin serotype D recognition sequence" is synonymous with "BoNT/D recognition sequence" and means a scissile bond together with adjacent or non-adjacent recognition elements, or both, sufficient for detectable proteolysis at the scissile bond by a BoNT/D under appropriate conditions. A scissile bond cleaved by BoNT/D can be, for example, Lys-Leu.

A variety of BoNT/D recognition sequences are well known in the art or can be defined by routine methods. A BoNT/D recognition sequence can include, for example, residues 27 to 116; residues 37 to 116; residues 1 to 86; residues 1 to 76; or residues 1 to 69 of rat VAMP-2 (SEQ ID NO: 90; Yamasaki et al., *J. Biol. Chem.* 269:12764-12772 (1994)). Thus, a BoNT/D recognition sequence can include, for example, residues 27 to 69 or residues 37 to 69 of rat VAMP-2 (SEQ ID NO: 90). If desired, a similar BoNT/D recognition sequence can be prepared from a corresponding (homologous) segment of another BoNT/D-sensitive VAMP isoform or homolog such as human VAMP-1 or human VAMP-2.

A BoNT/D recognition sequence can correspond to a segment of a protein that is sensitive to cleavage by botulinum toxin serotype D, or can be substantially similar to a segment of a BoNT/D-sensitive protein. As shown in Table D, a variety of naturally occurring proteins sensitive to cleavage by BoNT/D are known in the art and include, for example, human, mouse and bovine VAMP-1 and VAMP-2; rat VAMP-1 and VAMP-2; rat cellubrevin; chicken VAMP-1 and VAMP-2; *Torpedo* VAMP-1; *Aplysia* VAMP; squid VAMP; *Drosophila* syb and n-syb; and leech VAMP. Thus, a BoNT/D recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, *Torpedo* VAMP-1, *Aplysia* VAMP, squid VAMP, *Drosophila* syb or n-syb, leech VAMP, or another naturally occurring protein sensitive to cleavage by BoNT/D. Furthermore, as shown in Table D above, comparison of native VAMP amino acid sequences cleaved by BoNT/D reveals significant sequence variability (see, also, FIG. 4), indicating that a variety of amino acid substitutions and modifications relative to a naturally occurring BoNT/D-sensitive VAMP sequence can be tolerated in a BoNT/D substrate useful in the invention.

As used herein, the term "botulinum toxin serotype E recognition sequence" is synonymous with "BoNT/E recognition sequence" and means a scissile bond together with adjacent or non-adjacent recognition elements, or both, sufficient for detectable proteolysis at the scissile bond by a BoNT/E under appropriate conditions. A scissile bond cleaved by BoNT/E can be, for example, Arg-Ile.

One skilled in the art appreciates that a BoNT/E recognition sequence can correspond to a segment of a protein that is sensitive to cleavage by botulinum toxin serotype E, or can be substantially similar to a segment of a BoNT/E-sensitive protein. A variety of naturally occurring proteins sensitive to cleavage by BoNT/E are known in the art and include, for example, human, mouse and rat SNAP-25; mouse SNAP-23; chicken SNAP-25; goldfish SNAP-25A and SNAP-25B; zebrafish SNAP-25; *C. elegans* SNAP-25; and leech SNAP-25 (see Table B). Thus, a BoNT/E recognition sequence can correspond, for example, to a segment of human SNAP-25, mouse SNAP-25, rat SNAP-25, mouse SNAP-23, chicken SNAP-25, goldfish SNAP-25A or 25B, *C. elegans* SNAP-25, leech SNAP-25, or another naturally occurring protein sensitive to cleavage by BoNT/E. Furthermore, as shown in Table B and FIG. 3 above, comparison of native SNAP-23 and SNAP-25 amino acid sequences cleaved by BoNT/E reveals that such sequences are not absolutely conserved, indicating that a variety of amino acid substitutions and modifications relative to a naturally occurring BoNT/E-sensitive SNAP-23 or SNAP-25 sequence can be tolerated in a BoNT/E substrate useful in the invention.

The term "botulinum toxin serotype F recognition sequence," as used herein, is synonymous with "BoNT/F recognition sequence" and means a scissile bond together with adjacent or non-adjacent recognition elements, or both, sufficient for detectable proteolysis at the scissile bond by a BoNT/F under appropriate conditions. A scissile bond cleaved by BoNT/F can be, for example, Gln-Lys.

A variety of BoNT/F recognition sequences are well known in the art or can be defined by routine methods. A BoNT/F recognition sequence can include, for example, residues 27 to 116; residues 37 to 116; residues 1 to 86; residues 1 to 76; or residues 1 to 69 of rat VAMP-2 (SEQ ID NO: 90; Yamasaki et al., supra, 1994). A BoNT/F recognition sequence also can include, for example, residues 27 to 69 or residues 37 to 69 of rat VAMP-2 (SEQ ID NO: 90). It is understood that a similar BoNT/F recognition sequence can be prepared, if desired, from a corresponding (homologous)

segment of another BoNT/F-sensitive VAMP isoform or homolog such as human VAMP-1 or human VAMP-2.

A BoNT/F recognition sequence can correspond to a segment of a protein that is sensitive to cleavage by botulinum toxin serotype F, or can be substantially similar to a segment of a BoNT/F-sensitive protein. A variety of naturally occurring proteins sensitive to cleavage by BoNT/F are known in the art and include, for example, human, mouse and bovine VAMP-1 and VAMP-2; rat VAMP-1 and VAMP-2; rat cellubrevin; chicken VAMP-1 and VAMP-2; *Torpedo* VAMP-1; *Aplysia* VAMP; *Drosophila* syb; and leech VAMP (see Table D). Thus, a BoNT/F recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, *Torpedo* VAMP-1, *Aplysia* VAMP, *Drosophila* syb, leech VAMP, or another naturally occurring protein sensitive to cleavage by BoNT/F. Furthermore, as shown in Table D above, comparison of native VAMP amino acid sequences cleaved by BoNT/F reveals that such sequences are not absolutely conserved (see, also, FIG. 4), indicating that a variety of amino acid substitutions and modifications relative to a naturally occurring BoNT/F-sensitive VAMP sequence can be tolerated in a BoNT/F substrate useful in the invention.

As used herein, the term "botulinum toxin serotype G recognition sequence" is synonymous with "BoNT/G recognition sequence" and means a scissile bond together with adjacent or non-adjacent recognition elements, or both, sufficient for detectable proteolysis at the scissile bond by a BoNT/G under appropriate conditions. A scissile bond cleaved by BoNT/G can be, for example, Ala-Ala.

A BoNT/G recognition sequence can correspond to a segment of a protein that is sensitive to cleavage by botulinum toxin serotype G, or can be substantially similar to such a BoNT/G-sensitive segment. As illustrated in Table D above, a variety of naturally occurring proteins sensitive to cleavage by BoNT/G are known in the art and include, for example, human, mouse and bovine VAMP-1 and VAMP-2; rat VAMP-1 and VAMP-2; rat cellubrevin; chicken VAMP-1 and VAMP-2; and *Torpedo* VAMP-1. Thus, a BoNT/G recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, *Torpedo* VAMP-1, or another naturally occurring protein sensitive to cleavage by BoNT/G. Furthermore, as shown in Table D above, comparison of native VAMP amino acid sequences cleaved by BoNT/G reveals that such sequences are not absolutely conserved (see, also, FIG. 4), indicating that a variety of amino acid substitutions and modifications relative to a naturally occurring BoNT/G-sensitive VAMP sequence can be tolerated in a BoNT/G substrate useful in the invention.

As used herein, the term "tetanus toxin recognition sequence" means a scissile bond together with adjacent or non-adjacent recognition elements, or both, sufficient for detectable proteolysis at the scissile bond by a tetanus toxin under appropriate conditions. A scissile bond cleaved by TeNT can be, for example, Gln-Phe.

A variety of TeNT recognition sequences are well known in the art or can be defined by routine methods and include sequences corresponding to some or all of the hydrophilic core of a VAMP protein such as human VAMP-1 or human VAMP-2. A TeNT recognition sequence can include, for example, residues 25 to 93 or residues 33 to 94 of human VAMP-2 (SEQ ID NO: 8; Cornille et al., *Eur. J. Biochem.* 222:173-181 (1994); Foran et al., *Biochem.* 33: 15365-15374 (1994)); residues 51 to 93 or residues 1 to 86 of rat VAMP-2 (SEQ ID NO: 90; Yamasaki et al., supra, 1994); or residues 33 to 94 of human VAMP-1 (SEQ ID NO: 7). A TeNT recognition sequence also can include, for example, residues 25 to 86, residues 33 to 86 or residues 51 to 86 of human VAMP-2 (SEQ ID NO: 8) or rat VAMP-2 (SEQ ID NO: 90). It is understood that a similar TeNT recognition sequence can be prepared, if desired, from a corresponding (homologous) segment of another TeNT-sensitive VAMP isoform or species homolog such as human VAMP-1 or sea urchin or *Aplysia* VAMP.

Thus, a TeNT recognition sequence can correspond to a segment of a protein that is sensitive to cleavage by tetanus toxin, or can be substantially similar to a segment of a TeNT-sensitive protein. As shown in Table D above, a variety of naturally occurring proteins sensitive to cleavage by TeNT are known in the art and include, for example, human, mouse and bovine VAMP-1 and VAMP-2; rat VAMP-2; rat cellubrevin; chicken VAMP-2; *Torpedo* VAMP-1; sea urchin VAMP; *Aplysia* VAMP; squid VAMP; *C. elegans* VAMP; *Drosophila* n-syb; and leech VAMP. Thus, a TeNT recognition sequence can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, *Torpedo* VAMP-1, sea urchin VAMP, *Aplysia* VAMP, squid VAMP, *C. elegans* VAMP, *Drosophila* n-syb, leech VAMP, or another naturally occurring protein sensitive to cleavage by TeNT. Furthermore, comparison of native VAMP amino acid sequences cleaved by TeNT reveals that such sequences are not absolutely conserved (Table D and FIG. 4). This finding indicates that a variety of amino acid substitutions and modifications relative to a naturally occurring TeNT-sensitive VAMP sequence can be tolerated in a TeNT substrate useful in the invention.

As used herein, the term "peptidomimetic" is used broadly to mean a peptide-like molecule that is cleaved by the same clostridial toxin as the peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines, and are cleaved by the same clostridial toxin as the peptide substrate upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^\alpha$-$C^\alpha$ cyclized amino acid; an N-methylated amino acid; β- or γ-amino cycloalkane carboxylic acid; an α,β-unsaturated amino acid; a β,β-dimethyl or β-methyl amino acid; a β-substituted-2,3-methano amino acid; an $NC^\delta$ or $C^\alpha$-$C^\delta$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

In any of the methods of the invention, a clostridial toxin substrate can include one or multiple clostridial toxin cleavage sites for the same or different clostridial toxins. In particular embodiments, the invention provides methods that rely on a clostridial toxin substrate which contains a single clostridial toxin cleavage site. In other embodiments, the invention provides methods which rely on a clostridial toxin substrate which contains multiple cleavage sites for the same clostridial toxin. These cleavage sites can be incorporated within the same or different clostridial toxin recognition sequences. As non-limiting examples, a clostridial toxin substrate can have multiple cleavage sites for the same clostridial toxin intervening between the same fluorophore and bulking group or the same donor fluorophore and acceptor. A clostridial toxin substrate useful in the invention can contain, for example, two or more, three or more, five or more, or ten or more cleavage sites for the same clostridial toxin. A clostridial toxin substrate useful in the invention also can have, for example, two, three, four, five, six, seven, eight, nine or ten cleavage sites for the same clostridial toxin; the multiple cleavage sites can intervene between the same or different fluorophores and bulking groups, or between the same or different donor fluorophores and acceptors.

A clostridial toxin substrate useful in the invention also can include cleavage sites for different clostridial toxins. In particular embodiments, the invention provides a method that relies on a clostridial toxin substrate which includes multiple cleavage sites for different clostridial toxins all intervening between the same fluorophore and bulking group, or between the same donor fluorophore and acceptor. A clostridial toxin substrate can include, for example, cleavage sites for two or more, three or more, or five or more different clostridial toxins all intervening between the same fluorophore and bulking group. A clostridial toxin substrate also an include, for example, cleavage sites for two or more, three or more, or five or more different clostridial toxins all intervening between the same donor fluorophore and acceptor. A clostridial toxin substrate also can incorporate, for example, cleavage sites for two or more, three or more, or five or more different clostridial toxins intervening between at least two fluorophore-bulking group pairs or between at least two donor fluorophore-acceptor pairs. In particular embodiments, the invention provides a clostridial toxin substrate having cleavage sites for two, three, four, five, six, seven or eight different clostridial toxins, where the cleavage sites intervene between the same or different fluorophores and bulking groups, or between the same or different donor fluorophores and acceptors. In further embodiments, the invention provides a clostridial toxin substrate which has any combination of two, three, four, five, six, seven or eight cleavage sites for any combination of the following clostridial toxins: BoNT/A, BoNT/B, BoNT/C1, BoNT/D, BoNT/E, BoNT/F, BoNT/G and TeNT.

A method of the invention optionally can be performed with multiple substrates. In a method of the invention which relies on a clostridial toxin substrate containing a donor fluorophore-acceptor pair, a clostridial toxin substrate is treated with a sample, the substrate including a first donor fluorophore, a first acceptor having an absorbance spectrum which overlaps the emission spectrum of the first donor fluorophore, and a first clostridial toxin recognition sequence containing a cleavage site, where the cleavage site intervenes between the donor fluorophore and the acceptor and where, under the appropriate conditions, resonance energy transfer is exhibited between the first donor fluorophore and the first acceptor. If desired, a second clostridial toxin substrate can be included in the same assay; this second substrate contains a second donor fluorophore and second acceptor having an absorbance spectrum which overlaps the emission spectrum of the second donor fluorophore, and a second clostridial toxin recognition sequence that is cleaved by a different clostridial toxin than the toxin that cleaves the first clostridial toxin recognition sequence. The donor fluorophore-acceptor pair in the second substrate can be the same or different from the donor fluorophore-acceptor pair in the first substrate. In this way, a single sample can be simultaneously assayed for the presence of more than one clostridial toxin.

In a method of the invention which relies on a clostridial toxin substrate containing a donor fluorophore-acceptor pair, it is understood that one can assay for any combination of clostridial toxins, for example, two, three, four, five, six, seven, eight, or more clostridial toxins. One can assay, for example, any combination of two, three, four, five, six, seven or eight of BoNT/A, BoNT/B, BoNT/C1, BoNT/D, BoNT/E, BoNT/F, BoNT/G and TeNT. As an example, an assay can be performed with seven substrates, each of which includes fluorescein and tetramethylrhodamine flanking a BoNT/A, BoNT/B, BoNT/C1, BoNT/D, BoNT/E, BoNT/F or BoNT/G recognition sequence and cleavage site. These substrates can be treated with a sample under conditions suitable for botulinum toxin activity before exciting the donor fluorescein with plane polarized light at an absorption wavelength of about 488 nm and determining fluorescence polarization. A change in the fluorescence polarization is indicative of the presence or activity of at least one clostridial toxin. Such an assay can be useful, for example, for assaying food samples or tissue samples for the presence of any botulinum or other clostridial toxin and can be combined, if desired, with one or more subsequent assays for individual clostridial toxins or specific combinations of clostridial toxins.

In another embodiment, a single sample is assayed for two or more different clostridial toxins using two or more different clostridial toxin substrates, with each substrate containing a different donor fluorophore-acceptor pair. The use of multiple substrates can be useful for extending the dynamic range of an assay, as described, for example, in U.S. Pat. No. 6,180, 340. As an example of the use of multiple clostridial toxin substrates, a single sample can be assayed for the presence or activity of BoNT/A and BoNT/B using first and second clostridial toxin substrates: the first clostridial toxin substrate contains the donor fluorophore Alexa Fluor® 555 and the acceptor Alexa Fluor® 568 with an intervening BoNT/A recognition sequence, and a second clostridial toxin substrate contains the donor fluorophore Alexa Fluor® 700 and the acceptor Alexa Fluor® 750 with an intervening BoNT/B recognition sequence. Those skilled in the art understand that the first donor fluorophore can be excited before or after excitation of the second donor fluorophore, and that the change in fluorescence polarization of the first substrate can be determined before, at the same time, or after determining energy transfer of the second substrate.

In a further embodiment, a method of the invention is useful for assaying two or more different purified or isolated clostridial toxins using two or more different clostridial toxin substrates, with each substrate containing the same donor fluorophore-acceptor pair. In the endpoint format, the presence or activity of different serotypes is assayed by adding the serotypes sequentially and waiting between additions for the response to stabilize.

EXAMPLES

The following examples are intended to illustrate but not limit the present invention.

Example I

Preparation gf GFP-Snap25-His6-C-Alexa Fluor® 594 and GFP-Snap25-His6-C-Alexa Fluor®546 Substrates This example describes construction of substrates suitable for assaying for the presence or activity of a clostridial toxin using fluorescence polarization.

A. Construction of GFP-$SNAP25_{(134-206)}$-His6-C

A substrate was prepared as a fusion protein containing green fluorescent protein (GFP), murine SNAP-25 residues 134-206, a polyhistidine affinity tag (6×His), and a carboxy-terminal cysteine, with several components separated by peptide linkers. As described further below, the substrate was designed such that the GFP and terminal cysteine were present at opposite ends of SNAP-$25_{(134-206)}$.

The SNAP-25 sequence was obtained from pT25FL, a plasmid which contains the full-length mouse SNAP-25 gene inserted in frame with the 3' terminus of the glutathione-S-transferase (GST) gene (GST-$SNAP25_{(1-206)}$), provided by Professor Dolly (O'Sullivan et al., *J. Biol. Chem.* 274:36897-36904 (1999)). The SNAP-25 sequence from pT25FL was incorporated into a second expression vector, which was designed to have a BirAsp signal sequence for biotinylation and a polyhistidine affinity tag fused to the amino-terminus of residues 134 to 206 of SNAP-25 (BirAsp-polyHis-$SNAP25_{(134-206)}$, denoted "BA-SNAP"). The DNA sequence encoding $SNAP25_{(134-206)}$ was generated by PCR amplification of the appropriate region of the pT25FL plasmid with PCR primers 5'-GCT <u>AGATCT</u> CGA GTT AAC CAC TTC CCA GCA TCT TTG-3' (SEQ ID NO: 91; antisense) and 5'-ATC CGG AGG GTA ACA AAC GAT GCC-3' (SEQ ID NO: 92; sense) to produce a $SNAP25_{(134-206)}$ PCR product containing a Bgl II restriction site (PCR product A).

The BirAsp sequence, a natural substrate for biotinylation, as well as a polyhistidine affinity tag, were engineered for fusion upstream and in frame with the $SNAP25_{(134-206)}$ sequence using synthetic oligonucleotides SEQ ID NOS: 93 and 94, which contained a 20 bp complementary region. These oligonucleotides, 5'-CGA ATT <u>CCGCGG</u> GCC ACC ATG GGA GGA GGA CTG AAC GAC ATC TTC GAG GCT CAA AAG ATC-3' (SEQ ID NO: 93; sense; Sac II site underlined) and 5'-TCG TTT GTT ACC CTC CGG ATA TGA TGA TGA TGA TGA TGA TGA TGG GAT CCA TGC CAC TCG ATC TTT TGA GCC TCG AAG A-3' (SEQ ID NO: 94; antisense), were annealed, and the single strand overhangs filled by PCR amplification to yield PCR product B.

The two double stranded PCR products containing the coding sequences for $SNAP25_{(134-206)}$, denoted PCR product A, and BirAsp and polyhistidine, denoted PCR product B, were denatured and annealed. The 20 bp complementary sequence in the two gene fragments is shown in italics in PCR primers SEQ ID NO: 92 and SEQ ID NO: 94). After filling in the overhangs by PCR, the product was amplified with primers SEQ ID NO: 93 and SEQ ID NO: 91. The resulting PCR product, which encoded BirAsp-polyHis-$SNAP25_{(134-206)}$ (designated "BA-SNAP"), was digested with SacII and BglII, and the isolated gene insert ligated into pQBI25fA2 vector digested with SacII and BamHI, to yield plasmid pNTP12 (pQBI25fA2 containing BA-SNAP).

For expression and purification from *E. coli*, the BA-SNAP gene was transferred into a pTrc99A plasmid (Amersham Pharmacia Biotech). The BA-SNAP gene was isolated from pNTP12 by digestion with NcoI and XhoI followed by gel purification. Separately, the pTrc99A plasmid was digested with NcoI and SalI, and the isolated vector ligated to the BA-SNAP gene to yield plasmid pNTP14 (pTrc99A containing BA-SNAP).

For cloning of the BA-SNAP gene into plasmid pQE-50, the BA-SNAP fragment was PCR amplified from pNTP14 with primer SEQ ID NO: 91 and primer SEQ ID NO: 95 (5'-CGA <u>AGATCT</u> GGA GGA CTG AAC GAC ATC TTC-3' (sense; Bgl II site underlined)). After digestion with BglII and XhoI, the amplified PCR product was ligated into vector pQE-50, which had been digested with BamH I and Sal I. The resulting plasmid, which represents pQE50 containing BA-SNAP, was designated pNTP26.

A plasmid encoding the green fluorescent protein (GFP) fusion protein substrate was prepared by modifying vector pQBI T7-GFP (Quantum Biotechnologies; Carlsbad, Calif.) in three phases as described below. First, vector pQBI T7-GFP was PCR-modified to remove the stop codon at the 3' terminus of the GFP-coding sequence and to insert the coding sequence for a portion of the peptide linker separating GFP from the SNAP-25 fragment. Second, a DNA fragment coding for SNAP-$25_{(134-206)}$ was PCR amplified from pNTP26 using PCR primers designed to incorporate the coding sequence for the remainder of the peptide linker fused 5' to the SNAP-$25_{(134-206)}$ gene and a 6×His affinity tag fused 3' of the gene. The resultant PCR product was cloned into the modified pQBI vector described above to yield pQBI GFP-$SNAP25_{(134-206)}$.

Plasmid pQBI GFP-$SNAP25_{(134-206)}$ was then modified by site-directed mutagenesis to add a cysteine codon at the carboxy-terminus using primer SEQ ID NO: 96 (5'-GATGGTGATGGTGATG<u>ACA</u>GCCGCCACC GCCACC-3' (antisense primer, with the added nucleotides underlined) and its reverse complement (sense primer). The resulting plasmid, designated pQBI GFP-SNAP25 (Cys-Stop), is shown in FIG. 6A and was used for expression of GFP-$SNAP25_{(134-206)}$-6×His-Cys. The nucleic acid and predicted amino acid sequence for the GFP-$SNAP25_{(134-206)}$-6×His-cysteine construct is shown herein in FIG. 6B.

B. Expression and Characterization of GFP-$SNAP25_{(134-206)}$-His6-C

The pQBI GFP-SNAP25 (Cys-Stop) expression vector was transformed into *E. coli* BL21(DE3) cells (Novagen; Madison, Wis.; or Invitrogen; Carlsbad, Calif.) or into *E. coli* BL21-CodonPlus®(DE3)-RIL cells (Stratagene) containing the T7 RNA polymerase gene. Transformed cells were selected on LB-ampicillin plates overnight at 37° C. Single colonies were used to inoculate 1-3 mL starter cultures, which were in turn used to inoculate 0.5 to 1.0 L cultures. The large cultures were grown at 37° C. with shaking until $A_{595}$ reached 0.5-0.6, at which time they were removed from the incubator and were allowed to cool briefly. After induction of protein expression with 1 mM IPTG, GFP-$SNAP25_{(134-206)}$-His6-C substrate was expressed from the pQBI GFP-SNAP25 (Cys-Stop) plasmid overnight with shaking at 16° C. in order to facilitate formation of the GFP fluorophore. Cells from 250 mL aliquots of the expression cultures were collected by centrifugation (30 minutes, 6,000×g, 4° C.) and stored at −80° C. until needed.

Substrates were purified at 4° C. by a two-step procedure involving IMAC purification, followed by a de-salting step to remove NaCl and imidazole, typically yielding greater than 150 mg/L of purified substrate as follows. Cell pellets from 250 mL cultures were each resuspended in 7-12 mL Column Binding Buffer (25 mM HEPES, pH 8.0; 500 mM NaCl; 1 mM β-mercaptoethanol; 10 mM imidazole), lysed by sonication (1 minute 40 seconds in 10-second pulses at 38% amplitude), and clarified by centrifugation (16000 rpm, 4° C., 1 hour). Affinity resin (3-5 mL Talon SuperFlow $Co^{2+}$ per cell pellet) was equilibrated in a glass or disposable column support (Bio-Rad) by rinsing with 4 column volumes of sterile $ddH_2O$ and 4 column volumes of Column Binding Buffer. Clarified lysate was applied to the column in one of two ways: (1) Lysate was added to the resin and batch bound by horizontal incubation for 1 hour with gentle rocking or (2) Lysate was applied to the vertical column and allowed to enter the column slowly by gravity flow. Following batch binding only, the column was righted and the solution drained, collected, and passed over the resin again. In both cases, after the lysate had been applied, the column was washed with 4-5 column volumes of Column Binding Buffer. In some cases, the column was further washed with 1-2 column volumes of Column Wash Buffer (25 mM HEPES, pH 8.0; 500 mM NaCl; 1 mM β-mercaptoethanol; 20 mM imidazole). Protein was eluted with 1.5 to 2.0 column volumes of Column Elution Buffer (25 mM HEPES, pH 8.0; 500 mM NaCl; 1 mM β-mercaptoethanol; 250 mM imidazole), which was collected in fractions of ~1.4 mL. The green fractions were combined, concentrated with a centrifugal filter (10,000 or 30,000 molecular weight cut-off) and desalted by FPLC (BioRad Biologic DuoLogic, QuadTec UV-Vis detector) with a HiPrep 26/10 size exclusion column (Pharmacia) and an isocratic mobile phase of chilled Fusion Protein Desalting Buffer (50 mM HEPES, pH 7.4, 4° C.) at a flow rate of 10 mL/minute. Desalted protein was collected as a single fraction, and the concentration determined using a BioRad Protein Assay. The GFP-SNAP25$_{(134-206)}$-His6-C substrate was analyzed by reducing SDS-PAGE. The protein solution was subsequently divided into 500 μL aliquots, flash-frozen with liquid nitrogen and stored at −80° C. Once defrosted, a working aliquot was stored at 4° C., protected from light.

C. Labeling with Alexa Fluor® 594 and Alexa Fluor® 546

Figure 7A:
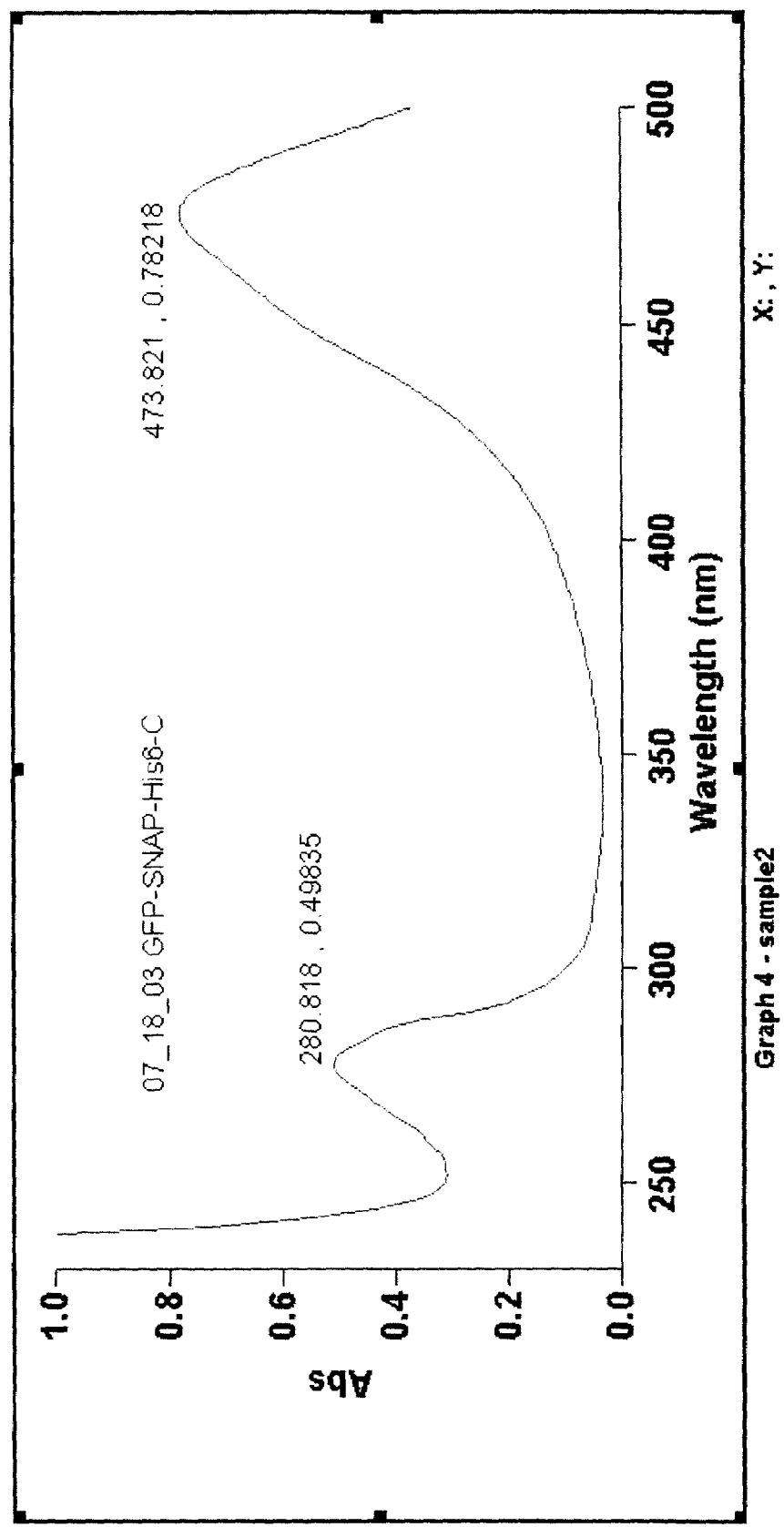
FIG. 7 shows (A) the absorption spectrum and (B) the excitation (dotted) and emission (bold) spectra of GFP-SNAP25$_{(134-206)}$-His6C.
Figure 7B:
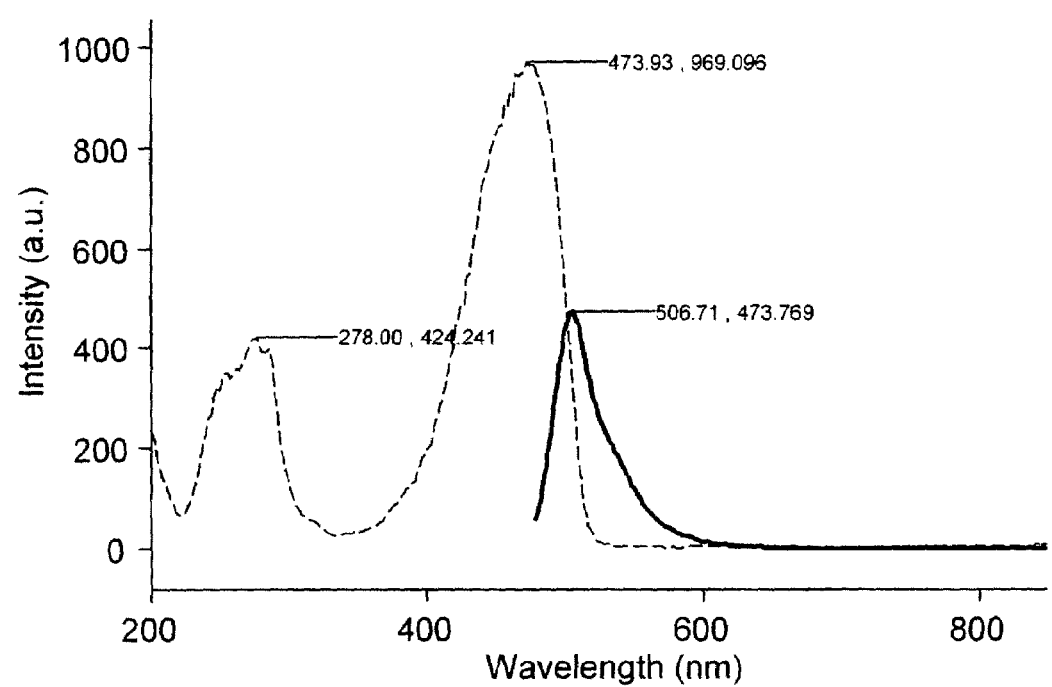

The GFP-SNAP25$_{(134-206)}$-His6-C construct contains a single cysteine residue which is solvent exposed although there are three buried cysteine residues within GFP which are not available for chemical modification (Selvin, supra, 2000; Heyduk, Curr. Opin. Biotech. 13:292-296 (2002)). The carboxy-terminal cysteine residue can therefore be selectively labeled using a fluorophore-maleimide at neutral pH. Shown in FIGS. 7A and 7B, respectively, are the absorption and emission/excitation spectra of purified GFP-SNAP25$_{(134-206)}$-His6-C protein. The concentration of the protein solution was determined to be 2.74 mg/ml based on the theoretical molar extinction coefficient of 20250 $M^{-1}cm^{-1}$ as calculated from the primary sequence of the construct. The molecular weight of the purified GFP-SNAP25$_{(134-206)}$-His6-C protein was confirmed to be about 37,000 using Matrix Assisted Laser Desorption Time of Flight mass spectrometry (MALDI-TOF).

Labeling with Alexa Fluor® 594 was performed essentially as follows. The C-terminal cysteine residue of the GFP-SNAP25$_{(134-206)}$-His6-C protein was labeled by adding a concentrated solution of Alexa Fluor® 594 (Molecular Probes, Inc.) in dry dimethyl formamide (DMF) to a final concentration of 20:1 molar excess of fluorophore to protein. The protein/fluorophore solution was kept at 4° C. in the refrigerator overnight and subsequently dialyzed against 20 mM HEPES pH 6.9.

Figure 8A:
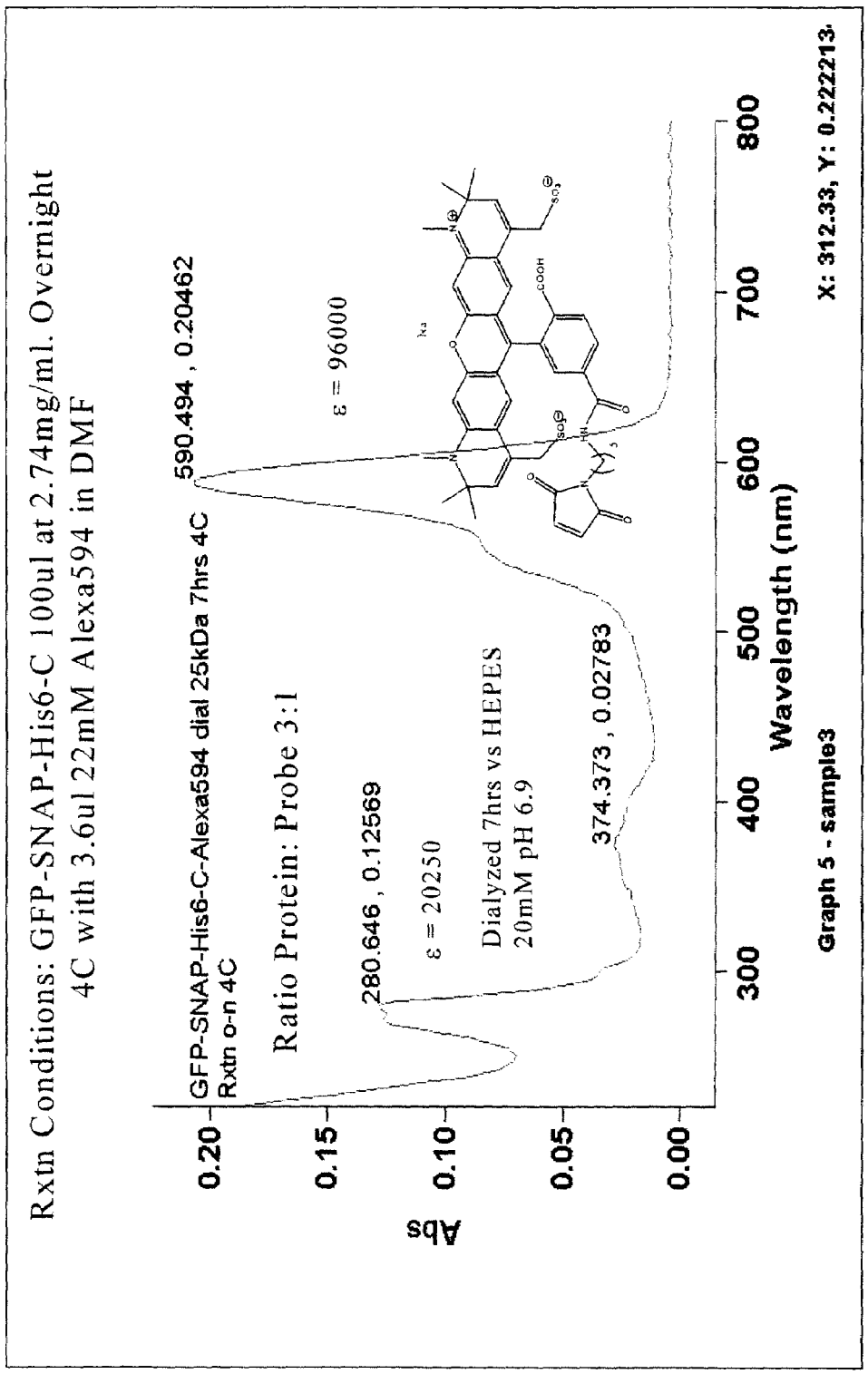
FIG. 8 shows (A) the UV-VIS absorption spectrum and (B) the excitation (bold) and emission (dotted) spectra of GFP-SNAP25$_{(134-206)}$-His6C-Alexa Fluor® 594.
Figure 8B:
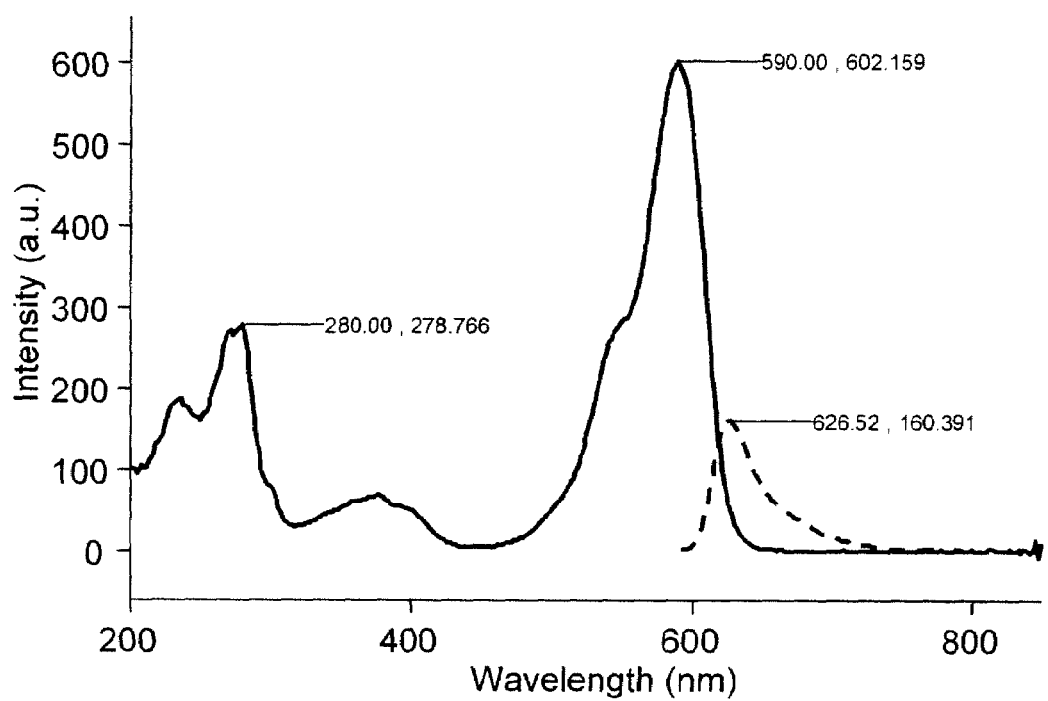
Figure 9B:
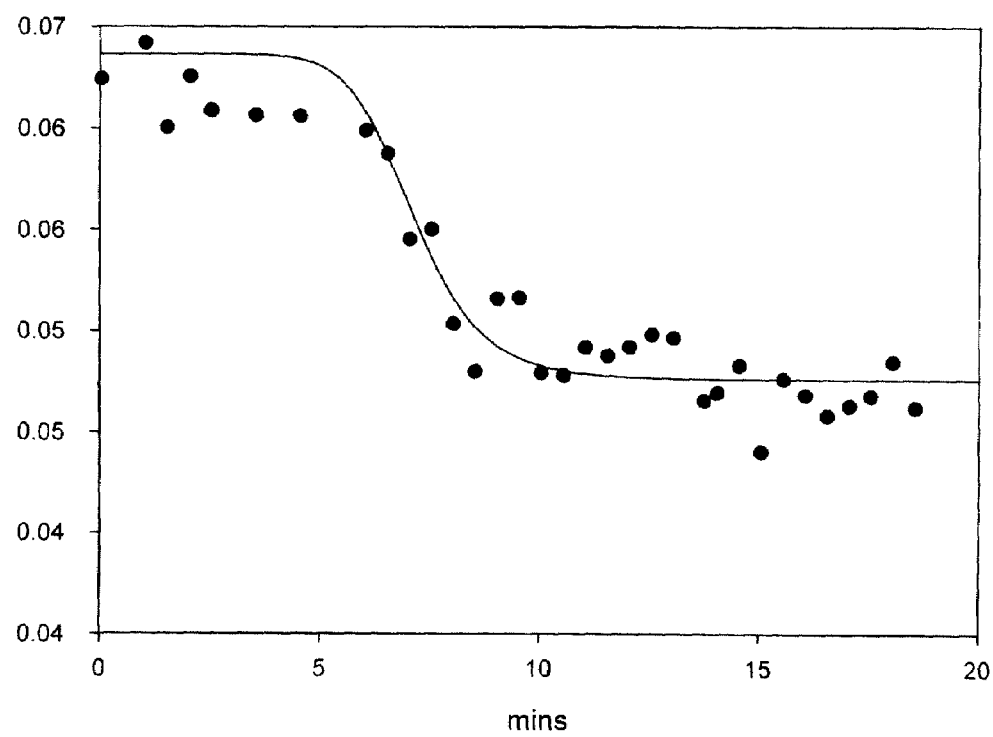
FIG. 9 shows turnover of the GFP-SNAP25$_{(134-206)}$-His6C-Alexa Fluor® 594 substrate using reduced BoNT/A at various concentrations. The arrow indicates when the reduced toxin complex was added.
Figure 9C:
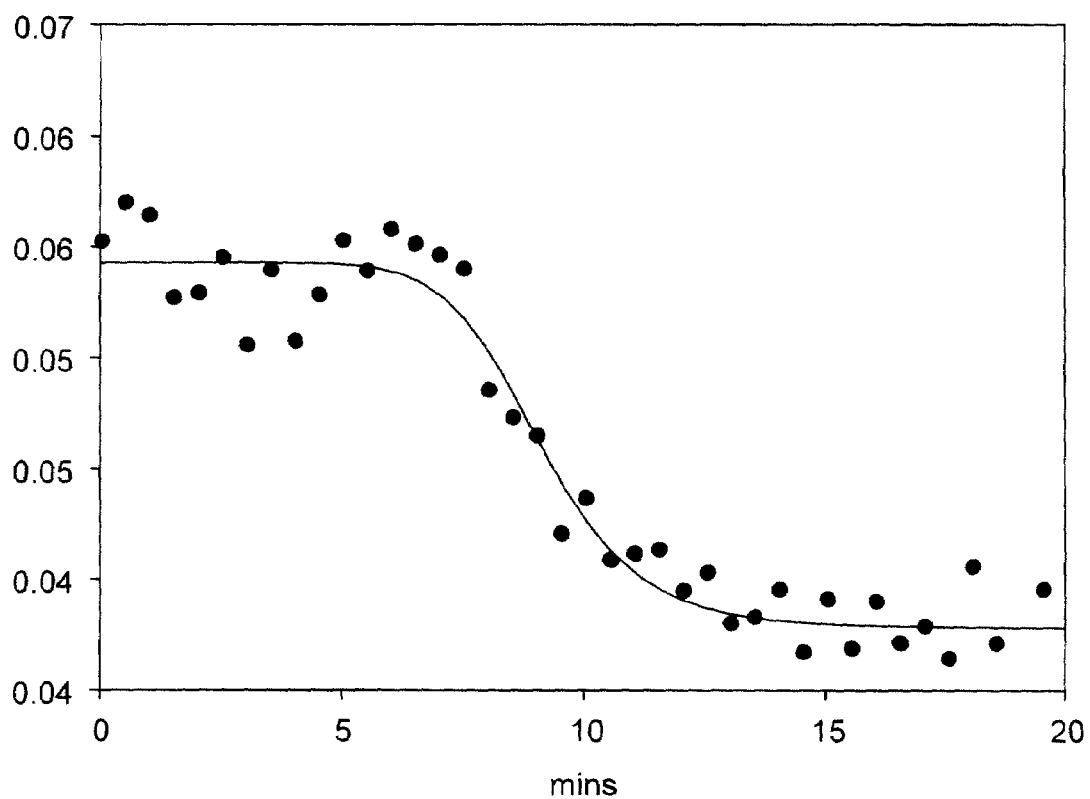
Figure 9D:
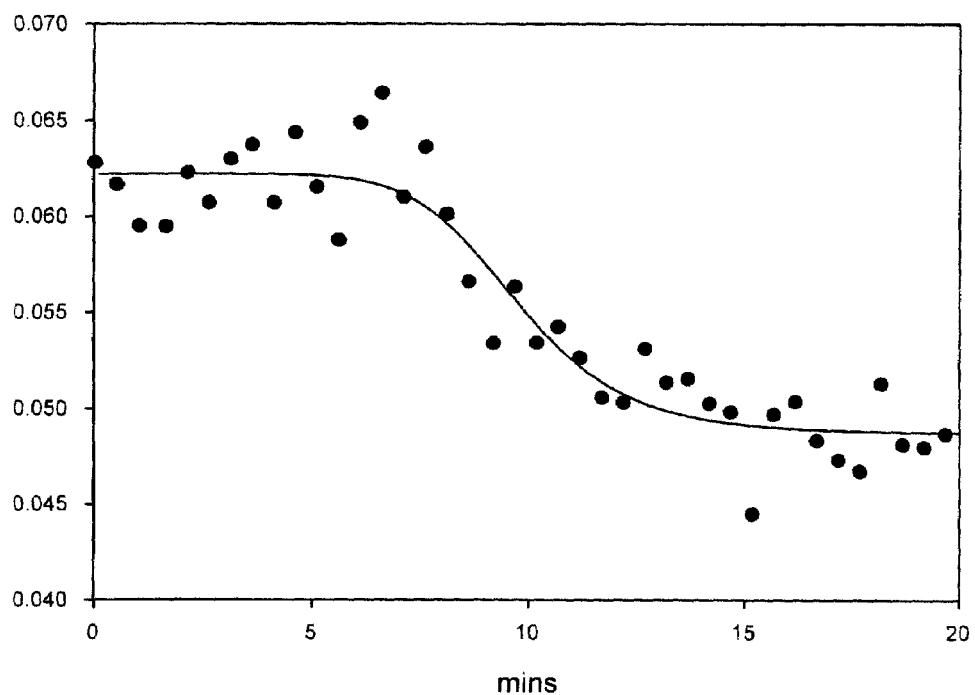
Figure 9E:
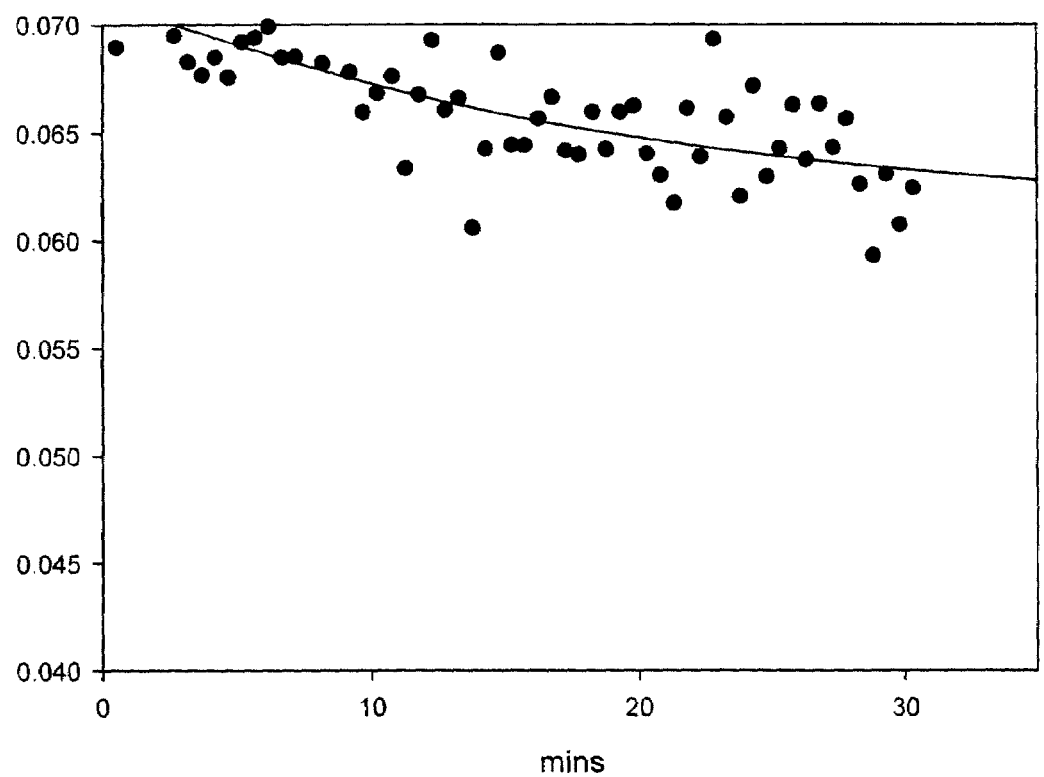

The absorption spectrum of the GFP-SNAP25$_{(134-206)}$-His6-C protein labeled with Alexa Fluor® 594 is shown in FIG. 8A following dialysis against 20 mM HEPES pH 6.9, which is the pH used for assaying enzymatic activity of reduced bulk toxin or purified BoNT-A light chain. The labeling ratio, as calculated from the absorption spectrum using the theoretical extinction coefficient of the GFP-SNAP25$_{(134-206)}$-His6-C construct, was approximately 3:1 (protein: Alexa probe). Shown in FIG. 8B are the excitation and emission spectra of labeled GFP-SNAP25$_{(134-206)}$-His6-C-Alexa Fluor® 594 after extensive dialysis for 20 hours with three changes of buffer to remove free probe.

Labeling with Alexa Fluor® 546 was performed essentially as follows with all procedures carried out on ice or at 4° C. Four microliters of a 10 mM aqueous solution of Alexa Fluor® 546 $C_5$ maleimide (MW 1,034.37; Molecular Probes) were added to 200 μL of GFP-$SNAP25_{(134-206)}$-His6-C (135 μM in 25 mM HEPES buffer, pH 7.2), mixed well, and incubated at 4° C. overnight. The reactions were transferred to Biomax Ultrafree centrifugal filters (30 KDa NMWL; Millipore), concentrated, and then reconcentrated two times from 25 mM HEPES, pH 7.2, to remove most of the excess Alexa Fluor® 546. To remove the remaining unreacted Alexa Fluor® 546, the concentrated solutions were transferred to Spin Microdialyzers (Harvard Apparatus) and each was dialyzed against 500 mL 20 mM HEPES, pH 6.9, for 1 hour, and against 3×250 mL of that buffer for about 1.5 hours each. A small aliquot was removed for fluorescence measurements, and the balance of the reaction was flash-frozen in liquid nitrogen and stored at −80° C.

Example II

Clostridial Toxin Complex Activity Assayed Using Fluorescence Polarization

This example demonstrates that a fluorescence polarization assay can be used to determine the presence or activity of a clostridial toxin.

The GFP-$SNAP25_{(134-206)}$-His6-C protein labeled with Alexa Fluor® 594 was tested for its utility as a suitable substrate for BoNT/A reduced bulk toxin by recording the change in polarization over time. A Cary Eclipse spectrofluorometer (Varian, Inc.; Palo Alto, Calif.) equipped with motorized thin-film polarizers was used to monitor the reaction. The excitation wavelength was set at 590 nm, and polarized emission was recorded at 620 nm.

Several dilutions of BoNT/A bulk toxin or BoNT/A light chain were prepared, and fluorescence polarization monitored over time. For both bulk toxin and light chain, fluorescence polarization was reduced at or shortly after the time the diluted toxin was added. FIG. 9 shows the data for bulk BoNT/A toxin proteolysis of GFP-$SNAP25_{(134-206)}$-His6-C-Alexa Fluor® 594. As shown in panel 9D, toxin was detected at a concentration of as little as about 50 ng/ml.

These results demonstrate that the presence or activity of a clostridial toxin can be sensitively determined using synthetic substrates assayed by fluorescence polarization.

Example III

Clostridial Toxin Complex Activity Assayed Using Fluorescence Polarization in Combination with Fluorescence Resonance Energy Transfer This example demonstrates that fluorescence polarization can be assayed to determine the presence or activity of a clostridial toxin using a substrate which exhibits fluorescence resonance energy transfer.

The GFP-SNAP25$_{(134-206)}$-His6-C protein labeled with Alexa Fluor® 546 as described above was utilized as a substrate for BoNT/A. As indicated above, the photoselection properties of GFP and Alexa Fluor® 546 provide for fluorescence resonance energy transfer (FRET) between the donor fluorophore GFP and the acceptor Alexa Fluor® 546. Steady-state polarization measurements were carried out in a Cary Eclipse spectrophotometer (Varian). Excitation was at 474 nm, the excitation maximum of the GFP component. Emission was measured at the Alexa Fluor® 546 fluorescence maximum of 570 nm. In all cases, a dual path length cuvette (10 mm by 2 mm) was utilized, and the emission viewed through the 2 mm path. A solution of 390 µL Toxin Reaction Buffer (50 mM HEPES, pH 7.2; 0.1% v/v TWEEN-20; 10 µM Zn Cl$_2$, 10 mM DTT) and 10 µL of GFP-SNAP25$_{(134-206)}$-His6-C-Alexa Fluor® 546 was placed in the cuvette and allowed to equilibrate to 30° C. When the polarization measurements, which were taken at 30 second intervals, were stabilized, 10 µL of recombinant BoNT/A light chain (rLC/A) at a concentration of 1.0 µg/µL, 0.5 µg/µL, 0.25 µg/µL, or 0.1 µg/µL was added to the cuvette. Measurements continued to be taken until the polarization again stabilized.

Figure 10A:
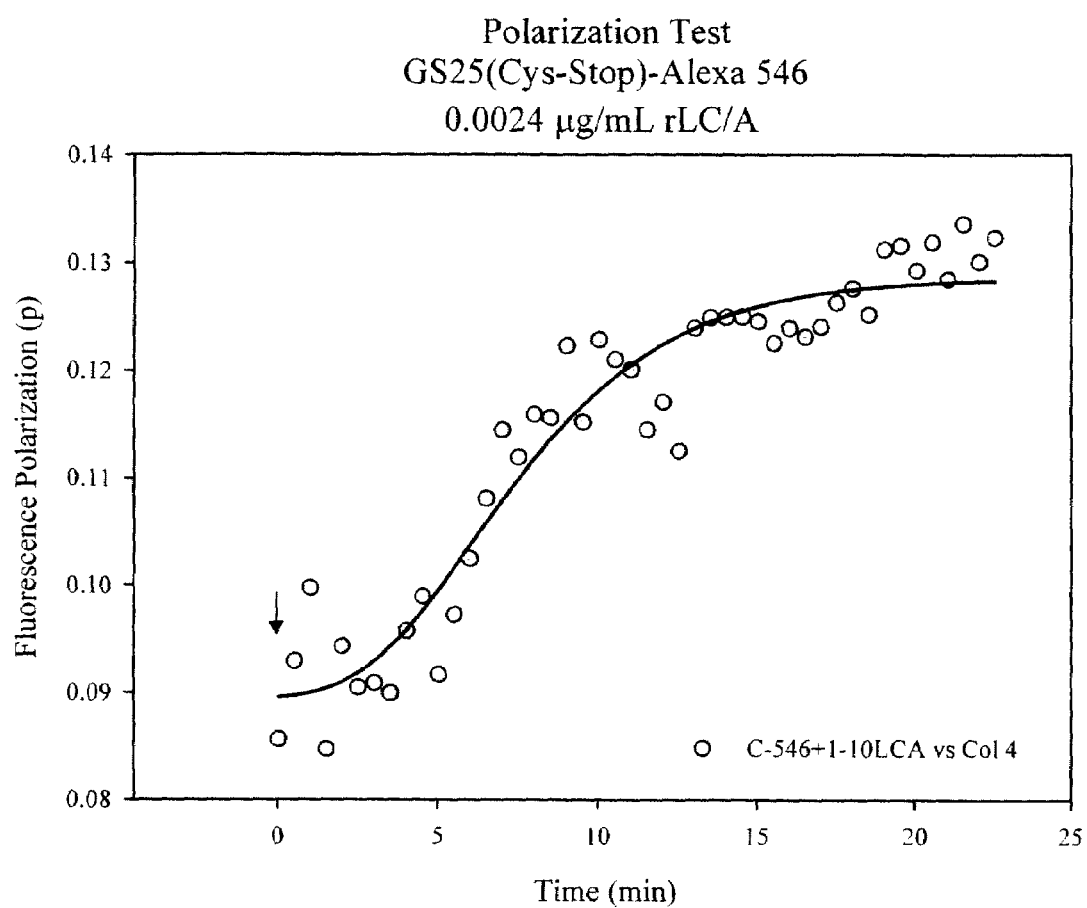
FIG. 10 shows turnover of the GFP-SNAP25$_{(134-206)}$-His6C-Alexa Fluor® 546 substrate using recombinant BoNT/A light chain. The arrow indicates addition of the BoNT/A light chain.
Figure 10B:
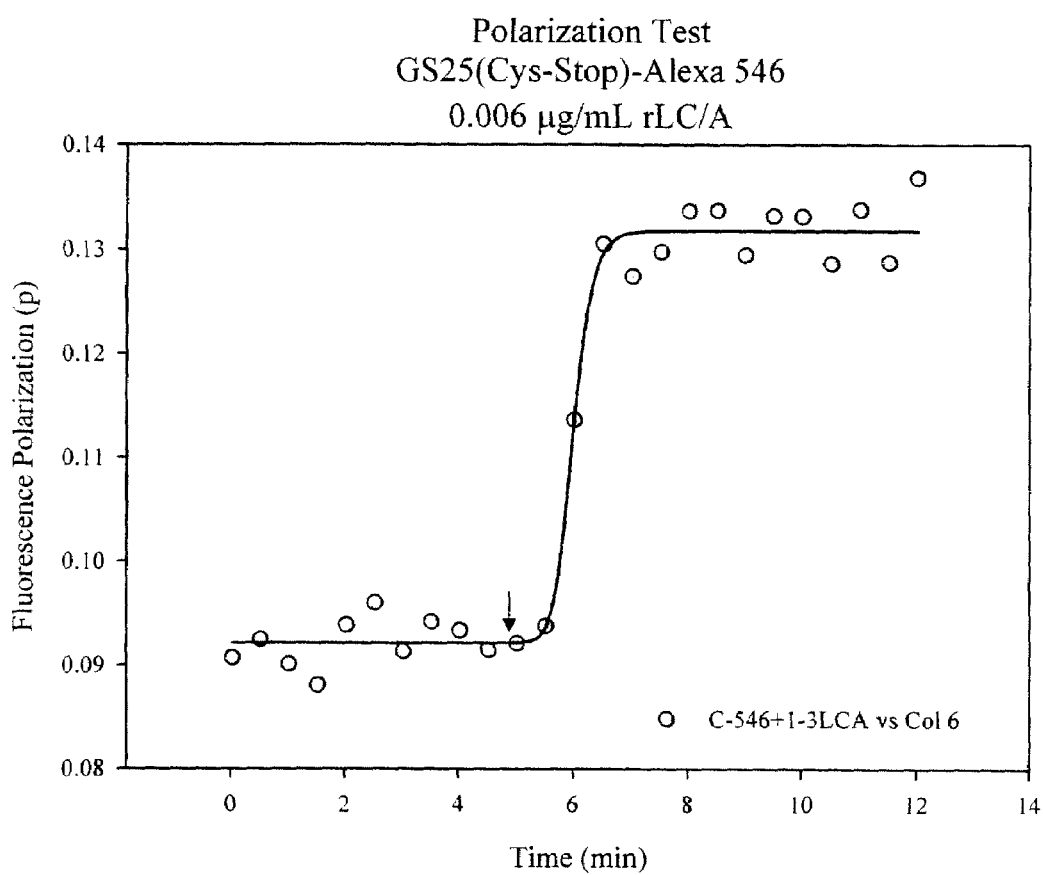

As shown in FIG. 10, fluorescence polarization increased upon addition of recombinant BoNT/A light chain which results in substrate cleavage. As compared to the substrate having GFP and Alexa Fluor® 594, the fluorescence resonance energy transfer enhanced the polarization change upon turnover, thereby increasing the sensitivity of the assay. The overall change in polarization using the GFP-SNAP25$_{(134-206)}$-His6-C-Alexa Fluor® 546 substrate was about 40 mP, twice the magnitude of the depolarization of approximately 20 mP observed during proteolysis of GFP-SNAP25$_{(134-206)}$-His6-C-Alexa Fluor® 594.

These results indicate that fluorescence polarization can be combined with fluorescence resonance energy transfer for enhanced sensitivity in assaying for the presence or activity of a clostridial toxin.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the following claims.

We claim:

1. A method of determining the presence or activity of a botulinum toxin type A, comprising the steps of:
   (a) measuring fluorescence polarization of a botulinum toxin type A substrate by exciting said botulinum toxin type A substrate with plane polarized light, said botulinum toxin type A substrate comprising
      (i) a donor fluorophore;
      (ii) an acceptor having an absorbance spectrum overlapping the emission spectrum of said donor fluorophore; and
      (iii) a botulinum toxin type A recognition sequence comprising a cleavage site, wherein said cleavage site intervenes between said donor fluorophore and said acceptor;
   (b) treating said botulinum toxin type A substrate with a sample, under conditions suitable for botulinum toxin type A protease activity; and
   (c) measuring fluorescence polarization of said treated botulinum toxin type A substrate by exciting said treated botulinum toxin type A substrate with plane polarized light;
      wherein an increase in said fluorescence polarization measured in step (c) relative to said fluorescence polarization measured in step (a) is indicative of the activity of said botulinum toxin type A in said sample due to cleavage of said treated botulinum toxin type A substrate by said botulinum toxin type A;
      wherein a decrease in said fluorescence polarization measured in step (c) relative to said fluorescence polarization measured in step (a) is indicative of the presence of said botulinum toxin type A in said sample due to complex formation of said clostridial toxin with said treated botulinum toxin type A substrate; and
      wherein no substantial change in said fluorescence polarization measured in step (c) relative to said fluorescence polarization measured in step (a) is indicative of the lack of presence or activity of said botulinum toxin type A in said sample.

2. The method of claim 1, wherein said donor fluorophore is a fluorescent protein.

3. The method of claim 2, wherein said fluorescent protein is a green fluorescent protein, a blue fluorescent protein, a cyan fluorescent protein, a yellow fluorescent protein, or a red fluorescent protein.

4. The method of claim 1, wherein said donor fluorophore is a fluorescein arsenical hairpin binding dye or a resorufin arsenical hairpin binding dye.

5. The method of claim 1, wherein said donor fluorophore is selected from a fluorescin or a fluorescin derivative, a rhodamine or a rhodamine derivative, and a cyanine or a cyanine derivative.

6. The method of claim 5, wherein said fluorescin or said fluorescin derivative is selected from diaminotriazinylaminofluorescein (DTAF), carboxyfluorescein (FAM), a biarsenic-based fluorescein or fluorescein derivative, and a dipyrromethene boron d fluoride-based fluorescein or fluorescein derivative.

7. The method of claim 5, wherein said rhodamine or said rhodamine derivative is selected from tetramethylcarboxyrhodamine (TMR), carboxy-x-rhodamine (ROX), rhodamine green, octadecylrhodamine, a biarsenic-based rhodamine or rhodamine derivative, and a dipyrromethene boron difluoride-based rhodamine or rhodamine derivative.

8. The method of claim 5, wherein said cyanine or said cyanine derivative is indocarbocyanine.

9. The method of claim 1, wherein said donor fluorophore has a fluorescence lifetime of at least 0.5 nanoseconds, at least 5 nanoseconds, or at least 10 nanoseconds.

10. The method of claim 1, wherein said acceptor is a fluorescent protein.

11. The method of claim 10, wherein said fluorescent protein is a green fluorescent protein, a blue fluorescent protein, a cyan fluorescent protein, a yellow fluorescent protein, or a red fluorescent protein.

12. The method of claim 1, wherein said acceptor is a fluorescein arsenical hairpin binding dye or a resorufin arsenical hairpin binding dye.

13. The method of claim 1, wherein said acceptor is selected from a fluorescin or a fluorescin derivative, a rhodamine or a rhodamine derivative, and a cyanine or a cyanine derivative.

14. The method of claim 13, wherein said fluorescin or said fluorescin derivative is selected from diaminotriazinylaminofluorescein (DTAF), carboxyfluorescein (FAM), a biarsenic-based fluorescein or fluorescein derivative, and a dipyrromethene boron difluoride-based fluorescein or fluorescein derivative.

15. The method of claim 13, wherein said rhodamine or said rhodamine derivative is selected from tetramethylcarboxyrhodamine (TMR), carboxy-x-rhodamine (ROX), rhodamine green, octadecylrhodamine, a biarsenic-based rhodamine or rhodamine derivative, and a dipyrromethene boron difluoride-based rhodamine or rhodamine derivative.

16. The method of claim 13, wherein said cyanine or said cyanine derivative is indocarbocyanine.

17. The method of claim 1, wherein said acceptor has a fluorescence lifetime of at least 0.5 nanoseconds, at least 5 nanoseconds, or at least 10 nanoseconds.

18. The method of claim 1, wherein said botulinum toxin type A recognition sequence comprises at least 100 residues or at least 200 residues.

19. The method of claim 1, wherein said botulinum toxin type A recognition sequences comprises at least six consecutive residues of SNAP-25, or a peptidomimetic thereof, said six consecutive residues comprising Gln-Arg, or a peptidomimetic thereof.

20. The method of claim 19, wherein said botulinum toxin type A recognition sequence comprises SEQ ID NO: 30, SEQ ID NO: 31, SEQ ID NO: 32, SEQ ID NO: 33, SEQ ID NO: 34, SEQ ID NO: 35, residues 134 to 206 of SEQ ID NO: 2, or a peptidomimetic thereof.

21. The method of claim 1, wherein said clostridial toxin substrate further comprises a bulking group.

22. The method of claim 1, wherein said bulking group is greater than 1 KDa, greater than 5 kDa, or greater than 10 kDa.

23. The method of claim 1, wherein in step (c) said increased fluorescence polarization or said decreased fluorescence polarization at least 5 mP.

24. The method of claim 1, wherein in step (c) said increased fluorescence polarization or said decreased fluorescence polarization at least 15 mP.

25. The method of claim 1, wherein said sample is a cell, a crude cell lysate, or a fractionated or partially purified cell lysate.

26. The method of claim 1, wherein said sample is a soil sample, a water sample, a pond sediment, an intestinal sample, or a tissue sample.

27. The method of claim 1, wherein said sample is raw food, cooked food, partially cooked food, processed food, beverage, or animal feed.

28. The method of claim 1, wherein said botulinum toxin type A recognition sequences comprises at least six consecutive residues of SNAP-25, said six consecutive residues comprising Gln-Arg.

\* \* \* \* \*

UNITED STATES PATENT AND TRADEMARK OFFICE
CERTIFICATE OF CORRECTION

PATENT NO. : 7,632,655 B2  Page 1 of 2
APPLICATION NO. : 12/125723
DATED : December 15, 2009
INVENTOR(S) : Williams et al.

It is certified that error appears in the above-identified patent and that said Letters Patent is hereby corrected as shown below:

On page 2, under "Other Publications", in column 2, line 28, delete "I-93" and insert -- 1-93 --, therefor.

On page 2, under "Other Publications", in column 2, line 31, delete "synaptosomeassociated" and insert -- synaptosome associated --, therefor.

On page 3, under "Other Publications", in column 1, line 43, delete "1.203-210" and insert -- 1:203-210 --, therefor.

On page 4, under "Other Publications", in column 1, line 8, after "activities" insert -- of botulinum --.

On page 4, under "Other Publications", in column 2, line 12, delete "Reinin" and insert -- Renin --, therefor.

In column 3, line 7, delete "SNAP25$_{(134-206)}$-6" and insert -- SNAP25$_{(134-206)}$-6 --, therefor.

In column 3, line 9, delete "SNAP25$_{(134-206)}$-6" and insert -- SNAP25$_{(134-206)}$-6 --, therefor.

In column 18, line 43, delete "5-(((2-iodoaacetyl)" and insert -- 5(-(((2-iodoaacetyl) --, therefor.

In column 37, line 12, delete "gf" and insert -- of --, therefor.

In column 96, line 65, in Claim 5, delete "fluorescin" and insert -- fluorescein --, therefor.

In column 96, line 65, in Claim 5, delete "fluorescin" and insert -- fluorescein --, therefor.

In column 97, line 5, in Claim 6, delete "d fluoride-based" and insert -- difluoride-based --, therefor.

In column 97, line 29, in Claim 13, delete "fluorescin" and insert -- fluorescein --, therefor.

In column 97, line 29, in Claim 13, delete "fluorescin" and insert -- fluorescein --, therefor.

Signed and Sealed this

Eighteenth Day of May, 2010

David J. Kappos
*Director of the United States Patent and Trademark Office*

In column 98, line 22, in Claim 22, delete "1 KDa," and insert -- 1 kDa, --, therefor.